US012371683B2

(12) United States Patent
Park et al.

(10) Patent No.: US 12,371,683 B2
(45) Date of Patent: Jul. 29, 2025

(54) HYALURONIDASE VARIANTS AND PHARMACEUTICAL COMPOSITION COMPRISING THE SAME

(71) Applicant: ALTEOGEN Inc., Daejeon (KR)

(72) Inventors: Soon Jae Park, Daejeon (KR); Hye-Shin Chung, Daejeon (KR); Seung Joo Lee, Daejeon (KR); Sun-Ah You, Daejeon (KR); Hyung-Nam Song, Daejeon (KR); Chang Woo Lee, Daejeon (KR)

(73) Assignee: ALTEOGEN Inc., Daejeon (KR)

( * ) Notice: Subject to any disclaimer, the term of this patent is extended or adjusted under 35 U.S.C. 154(b) by 1258 days.

(21) Appl. No.: 16/628,258

(22) PCT Filed: Jul. 25, 2019

(86) PCT No.: PCT/KR2019/009215
§ 371 (c)(1),
(2) Date: Jan. 2, 2020

(87) PCT Pub. No.: WO2020/022791
PCT Pub. Date: Jan. 30, 2020

(65) Prior Publication Data
US 2021/0155913 A1    May 27, 2021

(30) Foreign Application Priority Data

Jul. 25, 2018    (KR) ........................ 10-2018-0086308
Mar. 15, 2019    (KR) ........................ 10-2019-0029758

(51) Int. Cl.
   *C12N 9/24*      (2006.01)
   *A61K 45/06*    (2006.01)
   *C07K 14/00*    (2006.01)

(52) U.S. Cl.
   CPC ............ *C12N 9/2402* (2013.01); *A61K 45/06* (2013.01); *C07K 14/00* (2013.01); *C12Y 302/01035* (2013.01)

(58) Field of Classification Search
None
See application file for complete search history.

(56) References Cited

U.S. PATENT DOCUMENTS

| | | | |
|---|---|---|---|
| 5,721,348 A | 2/1998 | Primakoff et al. | |
| 5,854,046 A | 12/1998 | Au-Young et al. | |
| 7,767,429 B2 * | 8/2010 | Bookbinder | A61P 17/02 435/201 |
| 8,105,586 B2 | 1/2012 | Bookbinder et al. | |
| 8,202,517 B2 | 6/2012 | Bookbinder et al. | |
| 8,257,699 B2 | 9/2012 | Bookbinder et al. | |
| 8,288,142 B2 | 10/2012 | Uvarkina et al. | |
| 8,431,124 B2 | 4/2013 | Bookbinder et al. | |
| 8,431,380 B2 | 4/2013 | Bookbinder et al. | |
| 8,450,470 B2 | 5/2013 | Bookbinder et al. | |
| 8,580,252 B2 | 11/2013 | Bookbinder et al. | |
| 8,765,685 B2 | 7/2014 | Bookbinder et al. | |
| 8,772,246 B2 | 7/2014 | Bookbinder et al. | |
| 8,927,249 B2 | 1/2015 | Wei et al. | |
| 9,211,315 B2 | 12/2015 | Bookbinder et al. | |
| 9,284,543 B2 | 3/2016 | Wei et al. | |
| 9,447,401 B2 | 9/2016 | Wei et al. | |
| 9,562,223 B2 | 2/2017 | Bookbinder et al. | |
| 9,677,061 B2 | 6/2017 | Bookbinder et al. | |
| 9,677,062 B2 | 6/2017 | Bookbinder et al. | |
| 10,286,044 B2 | 5/2019 | Bookbinder et al. | |
| 10,328,130 B2 | 6/2019 | Frost et al. | |

(Continued)

FOREIGN PATENT DOCUMENTS

| | | |
|---|---|---|
| CN | 101970650 A | 2/2011 |
| CN | 102065886 A | 5/2011 |

(Continued)

OTHER PUBLICATIONS

PDF NCBI Reference Sequence : NP_001166492.1 (downloaded Aug. 24, 2023). (Year: 2023).*
Lin et al., "Molecular cloning of the human and monkey sperm surface protein PH-20", Proc. Natl. Aca. Sci. Vol. 90, pp. 10071-10075 (Nov. 1993).*
NCBI, "NCBI Reference Sequence: XP_011728213.1haluronidase PH-20 [Macaca nemestrina]", Apr. 24, 2018.
Arming, S., et al., "In Vitro Mutagenesis of PH-20 Hyaluronidase from Human Sperm", "Eur. J. Biochem.", 1997, pp. 810-814, vol. 247.
Bookbinder, L.H., et al., "A Recombinant Human Enzyme for Enhanced Interstitial Transport of Therapeutics", "Journal of Controlled Release", 2006, pp. 230-241, vol. 114.

(Continued)

*Primary Examiner* — Anand U Desai
(74) *Attorney, Agent, or Firm* — Sughrue Mion, PLLC

(57) ABSTRACT

The present invention is related to the field of protein engineering technology which increases the enzymatic activity and thermal stability of human hyaluronidase which is an enzyme that hydrolyzes hyaluronic acid; and more particularly to hyaluronidase PH20 variants or fragments thereof, which comprise one or more amino acid residue substitutions in the region corresponding to the alpha-helix region and its linker region in the amino acid sequence of wild-type PH20 of SEQ ID NO: 1 and in which one or more amino acid residues at the N-terminus and/or the C-terminus are selectively cleaved additionally.
Specifically, the present invention relates to PH20 variants or fragments thereof, which comprise one or more amino acid residue substitutions selected from the group consisting of T341A, T341C, T341G, S343E, M345T, K349E, L353A, L354I, N356E and I361T in wild-type PH20 having the amino acid sequence of SEQ ID NO: 1, and additionally comprise the substitution of amino acids located in the alpha-helix 8 region and/or a linker region between alpha-helix 7 and alpha-helix 8 in the amino acid sequence of wild-type PH20, and in which one or more amino acids located at the N-terminal and C-terminal regions are deleted.

49 Claims, 15 Drawing Sheets

Specification includes a Sequence Listing.

(56) References Cited

U.S. PATENT DOCUMENTS

| | | |
|---|---|---|
| 10,865,400 B2 | 12/2020 | Wei et al. |
| 10,898,551 B2 | 1/2021 | Bookbinder et al. |
| 10,918,736 B2 | 2/2021 | Kim et al. |
| 11,041,149 B2 | 6/2021 | Wei et al. |
| 11,066,656 B2 | 7/2021 | Wei et al. |
| 11,723,959 B2 | 8/2023 | Bookbinder et al. |
| 11,952,600 B2 | 4/2024 | Wei et al. |
| 12,091,692 B2 | 9/2024 | Wei et al. |
| 12,104,185 B2 | 10/2024 | Wei et al. |
| 2006/0104968 A1 | 5/2006 | Bookbinder et al. |
| 2009/0123367 A1 | 5/2009 | Bookbinder et al. |
| 2010/0003238 A1 | 1/2010 | Frost et al. |
| 2010/0143457 A1 | 6/2010 | Wei et al. |
| 2010/0305500 A1 | 12/2010 | Lambert et al. |
| 2011/0044977 A1 | 2/2011 | Adler |
| 2012/0148535 A1 | 6/2012 | Carrio et al. |
| 2013/0101577 A9 | 4/2013 | Wei et al. |
| 2013/0302275 A1 | 11/2013 | Wei et al. |
| 2014/0037613 A1 | 2/2014 | Bookbinder et al. |
| 2014/0199282 A1 | 7/2014 | Bookbinder et al. |
| 2015/0001529 A1 | 1/2015 | Kurokawa |
| 2015/0010529 A1 | 1/2015 | Wei |
| 2015/0165059 A1 | 6/2015 | Bookbinder et al. |
| 2016/0362670 A1 | 12/2016 | Wei et al. |
| 2017/0089914 A1 | 3/2017 | Loo et al. |
| 2017/0218069 A1 | 8/2017 | Rosengren et al. |
| 2017/0218382 A1 | 8/2017 | Kondo |
| 2018/0044419 A9 | 2/2018 | Rosengren et al. |
| 2018/0185506 A1 | 7/2018 | Bookbinder et al. |
| 2018/0250397 A1 | 9/2018 | Benyunes et al. |
| 2019/0046657 A1 | 2/2019 | Kim et al. |
| 2021/0155913 A1 | 5/2021 | Park |
| 2021/0363270 A1* | 11/2021 | Park .................. A61K 47/26 |
| 2022/0089738 A1 | 3/2022 | Krishnamachari et al. |
| 2022/0289864 A1* | 9/2022 | Park .................. A61K 9/0019 |
| 2022/0031093 A1 | 10/2022 | Park et al. |
| 2023/0174963 A1 | 6/2023 | Park et al. |
| 2023/0250408 A1 | 8/2023 | Park et al. |
| 2023/0321203 A1 | 10/2023 | Bookbinder et al. |
| 2023/0365692 A1 | 11/2023 | Krishnamachari et al. |

FOREIGN PATENT DOCUMENTS

| | | |
|---|---|---|
| CN | 102307993 A | 1/2012 |
| CN | 103173474 A | 6/2013 |
| CN | 104244968 A | 12/2014 |
| CN | 104745553 A | 7/2015 |
| CN | 105567606 A | 5/2016 |
| CN | 110494450 A | 11/2019 |
| CN | 111971387 A | 11/2023 |
| CO | 2021011944 A2 | 9/2021 |
| EA | 022752 B1 | 2/2016 |
| EP | 2 405 015 A2 | 1/2012 |
| EP | 2662090 A1 | 11/2013 |
| EP | 2 674 487 A1 | 12/2013 |
| EP | 1858926 B1 | 10/2015 |
| EP | 3037529 A1 | 6/2016 |
| EP | 3 045 472 A1 | 7/2016 |
| EP | 2797622 B1 | 10/2016 |
| EP | 3 186 281 B1 | 4/2019 |
| EP | 3130347 B1 | 9/2019 |
| EP | 3636752 A1 | 4/2020 |
| EP | 3785701 A1 | 3/2021 |
| ES | 2573462 T3 | 6/2016 |
| JP | 2009515521 A | 4/2009 |
| JP | 2011512844 A | 4/2011 |
| JP | 2015504666 A | 2/2015 |
| JP | 2020500863 A | 1/2020 |
| JP | H7166478 B2 | 11/2022 |
| KR | 1020120094493 A | 8/2012 |
| KR | 1020120105426 A | 9/2012 |
| KR | 101233457 B1 | 2/2013 |
| KR | 1020130116386 A | 10/2013 |
| KR | 101363658 B1 | 2/2014 |
| KR | 1020140021046 A | 2/2014 |
| KR | 101493644 B1 | 2/2015 |
| KR | 101546563 B1 | 8/2015 |
| KR | 1020160052812 A | 5/2016 |
| KR | 101647932 B1 | 8/2016 |
| KR | 10-2017-0065032 | 6/2017 |
| KR | 101874401 B1 | 7/2018 |
| KR | 1020200017538 A | 2/2020 |
| KR | 1020200130451 A | 11/2020 |
| KR | 1020100135291 A | 12/2020 |
| KR | 10-2021-0023798 A | 3/2021 |
| KR | 10-2022-0069045 | 5/2022 |
| TW | 201534726 A | 9/2015 |
| TW | 202140780 A | 11/2021 |
| WO | 2004078140 A2 | 9/2004 |
| WO | 2007064437 A2 | 6/2007 |
| WO | 2009065507 A2 | 5/2009 |
| WO | 2009117085 A1 | 9/2009 |
| WO | 2009128917 A2 | 10/2009 |
| WO | 2010077297 A1 | 7/2010 |
| WO | 2011012637 A2 | 2/2011 |
| WO | 2011029892 A2 | 3/2011 |
| WO | 2012135408 A1 | 10/2012 |
| WO | 2013102144 A2 | 7/2013 |
| WO | 2015003167 A1 | 1/2015 |
| WO | 2015071366 A1 | 5/2015 |
| WO | 2015/095418 A1 | 6/2015 |
| WO | 2016033555 A1 | 3/2016 |
| WO | 2017004706 A1 | 1/2017 |
| WO | 2017079150 A1 | 5/2017 |
| WO | 2017131496 A1 | 8/2017 |
| WO | 2018102372 A1 | 6/2018 |
| WO | 2018183928 A1 | 10/2018 |
| WO | 2018204368 A1 | 11/2018 |
| WO | 2018222722 A2 | 12/2018 |
| WO | 2019222435 A1 | 11/2019 |
| WO | 2020022791 A1 | 1/2020 |
| WO | 2020197230 A1 | 1/2020 |
| WO | 2020172621 A1 | 8/2020 |
| WO | 2021150079 A1 | 7/2021 |
| WO | 2022031093 A1 | 10/2022 |
| WO | 2023075506 A1 | 5/2023 |

OTHER PUBLICATIONS

Chao, K., et al., "Structure of Human Hyaluronidase-1, a Hyaluronan Hydrolyzing Enzyme Involved in Tumor Growth and Angiogenesis", "Biochemistry", 2007, pp. 6911-6920, vol. 46.

Frost, G. I., "Recombinant Human Hyaluronidase (rHuPH20): an Enabling Platform for Subcutaneous Drug and Fluid Administration", "Expert Opinion Drug Delivery", 2007, pp. 427-440, vol. 4, No. 4.

Shpilberg, O., et al., "Subcutaneous administration of rituximab MabThera and trastuzumab Herceptin using hyaluronidase", British Journal of Cancer, 2013, pp. 1556-1561, vol. 109.

Stern, R., et al., "Mammalian Hyaluronidases", Glycoforum, 2000, pp. 1-6, vol. 4.

Stern, R., et al., "Hyaluronidases: Their Genomics, Structures, and Mechanisms of Action", Chem Rev, 2006, pp. 818-839, vol. 106, Publisher: American Chemical Society.

Stern, R., et al., "Supplementary Data: Hyaluronidases: Their Genomics, Structures, and Mechanisms of Action", Chem Rev, 2006, pp. 818-839, vol. 106, Publisher: American Chemical Society.

Thomas, J.R., et al., "The INFUSE Morphine Study: Use of Recombinant Human Hyaluronidase rHuPH20 to Enhance the Absorption of Subcutaneously Administered Morphine in Patients with Advanced Illness", Journal of Pain and Symptom Management, 2009, pp. 673-682, vol. 38, No. 5, Publisher: Elsevier.

Wang, W, et al., "Antibody Structure, Instability, and Formulation", Journal of Pharmaceutical Sciences, DOI: 10.1002/jps.20727, 2007, vol. 96, No. 1, Publisher: Wiley InterScience.

Bittner, B., et al., "Subcutaneous Administration of Biotherapeutics An Overview of Current Challenges and Opportunities", BioDrugs, 2018, pp. 425-440, vol. 32, Publisher: CrossMark.

Borders, C.L., et al., "Purification and Partial Characterization of Testicular Hyaluronidase", The Journal of Biological Chemistry, 1968, pp. 3756-3762, vol. 243, No. 13.

(56) References Cited

OTHER PUBLICATIONS

Chen, K-J, et al., "Constitutive expression of recombinant human hyaluronidase PH20 by Pichia pastoris", Journal of Bioscience and Bioengineering, 2016, pp. 673-678, vol. 122, Publisher: Elsevier.
Opposition filed Jan. 13, 2022 by Laboratorios Legrand S.A. against Columbian Patent Application No. NC2021/0012380, in Spanish.
English Translation of Opposition filed Jan. 13, 2022 by Laboratorios Legrand S.A. against Columbian Patent Application No. NC20210012380.
Opposition dated Jul. 5, 2022 by Asociacion de Laboratorios Farmaceuticos (ALAFAR) Against Ecuadorian Application No. SENADI-2021-70640, in Spanish.
English Translation of Opposition dated Jul. 5, 2022 by Asociacion de Laboratorios Farmaceuticos (ALAFAR) Against Ecuadorian Application No. SENADI-2021-70640.
Frost, G.I, et al., "A Microtiter-Based Assay for Hyaluronidase Activity Not Requiring Specialized Reagents", Analytical Biochemistry, 1997, pp. 263-269, vol. 251, Publisher: Academic Press.
Hofinger, E.SA, et al., "Kinetics of Hyal 1 and PH 20 hyaluronidases: Comparison of minimal substrates and analysis of the transglycosylation reaction", Blycobiology, 2007, pp. 963-971, vol. 17, No. 9.
Markovic Housley, Z., et al., "Crystal Structure of Hyaluronidase, a Major Allergen of Bee Venom", Structure, 2000, pp. 1025-1035, vol. 8, Publisher: Elsevier.
Kreidieh, F.Y., et al., "Overview prevention and management of chemotherapy extravasation", World Journal of Clinical Oncology, 2016, pp. 87-97, vol. 7, No. 1.
Mcatee, C.O., et al., "Emerging roles for hyaluronidase in cancer metastasis and therapy", Advance in Cancer Research, 2014, pp. 1-23, vol. 123, Publisher: HHS Public Access.
Messina, L., et al., "Identification and characterization of a bacterial hyaluronidase and its production in recombinant form", FEBS Letters, 2016, pp. 2180-2189, vol. 590, Publisher: FEB Press.
Muller, S., et al., "Spliceosomal Peptide P140 for Immunotherapy of Systemic Lupus Erythematosus", Arthritis & Rheumatism, 2008, pp. 3873-3883, vol. 58, No. 12.
English Translation of International Search Report and Written Opinion for International Patent Application No. PCT/KR20/03975.
International Search Report Mailed Oct. 29, 2019 for PCT Application No. PCT/KR19/09215.
JP2022211105—Notice of Reasons for Refusal mailed on Nov. 14, 2023, 17 pages.
CN201980023392.4—First Office Action mailed on Jun. 17, 2023, 9 pages.
KR20207002955—Written Decision on Registration mailed on Aug. 25, 2020, 16 pages.
JP2020500863—Notice of Reasons for Refusal mailed on Jan. 25, 2022, 7 pages.
JP2020500863—Notice of Reasons for Refusal mailed on May 24, 2022, 6 pages.
JP2020500863—Notice of Reasons for Refusal mailed on Jun. 15, 2021, 12 pages.
EP19827585—Supplementary European search report mailed on Mar. 31, 2021, 9 pages.
JP2022211105—Decision of Rejection mailed on May 14, 2024, 2 pages.
CA3,093,885—Examiner Requisition mailed on Sep. 1, 2021, 4 pages.
CA3,093,885—Examiner Requisition mailed on Oct. 3, 2022, 6 pages.
AU2019311658—Examination Report No. 1 mailed on Jun. 17, 2022, 3 pages.
AU2019311658—Notice of Acceptance mailed on Oct. 11, 2022, 3 pages.
U.S. Appl. No. 17/608,729—Requirement for Restriction/Election mailed on May 14, 2024, 5 pages.
KR20227013211—Request for the Submission of an Opinion mailed on Apr. 26, 2024, 7 pages.
CN202180003323.4—First Office Action mailed on Nov. 27, 2023, 14 pages.
EP21743774—Supplementary European search report mailed on Jan. 4, 2023, 20 pages.
JP2021567961—Decision of Rejection mailed on Nov. 14, 2023, 8 pages.
JP2021567961—Notice of Reasons for Refusal mailed on Apr. 11, 2023, 6 pages.
AU2021211348—Examination Report No. 1 mailed on Mar. 17, 2023, 3 pages.
AU2021211348—Examination Report No. 2 mailed on Jul. 11, 2023, 5 pages.
AU2021211348—Notice of Acceptance mailed on Sep. 21, 2023, 4 pages.
CA3,137,324—Examiner Requisition mailed on Dec. 2, 2022, 4 pages.
CA3,137,324—Examiner Requisition mailed on May 6, 2024, 6 pages.
KR20207030248—Written Decision on Registration mailed on Dec. 22, 2023, 5 pages.
KR20207030248—Notice of Final Rejection mailed on Jul. 27, 2023, 6 pages.
KR20207030248—Request for the Submission of an Opinion mailed on Aug. 28, 2022, 14 pages.
KR20227016935—Written Decision on Registration mailed on Dec. 21, 2022, 6 pages.
JP2022068166—Notice of Reasons for Refusal mailed on Jun. 21, 2022, 8 pages.
JP2022068166—Decision to Grant a Patent mailed on Oct. 4, 2022, 5 pages.
JP2020569741—Notice of Reasons for Refusal mailed on Nov. 16, 2021, 8 pages.
JP2020569741—Decision to Grant a Patent mailed on May 16, 2023, 5 pages.
CN202310416462.0—Notification of grant of patent right for invention mailed on May 16, 2024, 3 pages.
AU2020248612—Examination Report No. 3 mailed on Nov. 8, 2023, 2 pages.
AU2020248612—Examination Report No. 2 mailed on Oct. 25, 2023, 3 pages.
CA3131052—Office Action mailed on May 6, 2024, 5 pages.
EP20776465.5—Extended European search report mailed on Feb. 11, 2022, 15 pages.
KR20210103530—Request for the Submission of an Opinion mailed on Sep. 19, 2023, 7 pages.
RU2022125351—Office Action mailed on Nov. 2, 2023, 15 pages.
International Search Report and Written Opinion dated Nov. 18, 2021 in International Application No. PCT/KR2021/010368, pp. 17.
RU2021132331—Office Action mailed on Nov. 3, 2023, 16 pages.
Appendix A Sequence Alignment, 2024, 2 pages.
AU2020248612—Notice of Acceptance mailed on Sep. 21, 2023, 4 pages.
JP2022211105—Decision of Dismissal of Amendment mailed on May 14, 2024, 4 pages.
JP2021567961—Office Action mailed on Jul. 2, 2024, 6 pages.
CN202180003323.4—First Office Action mailed on Jul. 10, 2024, 12 pages.
Tavares, A. et al., "Inhibition of the checkpoint protein PD-1 by the therapeutic antibody pembrolizumab outlined by quantum chemistry", Scientific Reports, 2018, vol. 8, Issue 1840, pp. 1-13.
CONC20210012380—Office Action mailed on Jan. 11, 2024, 16 pages.
EA202192588—Office Action mailed on Sep. 29, 2023, 8 pages.
IDP00202108509—Office Action mailed on Sep. 27, 2023, 4 pages.
PA93644-01—Search Report mailed on Mar. 29, 2022, 8 pages.
JP2023026863—Notice of Reasons for Refusal mailed on Mar. 12, 2024, 10 pages.
CN202080003052.8—First Office Action mailed on Jun. 27, 2023, 12 pages.
CN202080003052.8—Second Office Action mailed on Mar. 2, 2024, 11 pages.
CN202310416462.0—First Office Action mailed on Mar. 5, 2024, 8 pages.
EESR Issued in counterpart European Patent Application No. 21743774.8 on Jan. 4, 2023, 20 pages.

(56) References Cited

OTHER PUBLICATIONS

Seffernick, J.L., et al., "Melamine Deaminase and Atrazine Chlorohydrolase: 98 Percent Identical but Functionally Different", Journal of Bacteriology, 2001, vol. 183, No. 8, Publisher: American Society for Microbiology, 2405-2410 pages.
Locke, K.W., et al., "ENHANZE drug delivery technology: a novel approach to subcutaneous administration using recombinant human hyaluronidase PH20", Drug Delivery, 2019, DOI:10.1080/10717544. 2018.1551442, vol. 26, No. 1, Publisher: Taylor & Francis, 98-106 pages.
Muchmore, D.B., et al., "Accelerating and Improving the Consistency of Rapid-Acting Analog Insulin Absorption and Action for Both Subcutaneous Injection and Continuous Subcutaneous Infusion Using Recombinant Human Hyaluronidase", Journal of Diabetes Sciene and Technology, 2012, vol. 6, No. 4, Publisher: Diabetes Technology Societ, 764-772 pages.
Restelli, V., et al., "The Effect of Dissolved Oxygen on the Production and the Glycosylation Profile of Recombinant Human Erythropoietin Produced From CHO Cells", Biotechnol Bioeng, 2006, vol. 9, 481-494 pages.
Schilling, S., et al., "Heterologous Expression and Characterization of Human Glutaminy Cyclase: Evidence for a Disulfide Bond with Importance for Catalytic Activity", Biochemistry, 2002, vol. 41, Publisher: American Chemical Society, 10849-10857 pages.
CA3173310—Office action mailed on Dec. 20, 2023, 5 pages.
CN202180030097.9—First Office Action mailed on Jan. 6, 2024, 19 pages.
JP2022559471—Final Notification of Reasons forRefusal mailed on Mar. 19, 2024, 8 pages.
KR1020210103530—Written Decision on Registration mailed on Dec. 15, 2023, 6 pages.
Zarrintaj et al., "Poloxamer: A versatile tri-block copolymer for biomedical applications", Acta Biomaterialia, 2020, vol. 110, 37-67 pages.
Strickley et al., "A review of formulations of commercially available antibodies", Journal of Pharmaceutical Sciences, 2021, vol. 110, 2590-2608 pages.
International Search Report dated Feb. 2, 2023 in International Application No. PCT/KR2022/016709, 14 pages.
CN201980023392.4—Second Office Action mailed on Feb. 8, 2024, 8 pages.
Office Action Issued in Japanese Patent Application No. 2022559471 on Oct. 11, 2023, 15 pages.
Chica et al., "Semi-rational approaches to engineering enzyme activity: combining the benefits of directed evolution and rational design" Current Opinion Biotechnology, vol. 16, Issue 4, 2005, 378-784 pages.
Wasserman, R.L., "Overview of recombinant human hyaluronidase-faciliated subcutaneous infusion of IgG in primary immunodeficiencies", Immunotherapy, 2014, vol. 6, No. 5, Publisher: Future Medicin, 553-567 pages.
Hiromoto, Y., et al., "An Activity-Straining Method on Filtration Paper Enables High-Throughput Screening of Temperature-Sensitive and Inactive Mutations of Rice-Amylase for Improvement of Rice Grain Quality", Plant and Cell Physiology, 2017 vol. 58, No. 4, Publisher: Japanese Society of Plant Physiologists, , 658-667 pages.
Chen, K., et al., "Constitutive Expression of Recombinant Human Hyaluronidase PH20 by Pichia Pastoris", "Journal of Bioscience and Bioengineering", 2016, 1-6 pages.
Office Action issued in Korean Patent Application No. 20227016935 on Aug. 28, 2022, 20 pages.
Office Action issued in Japanese Patent Application No. 2020569741 on Aug. 23, 2022, 5 pages.
Office Action issued in Canadian Patent Application No. 3131052 on Oct. 19, 2022, 6 pages.
Office Action issued in Australian Patent Application No. 2020248612 on Nov. 8, 2022, 3 pages.

Takahashi, T. et al., "A fluorimetric Morgan-Elson assay method for hyaluronidase activity," Analytical Biochemistry, 2003, vol. 322, 257-263 pages.
John S Philo, "A Critical Review of Methods for Size Characterization of Non-Particulate Protein Aggregates," Current Pharmaceutical Biotechnology, Jul. 2009, vol. 10, 359-372 pages.
Lafaro et al., "The Paradoxical Web of Pancreatic Cancer Tumor Microenvironment", The American Journal of Pathology, vol. 189, No. 1, Jan. 2019, 44-57 pages.
Schon, et al., "Denatured state aggregation parameters derived from concentration dependence of protein stability", Analytical Biochemistry, 2015, vol. 488, 45-50 pages.
NCBI Genbank Accession No. AAC60607.2, Jun. 5, 2000, 1 page.
U.S. Appl. No. 17/052,952—Non-Final Office Action mailed on Dec. 12, 2023, 32 pages.
International Search Report and Written Opinion mailed Jul. 29, 2021 for International Patent Application No. PCT/KR2021/000943 filed Mar. 24, 2020, 21 pages.
International Search Report and Written Opinion mailed Jun. 30, 2020 for International Patent Application No. PCT/KR2020/003975 filed Mar. 24, 2020, 23 pages.
The abstract of Alley et al., Journal of Thoracic Oncology, 2018, vol. 12, No. 1S, S294, Abstract No. OA13.03, 1 page.
U.S. Appl. No. 17/907,538—Requirement for Restriction/Election mailed on May 12, 2023, 5 pages.
U.S. Appl. No. 17/907,538—Non-Final Office Action mailed on Aug. 3, 2023, 10 pages.
U.S. Appl. No. 17/907,538—Ex Parte Quayle Action mailed on Feb. 15, 2024, 4 pages.
U.S. Appl. No. 17/907,538—Notice of Allowance mailed on Apr. 24, 2024, 7 pages.
CA3137324—Office Action mailed on May 6, 2024, 6 pages.
Chan et al., "Therapeutic antibodies for autoimmunity and inflammation", Nature Reviews Immunology, vol. 10, May 2010, pp. 301-316.
Liu, "Pharmacokinetics of monoclonal antibodies and Fc-fusion proteins", Protein Cell, 2018, vol. 9, No. 1, pp. 15-32.
NCBI Reference Sequence: NP 001166492.1, hyaluronidase PH-20 precursor [Cavia porcelius], Jun. 21, 2021, pp. 2.
NCBI Reference Sequence: NP 001166492.1, hyaluronidase PH-20 precursor [Cavia porcelius], Jun. 19, 2020, pp. 2.
Office Action issued in Chile Patent Application No. 202102464 with English Translation on May 4, 2023, pp. 23.
Opposition filed against Ecuador Patent Application SENADI-2021-70640 with English Translation on Feb. 14, 2022, p. 217. English Translation on Apr. 3, 2023,.
Office Action issued in Georgian Patent Application No. AP202015767 with pp. 9.
Office Action issued in Saudia Arabia Patent Application No. 521430398 with English Translation on Feb. 25, 2023, pp. 11.
Opposition by Laboratorios Legrand S.A. Against Columbian Patent Application NC20210012380 with English Translation Oct. 20, 2021, pp. 21.
Office Action issued on Dec. 2, 2022 in counterpart Canadian Patent Application No. 2137324, pp. 4.
Office Action issued on Oct. 17, 2022 in counterpart Russian Patent Application No. 2021132331, pp. 18.
Office Action issued on Sep. 5, 2022 in counterpart Taiwan Patent Application 110130965, pp. 6.
Harb, G., et al., "Safety and pharmakokinetics of subcutaneous ceftriaxone administered with or without recombinant human hyaluronidase (rHuPH20) versus intravenous ceftriaxone administration in adult volunteers", Current Medical Research & Opinion, 2010, vol. 26, No. 2, Publisher: CMRO, pp. 279-288.
Broun, P., et al., "Catalytic Plasticity of Fatty Acid Modification Enzymes Underlying Chemical Diversity of Plant D Lipids", Science, 1998, pp. 1315-1317, vol. 282, No. 13, Publisher: www.sciencemag.org.
Harris, R.J., et al., "Commercial Manufacturing Scale Formulation and Analytical Characterization of Therapeutic Recombinant Antibodies", Drug Development Research, 2004, vol. 61, pp. 137-154.

(56) References Cited

OTHER PUBLICATIONS

Krantz, E.M., "Low-Dose Intramuscular Ketamine and Hyaluronidase for Induction of Anaesthesia in NonPemedicated Children", S.A. Med. J., 1980, vol. 58, No. 4, pp. 161-162.
Whisstock, J.D., et al., "Prediction of protein function from protein sequence and structure", Quarterly Reviews of Biophysics, 2003, vol. 36, No. 3, Publisher: Cambridge University Press, pp. 307-340.
Pakula, A., et al., "Genetic Analysis of Protein Stability and Function", Annu. Rev. Genet., 1898, vol. 23, pp. 289-310.
Witkowski, A., et al., "Conversion of a Beta-Ketoacyl Synthase to a Malonyl Decarboxylase by Replacement of the Active-Site Cysteine with Glutamine", Biochemistry, 1999, vol. 38, Publisher: American Chemical Society, pp. 11643-11650.
"GenBank: AAC6067.2, PH-20 (Homo sapiens)", NCBI, Jun. 5, 2000, pp. 2.
Singh et al., "Protein Engineering Approaches in the Post-Genomic Era", Current Protein and Peptide Science, 2017, vol. 18, pp. 1-11.
Tachibana, H., et al., "Changes of monosacharide availability of human hybridoma lead to alteration of biological properties of human monoclonal antibody", Cytotechnology, 1994, vol. 16, Publisher: Kiuwer Academic Publishers, pp. 151-157.
Borys, M.C., et al., "Culture pH Affects Expression Rates and Glycosylation of Recombinant Mouse Placental Lactogen Proteins by Chinese Hamster Ovary (CHO) Cells", Biotechnology, 1993, vol. 11, Publisher: Nature Publishing Group, pp. 720-724.
Borys, M.C., et al., "Ammonia Affects the Glycosylation Patterns of Recombinant Mouse Placental Lactogen-l by Chinese Hamster Overy Cells in a pH-Dependent Manner", Biotechnology and Bioengineering, 1994, vol. 43, Publisher: John Wiley & Sons, Inc., pp. 505-514.
Clark, K.J.R., et al., "Temperature Effects on Product-Quality-Related Enzymes in Batch CHO Cell Cultures Producing Recombinant tPA", Biotechnol. Prog., 2004, pp. 1888-1892, vol. 20, Publisher: American Chemical Society.
Clement, Wa, et al., "The use of hyaluronidase in nasal infiltration: prospective randomized controlled pilot study", The Journal of Laryngology & Otology, 2003, vol. 117, pp. 614-618.
H. Johansen, et al., "High-level production of fully active human alpha 1-antitrypsin in *Escherichia coli*." Mol. Biol. Med. (1987) vol. 4, pp. 291-305.
J.H. Dunham, et al., "GPR37 Surface Expression Enhancement via N-Terminal Truncation or Protein-Protein Interactions", Biochemistry (2009) 48, pp. 10286-10297.
M. Wei, et al., "N-terminal truncations on L1 proteins of human papillomaviruses promote their soluble expression in *Escherichia coli* and self-assembly in vitro", Emerging Microbes & Infections (2018) vol. 7, pp. 160.
M. F. Meyer, et al., "The soluble hyaluronidase from bull testes is a fragment of the membrane-bound PH-20 enzyme", FEBS letter (1997) vol. 413, pp. 385-388.
International Search Report and Written Opinion dated Sep. 21, 2023 in International Application No. PCT/KR2023/008621, 15 pages.
CN201980023392.4—Decision of Final Rejection mailed on May 17, 2024, 10 pages.
CA3,093,885—Office Action mailed on Jun. 3, 2024, 4 pages.
JP2022-211105—Decision of Rejection mailed on May 14, 2024, 3 pages.
U.S. Appl. No. 17/052,952—Non-Final Office Action mailed on Jun. 13, 2024, 20 pages.
AU2021320569—Examination Report No. 1 mailed on Apr. 30, 2024, 3 pages.
CN2021800300979—First Office Action mailed on Jan. 16, 2024, 18 pages.
MX/a/2020/009824—Office Action mailed on Jun. 10, 2024, 22 pages.
TW111145281—First Office Action mailed on May 29, 2024, 16 pages.
Bazhenova et al., Cancer Research, vol. 77, No. 13, suppl. Abstract No. CT032.
TW111128188—First Office Action mailed on May 29, 2024, 24 pages.
TW110102662—Office Action mailed on May 3, 2024, 22 pages.
TW111136059—Office Action mailed on May 3, 2024, 20 pages.
VN1-2021-06635—Office Action mailed on Feb. 26, 2024, 4 pages.
Office Action dated Jul. 9, 2021 in Taiwanese Patent Application No. 109119328.
JP2023026863—Decision of Refusal mailed on Oct. 8, 2024, 4 pages.
KR20207024813—Request for the Submission of an Opinion mailed on Jul. 30, 2024, 14 pages.
EP21853474.1—Extended European search report mailed on Jul. 31, 2024, 14 pages.
Butler M., "Optimisation of the Cellular Metabolism of Glycosylation for Recombinant Proteins Produced by Mammalian Cell Systems", Cytotechnology, vol. 50, No. 1-3, Jun. 9, 2006, pp. 57-76.
Hossler et al., "Optimal and consistent protein glycosylation in mammalian cell culture", Glycobiology, vol. 19, No. 9, Jun. 3, 2009, pp. 936-949.
JP2021-567961—Decision to Grant a Patent mailed on Oct. 8, 2024, 7 pages.
TW110102662—Second Office Action mailed on Sep. 5, 2024, 6 pages.
TW111136059—Second Office Action mailed on Sep. 5, 2024, 6 pages.
TW112123526—Second Office Action mailed on Sep. 6, 2024, 6 pages.
AU2023200324—Examination Report No. 1 mailed on Aug. 22, 2024, 2 pages.
EP20776465.5—Communication pursuant to 94(3) EPC mailed on Jul. 16, 2024, 7 pages.
KR20240036308—Written Decision on Registration mailed on Sep. 2, 2024, 6 pages.
BR1120200190411—Office Action mailed on Oct. 15, 2024, 8 pages.
AU2021320569—Notice of Acceptance mailed on Sep. 20, 2024, 4 pages.
CN202180030097.9—Second Office Action mailed on Oct. 13, 2024.
U.S. Appl. No. 16/628,258—Notice of Allowance mailed on Aug. 16, 2024, 8 pages.
Petition for Post Grant Review filed Nov. 12, 2024 in Case No. PGR2025-00003, U.S. Pat. No. 11,952,600.
File History of U.S. Pat. No. 11,952,600.
Declaration of Michael Hecht, Ph.D. Executed Nov. 12, 2024, Case No. PGR2025-00003, U.S. Pat. No. 11,952,600 (Exhibit 1003 in PGR2025-00003).
Declaration of Dr. Sheldon Park Executed Nov. 8, 2024, Case No. PGR2025-00003, U.S. Pat. No. 11,952,600 (Exhibit 1004 in PGR2025-00003).
Stern et al., "The Hyaluronidases: Their Genomics, Structures, and Mechanisms of Action," Chem. Rev. 106:818-839 (2006).
Jedzrejas et al., "Structures of Vertebrate Hyaluronidases and Their Unique Enzymatic Mechanism of Hydrolysis," Proteins: Structure, Function and Bioinformatics, 61:227-238 (2005).
Zhang et al., "Hyaluronidase Activity of Human Hyal1 Requires Active Site Acidic and Tyrosine Residues," J. Biol. Chem., 284(14): 9433-9442 (2009).
Bordoli et al., "Protein structure homology modeling using SwissModel workspace," Nature Protocols, 4(1):1-13 (2008).
Brandon & Tooze, "Introduction to Protein Structure," Second Ed., Chapters 1-6, 11-12, 17-18 (1999).
Table Associating Citations from the U.S. Pat. No. 11,952,600 Patent (Exhibit 1001 in PGR2025-00003) to Corresponding Citations in U.S. Appl. No. 13/694,731 Application (Exhibit 1026 in PGR2025-00003).
Steipe, "Consensus-Based Engineering of Protein Stability: From Intrabodies to Thermostable Enzymes," Methods in Enzymology, 388:176-186 (2004).
Green, "Computer Graphics, Homology Modeling, and Bioinformatics," Protein Eng'g & Design, Ch. 10, 223-237 (2010).

(56) References Cited

OTHER PUBLICATIONS

Hardy et al., "Assessment of contraceptive vaccines based on recombinant mouse sperm protein PH20," Reprod., 127:325-334 (2004).
Pomering et al., "Restricted Entry of IgG into Male and Female Rabbit Reproductive Ducts Following Immunization with Recombinant Rabbit PH-20," Am. J. Reprod. Immunol., (3):174-82 (2002).
Baba et al., "Mouse Sperm Lacking Cell Surface Hyaluronidase PH-20 Can Pass through the Layer of Cumulus Cells and Fertilize the Egg," J. Biol. Chem., 277(33):30310-4 (2002).
Primakoff et al., "Reversible Contraceptive Effect of PH-20 Immunization in Male Guinea Pigs," Biol Reprod., 56(5):1142-6 (1997).
Tung et al., "Mechanism of Infertility in Male Guinea Pigs Immunized with Sperm PH-20," Biol. Reprod., 56(5):1133-41 (1997).
Rosengren et al., "Recombinant Human PH20: Baseline Analysis of the Reactive Antibody Prevalence in the General Population Using Healthy Subjects," BioDrugs, 32(1):83-89 (2018).
U.S. Appl. No. 13/694,731.
Gmachl et al., "The human sperm protein PH-20 has hyaluronidase activity," FEBS Letters, 3:545-548 (1993).
Sills, "Retraction," Science, 319:569 (2008).
Yue et al., "Loss of Protein Structure Stability as a Major Causative Factor in Monogenic Disease," J. Mol. Biol., 353:459-473 (2005).
Wang & Moult "SNPs, Protein Structure, and Disease," Hum. Mutation, 17:263-270 (2001).
"Negative Results," Nature: Editorials, 453:258 (2008).
Lins et al., "Analysis of Accessible Surface of Residues in Proteins," Protein Sci., 12:1406-1417 (2003).
Hayden, "Chemistry: Designer Debacle," Nature, 453:275-278 (2008).
Benkert et al., "Toward the Estimation of the Absolute Quality of Individual Protein Structure Models," Bioinformatics, 27:343-350 (2010).
Schwede et al., "SWISS-MODEL: An Automated Protein Homology-Modeling Server," Nucleic Acids Rsch., 31:3381-3385 (2003).
Alberts, "Molecular Biology of the Cell," Fifth Edition, Chapter 3 (2007).
He et al., "NMR Structures of Two Designed Proteins with High Sequence Identity but Different Fold and Function," PNAS, 105:14412-14417 (2008).
Alexander et al., "A Minimal Sequence Code for Switching Protein Structure and Function," PNAS, 106:21149-21154 (2009).
Ruan et al., "Design and Characterization of a Protein Fold Switching Network," Nature Comm., 14 (2023).
Sievers et al., "Fast, Scalable Generation of High-Quality Protein Multiple Sequence Alignments Using Clustal Omega," Molecular Sys. Biology, 7.1 (2011).
Mihel, "PSAIA—Protein Structure and Interaction Analyzer," BMC Structural Biology, 8:21 (2008).
Redline Comparison of U.S. Appl. No. 13/694,731 application Exhibit 1026 in PGR2025-00003) and U.S. Pat. No. 11,952,600 Patent (Exhibit 1001 in PGR2025-00003) Specifications.
Beasley & Hecht, "Protein Design: The Choice of de Novo Sequences," J. Biological Chemistry, 272:2031-2034 (1997).
Xiong et al., "Periodicity of Polar and Nonpolar Amino Acids is the Major Determinant of Secondary Structure in Self-Assembling Oligomeric Peptides," PNAS, 92: 6349-6353 (1995).
Hayden, "Key Protein-Design Papers Challenged," Nature, 461:859 (2009).
Kegg, Drug: Hyaluronidase (human recombinant), available at: https://www.genome.jp/entry/D06604, accessed Oct. 5, 2024.
Pace & Scholtz, "A Helix Propensity Scale Based on Experimental Studies of Peptides and Proteins," Biophysical J. 75:422-427 (1998).
U.S. Appl. No. 61/631,313.
U.S. Appl. No. 61/796,208.
Hom_pre2011 (Exhibit 1053 in PGR2025-00003).
Hom_pre2011_header (Exhibit 1054 in PGR2025-00003).
Hom_pre2011_header_clean (Exhibit 1055 in PGR2025-00003).
Hom_pre2011.fasta (Exhibit 1056 in PGR2025-00003).
Ph20_pre2011.aln-clustal_num (Exhibit 1057 in PGR2025-00003).
Ph20_pre2011 Alignment html (Exhibit 1058 in PGR2025-00003).
Leisola & Turenen, "Protein Engineering: Opportunities and Challenges," Appl. Microbiol. Biotechnol. 75:1225-1232 (2007).
Hecht et al., "De Novo Proteins from Designed Combinatorial Libraries," Protein Sci., 13:1711-1723 (2004).
Rosengren et al., "Clinical Immunogenicity of rHuPH20, a Hyaluronidase Enabling Subcutaneous Drug Administration," Aaps J., 17:1144-1156 (2015).
Collection of BLAST Webpages from the Internet Archive, navigable from: https://web.archive.org/web/20111022151531/http://www.clustal.org/omega/.
Collection of Clustal Omega Webpages from the Internet Archive, navigable from: https://web.archive.org/web/20111022151531/http://www.clustal.org/omega/, accessed Nov. 9, 2024.
Collection of Swiss-Model Webpages from the Internet Archive, navigable from: https://web.archive.org/web/20110519141121/http://swissmodel.expasy.org/?pid=smh01&uid=&token=, accessed Nov. 9, 2024.
Collection of PyMol Webpages from the Internet Archive, navigable from: https://web.archive.org/web/20110701072314/http://pymol.org/, accessed Nov. 7, 2024.
Declaration of Jeffrey P. Kushan dated Nov. 12, 2024, Case No. PGR2025-00003 U.S. Pat. No. 11,952,600 (Exhibit 1068 in PGR2025-00003).
Swiss Model Printout of PH20 Model, printed Nov. 10, 2024 (Exhibit 1069 in PGR2025-00003).
Swiss Model Printout of PH20 Model with D320K Mutation, printed Nov. 9, 2024 (Exhibit 1070 in PGR2025-00003).
Swiss Model Printout of PH20 Model with D320H Mutation, printed Nov. 9, 2024 (Exhibit 1071 in PGR2025-00003).
Swiss Model Printout of PH20 Model with D320R Mutation, printed Nov. 9, 2024 (Exhibit 1072 in PGR2025-00003).
Swiss Model Printout of PH20 Model with D320S Mutation, printed Nov. 9, 2024 (Exhibit 1073 in PGR2025-00003).

* cited by examiner

【Fig. 1】
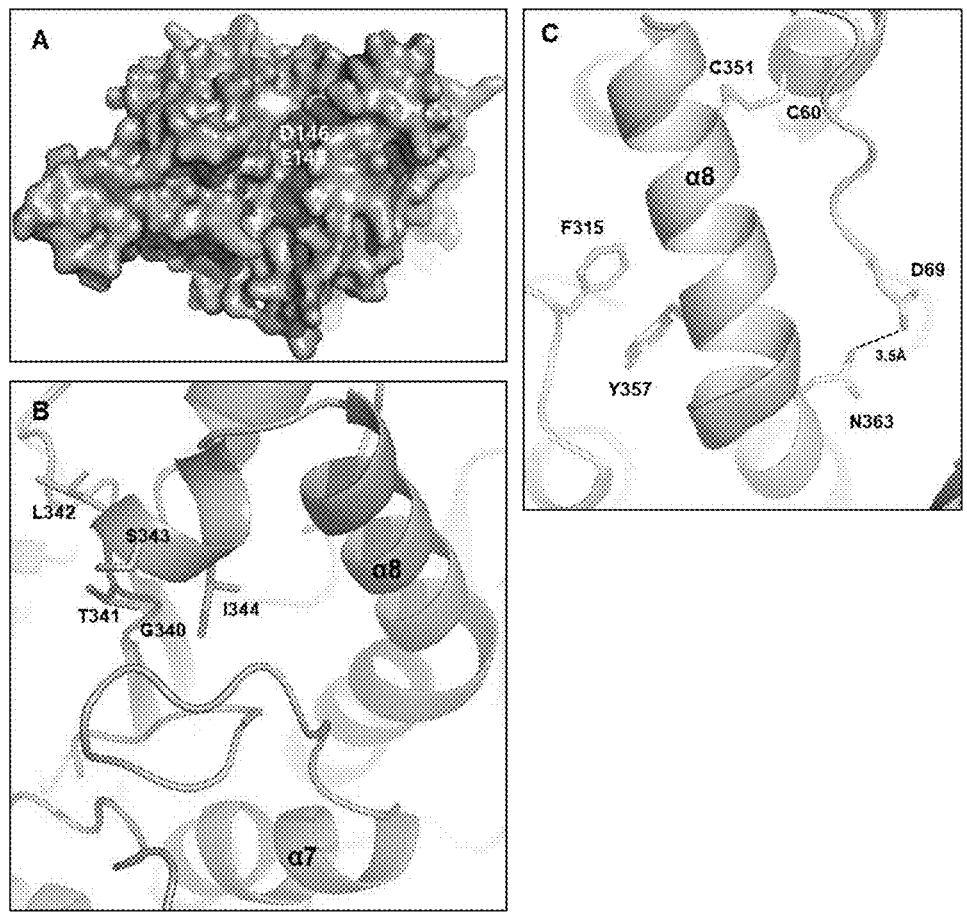
【Fig. 2】
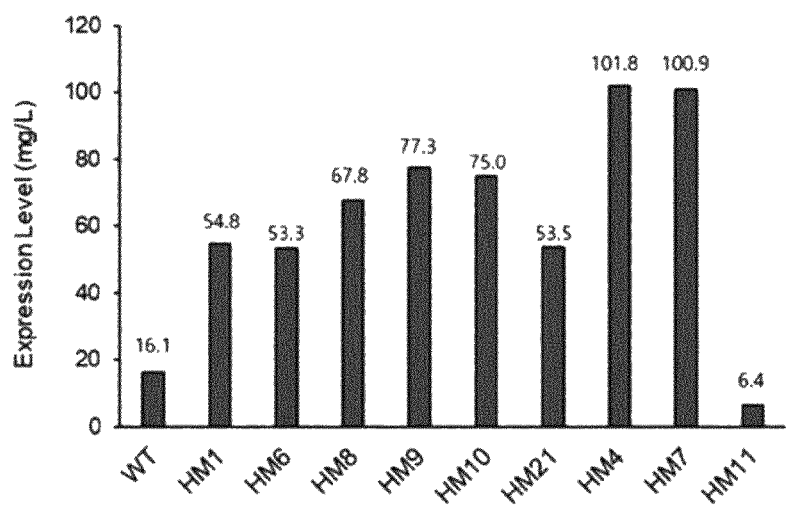

[Fig. 3]
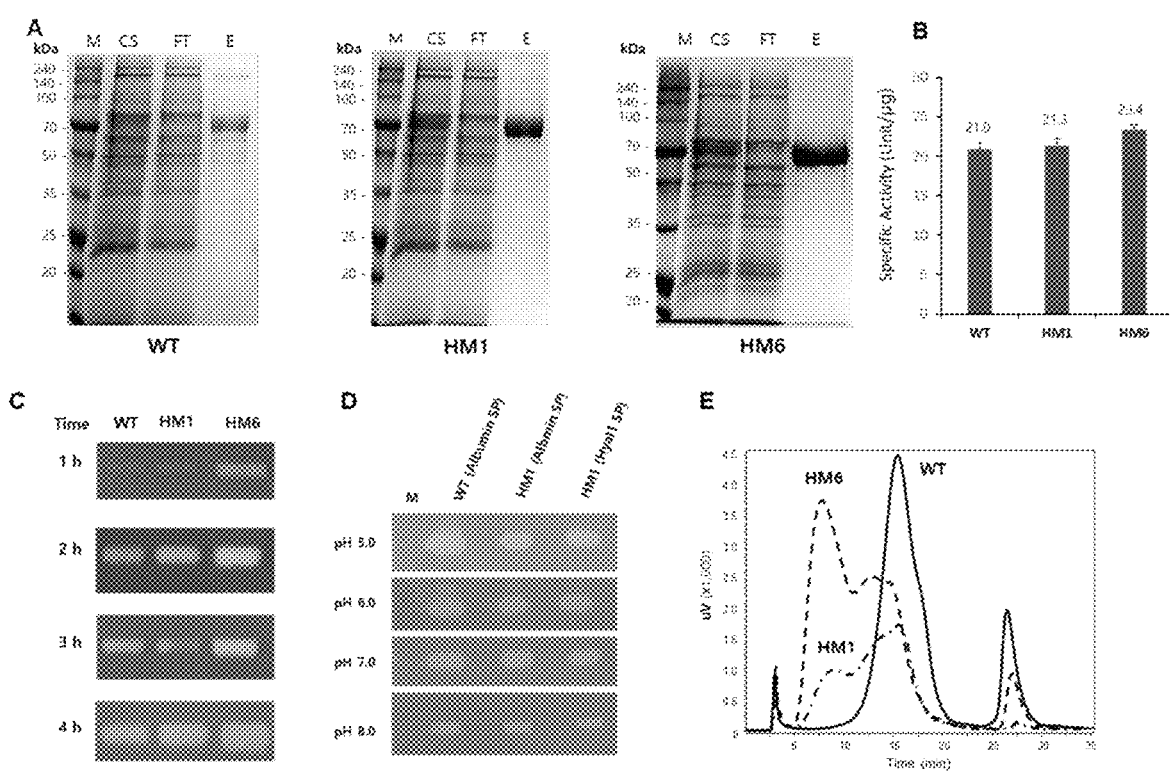

[Fig. 4]
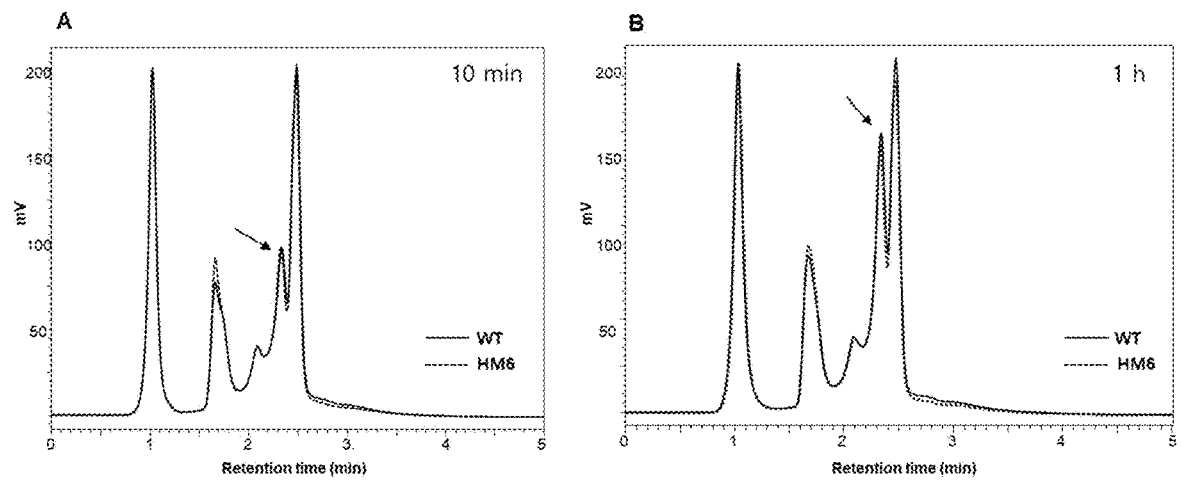
[Fig. 5]
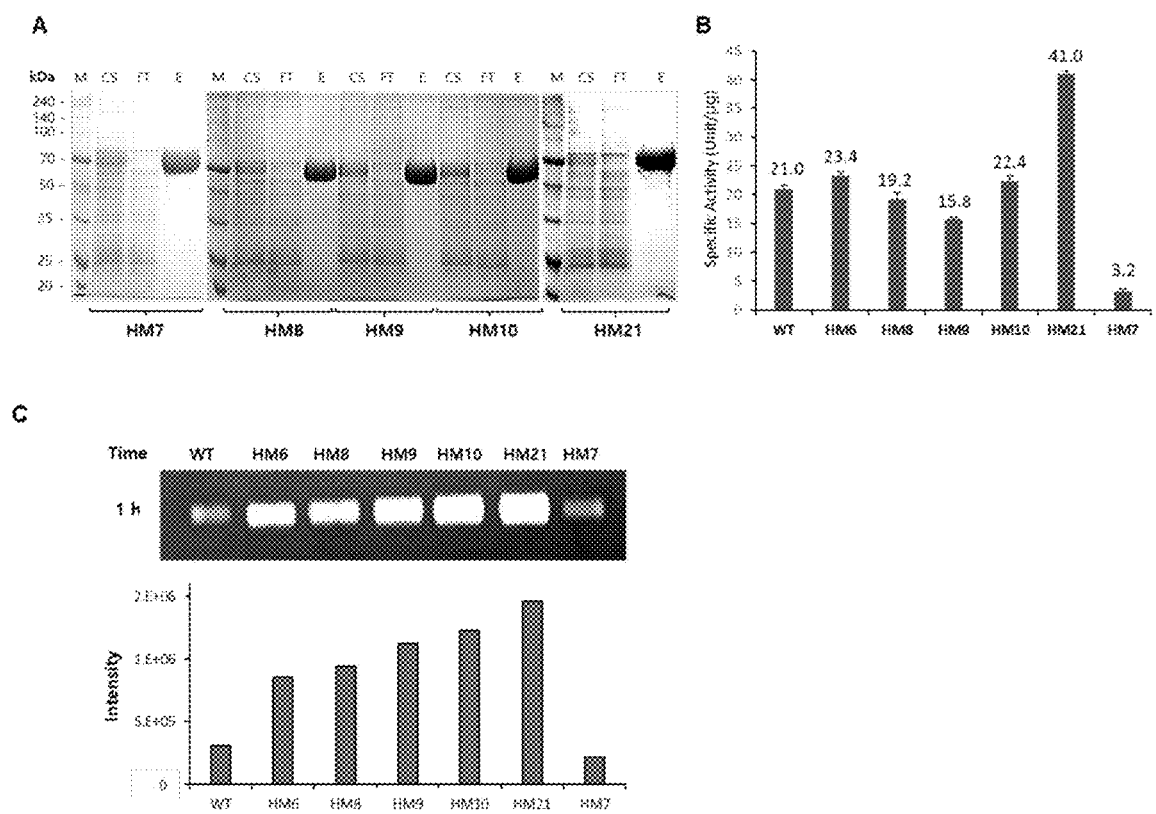

[Fig. 6]
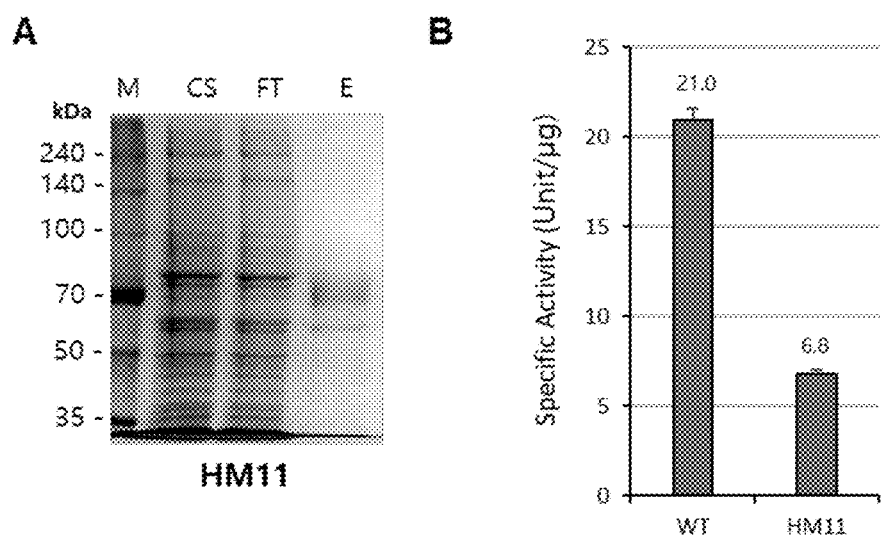

[Fig. 7]
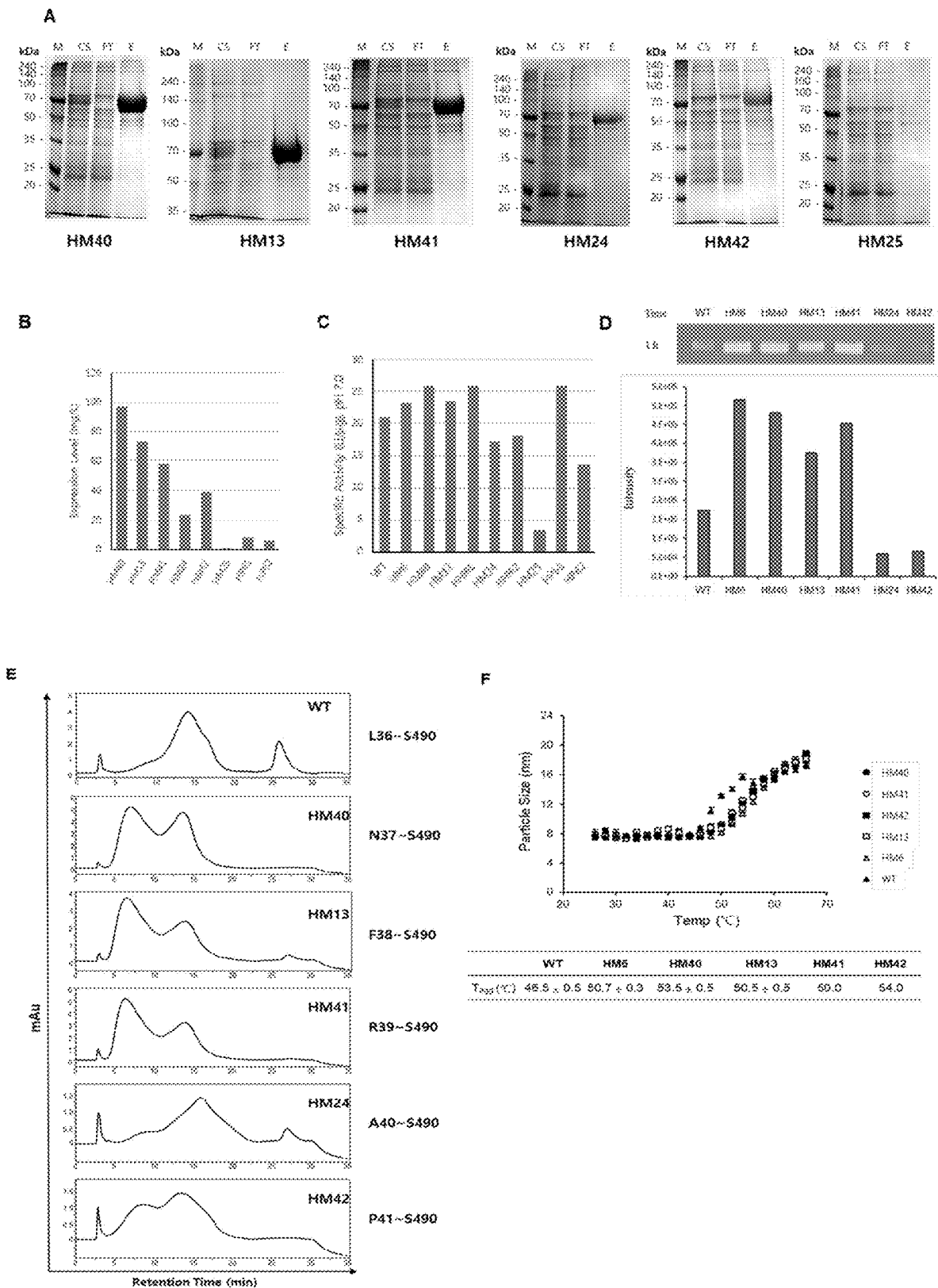

[Fig. 8]
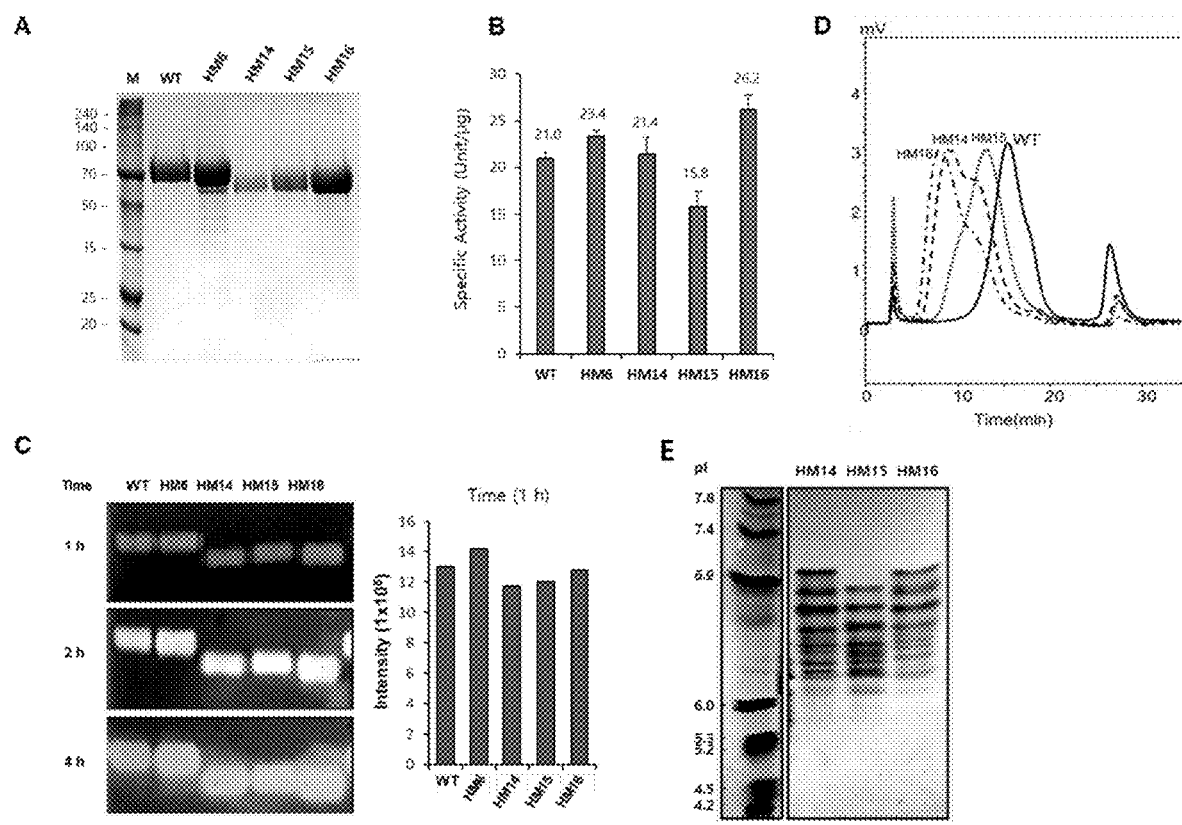

[Fig. 9]
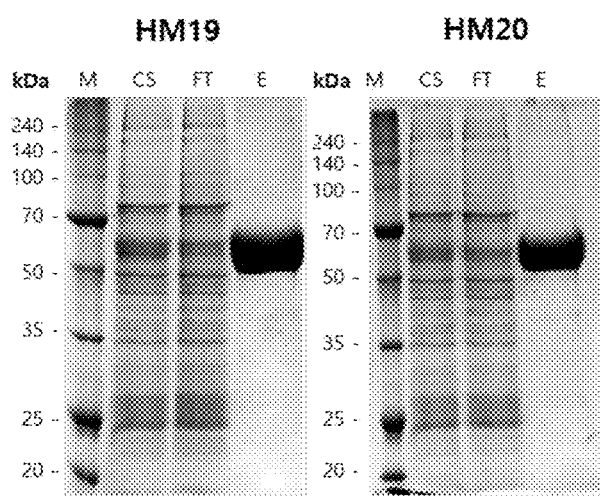
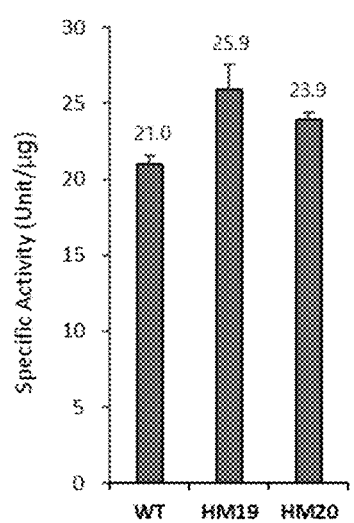
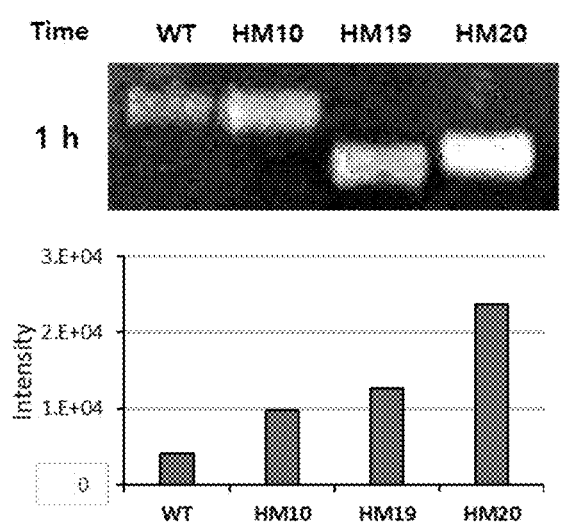

[Fig. 10]

|  | $T_{agg.}$ (°C) |
|---|---|
| WT | 46.5 ± 0.5 |
| HM1 | 53.0 ± 1.2 |
| HM4 | 56.5 ± 1.5 |
| HM6 | 50.5 ± 0.5 |
| HM7 | 58.0 ± 1.0 |
| HM8 | 52.5 ± 0.5 |
| HM9 | 53.0 ± 1.0 |
| HM10 | 55.5 ± 0.5 |
| HM13 | 50.5 ± 0.5 |
| HM14 | 51.0 ± 1.0 |
| HM15 | 49.0 ± 1.0 |
| HM16 | 51.0 ± 1.0 |
| HM19 | 53.0 ± 1.0 |
| HM20 | 51.0 ± 1.0 |
| HM21 | 51.7 ± 0.7 |

[Fig. 11]
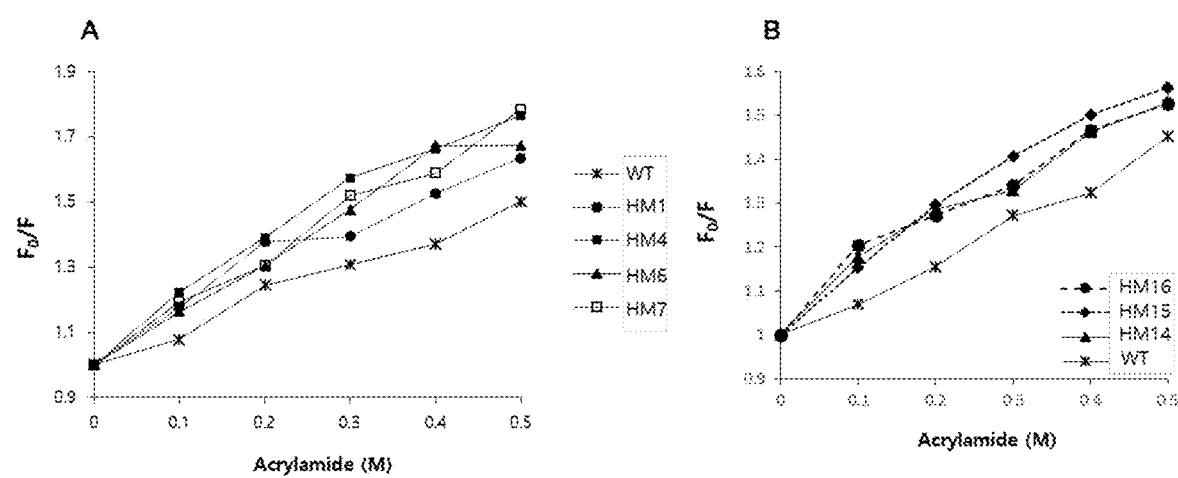

[Fig. 12]
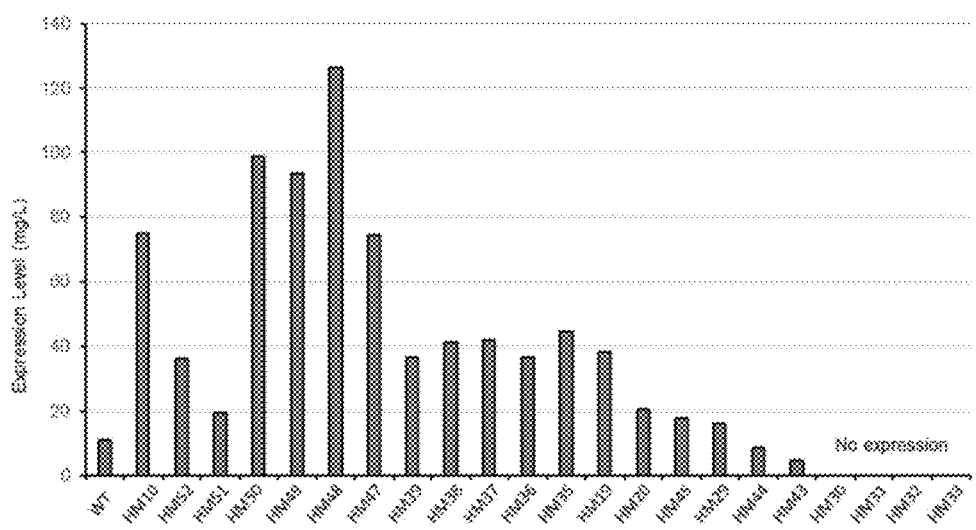
| | Total length | Expression level (mg/L) | | Total length | Expression level (mg/L) | | Total length | Expression level (mg/L) |
|---|---|---|---|---|---|---|---|---|
| WT | L36~S490 | 16.1 | HM39 | F38~E476 | 36.7 | HM29 | L36~A467 | 16.3 |
| HM10 | L36~S490 | 75.0 | HM38 | F38~T475 | 41.4 | HM44 | F38~D466 | 8.5 |
| HM52 | F38~T488 | 36.2 | HM37 | F38~E474 | 41.9 | HM43 | F38~I465 | 4.7 |
| HM51 | F38~P486 | 19.7 | HM36 | F38~M473 | 36.6 | HM30 | L36~C464 | No |
| HM50 | F38~A484 | 98.9 | HM35 | F38~P472 | 44.8 | HM31 | L36~D461 | No |
| HM49 | F38~Y482 | 93.4 | HM19 | F38~K470 | 38.3 | HM32 | L36~C458 | No |
| HM48 | F38~I480 | 126.5 | HM20 | F38~F468 | 20.8 | HM33 | L36~V455 | No |
| HM47 | F38~P478 | 74.4 | HM45 | F38~A467 | 17.9 | | | |

【Fig. 13】
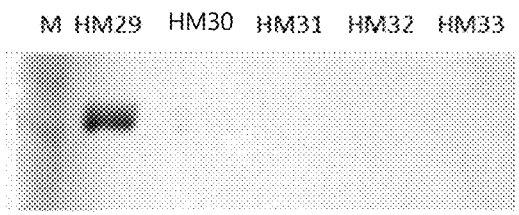
【Fig. 14】
A
| | C-term residue number | Specific activity (U/μg), pH 7.0 | | C-term residue number | Specific activity (U/μg), pH 7.0 |
|---|---|---|---|---|---|
| WT | 490 | 22.3 ± 0.4 | HM36 | 473 | 22.0 ± 0.3 |
| HM10 | 490 | 21.7 ± 0.6 | HM35 | 472 | 23.3 ± 0.2 |
| HM52 | 488 | 29.5 ± 1.9 | HM19 | 470 | 25.9 ± 1.6 |
| HM51 | 486 | 27.5 ± 1.8 | HP19 | 470 | 19.9 ± 0.6 |
| HM50 | 484 | 28.5 ± 2.4 | HM20 | 468 | 23.9 ± 0.5 |
| HM49 | 482 | 29.3 ± 1.7 | HP20 | 468 | 21.6 ± 0.6 |
| HM48 | 480 | 29.9 ± 0.7 | HM45 | 467 | 18.0 ± 2.5 |
| HM47 | 478 | 17.8 ± 0.3 | HM29 | 467 | 18.2 ± 0.2 |
| HM39 | 476 | 20.4 ± 0.2 | HM44 | 466 | 23.2 ± 0.2 |
| HM38 | 475 | 22.3 ± 0.4 | HM43 | 465 | 19.1 |
| HM37 | 474 | 21.8 ± 0.5 | | | |
B 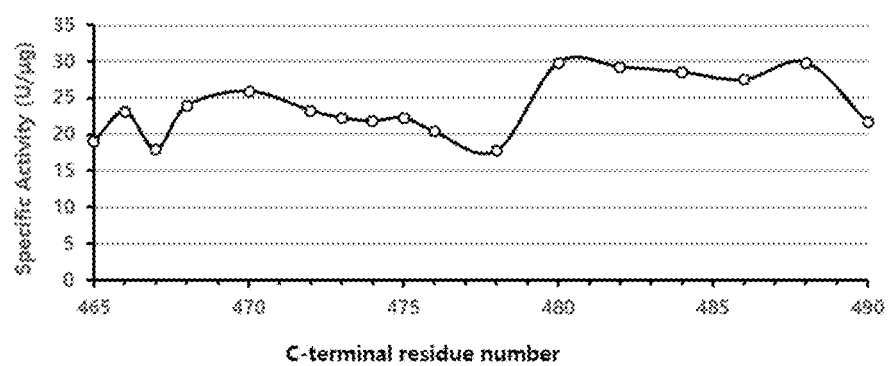
C 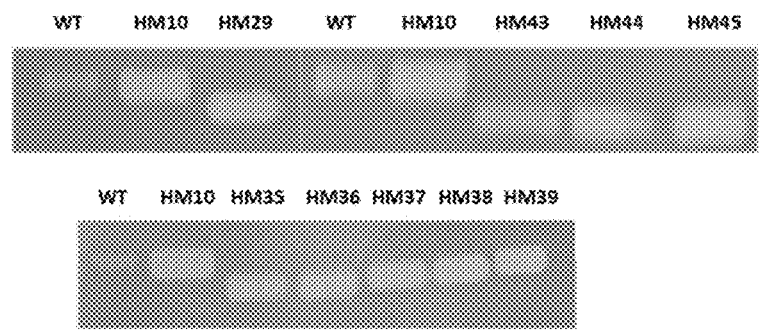

[Fig. 15]
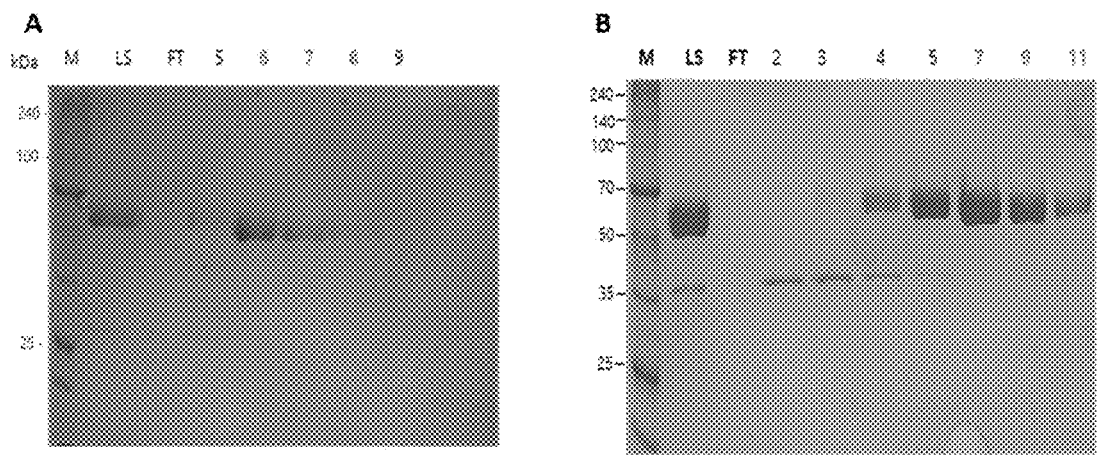
[Fig. 16]
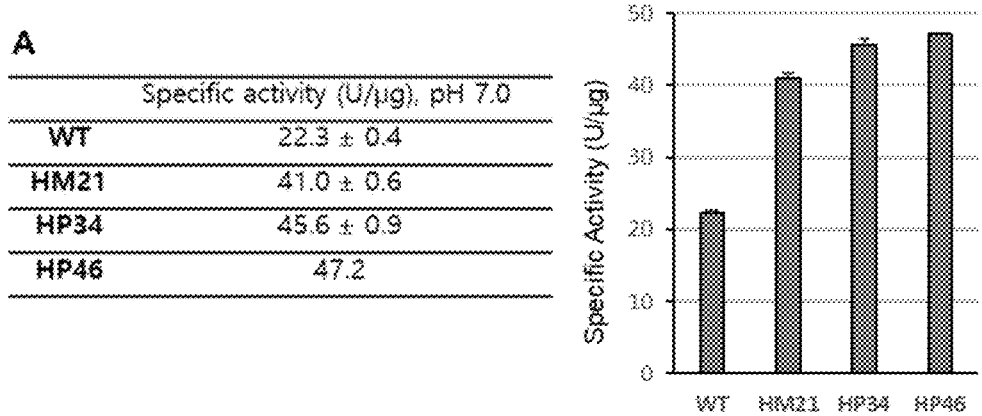

[Fig. 17]
A
|  | $T_{agg}$ (°C) |
|---|---|
| HW2 | 46.5 |
| HM21 | 51.7 |
| HP34 | 51.5 |
| HP46 | 51.0 |
B
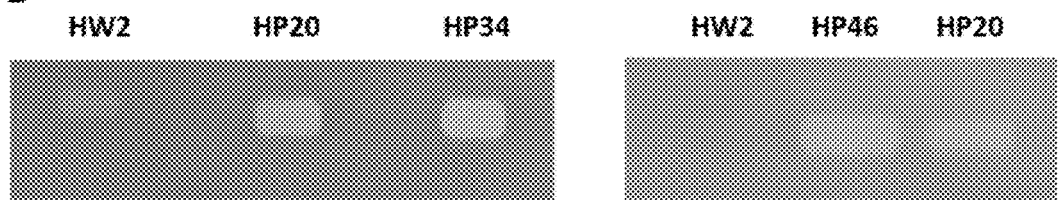
C
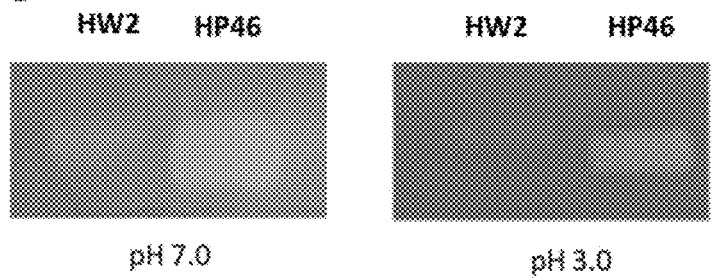
D 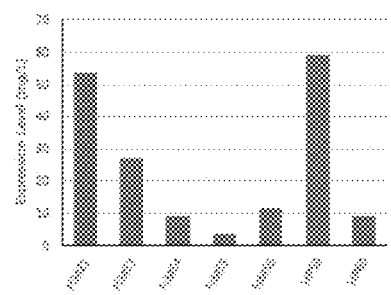 E 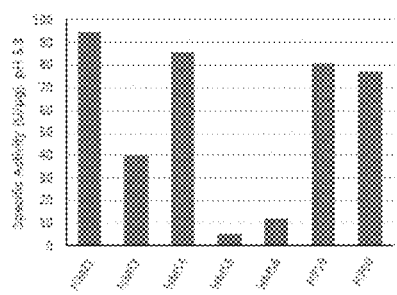

[Fig. 18]
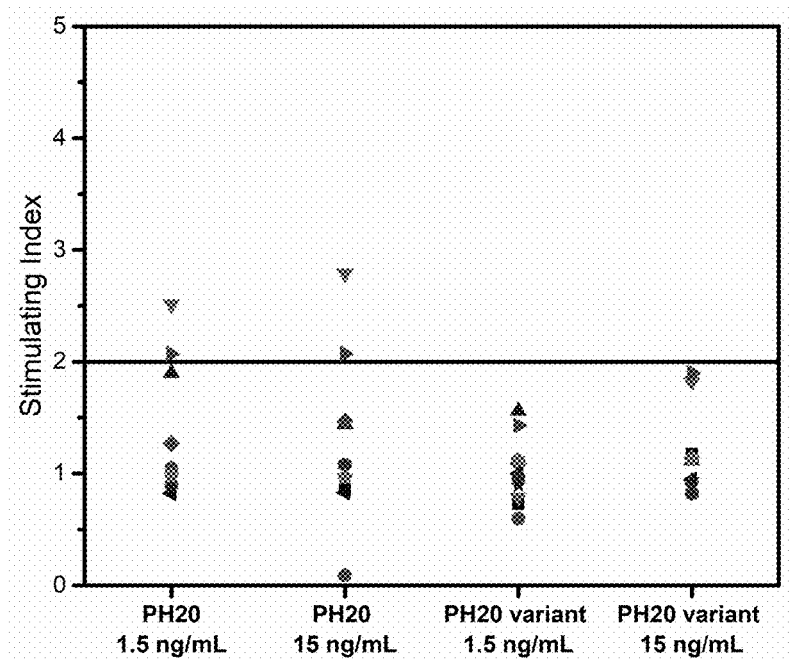
[Fig. 19]
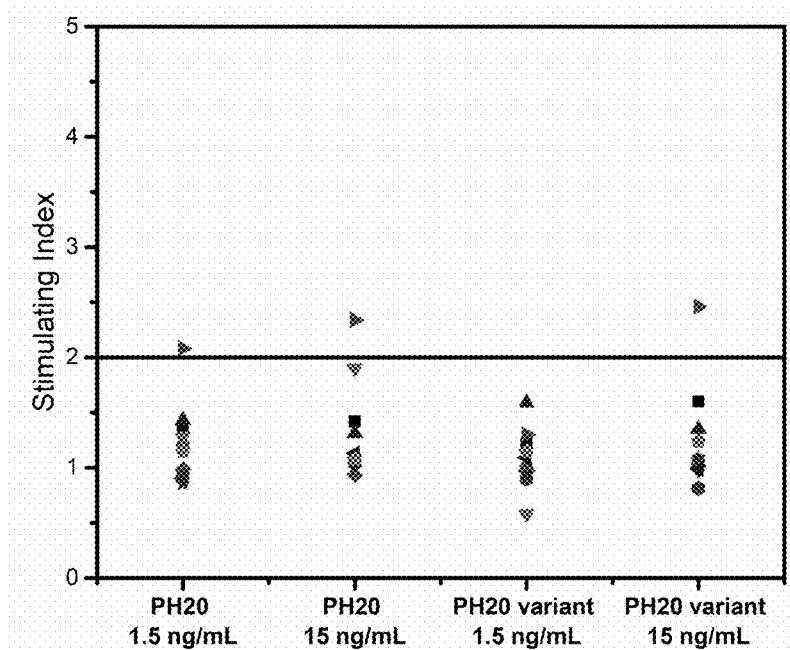

HYALURONIDASE VARIANTS AND PHARMACEUTICAL COMPOSITION COMPRISING THE SAME

CROSS-REFERENCE TO RELATED APPLICATIONS

This application is a U.S. national phase under the provisions of 35 U.S.C. § 371 of International Patent Application No. PCT/KR19/09215 filed Jul. 25, 2019, which in turn claims priority under 35 U.S.C. § 119 of Korean Patent Application No. 10-2018-0086308 filed Jul. 25, 2018 and priority under 35 U.S.C. § 119 of Korean Patent Application No. 10-2019-0029758 filed Mar. 15, 2019. The disclosures of such international patent application and Korean priority patent applications are hereby incorporated herein by reference in their respective entireties, for all purposes.

INCORPORATION BY REFERENCE OF SEQUENCE LISTING

The content of the electronically submitted sequence listing, file name: Q303380 Sub SeqListing ST25.txt; size: 233.6 KB; and date of creation: May 29, 2025, filed herewith, is incorporated herein by reference in its entirety.

TECHNICAL FIELD

The present invention relates to novel human hyaluronidase variants having increased enzymatic activity and thermal stability compared to human hyaluronidase which is an enzyme that hydrolyzes hyaluronic acid, and more particularly to hyaluronidase PH20 variants or fragments thereof, which comprise one or more amino acid residue substitutions in the region corresponding to the alpha-helix region and/or its linker region in wild-type PH20 having the amino acid sequence of SEQ ID NO: 1, preferably mature wild-type PH20 consisting of amino acid residues L36 to S490, and in which portion(s) of the N-terminal and/or C-terminal amino acid residues are selectively deleted, a method for producing the same, and a pharmaceutical composition comprising the same.

BACKGROUND ART

The human skin is composed of epidermis, dermis and a subcutaneous fat layer, and there are six types of glycosaminoglycans in the skin. These glycosaminoglycans include hyaluronic acid, chondroitin sulfate, dermatan sulfate, heparan sulfate, heparin, and keratin sulfate.

These glycosaminoglycans are composed of repeating disaccharide sugar units. The number of the disaccharide sugar units is different among the glycosaminoglycans, but ranges from several hundreds to thousands. Among the glycosaminoglycans, hyaluronic acid is present in the skin more than half of the amount in the body. Hyaluronic acid is synthesized by hyaluronan synthase present in the cell membrane, is present alone without binding to proteoglycans, and is the only glycosaminoglycan having no sulfate group. Other glycosaminoglycans bind to proteoglycans and have a sulfate group. Hyaluronic acid consists of glucuronic acid and N-acetylglucosamine linked via β-1,3 bonds, and is composed of about 5,000 repeating units of these disaccharides. N-acetylglucosamine and glucuronic acid are linked via β-1,4 bonds. It is known that about one-third (5 g) of hyaluronic acid in the human body is turned over every day.

Hyaluronidases are enzymes that degrade hyaluronic acid present in the extracellular matrix. It is known that there are six types of hyaluronidases in humans: They are Hyal1, Hyal2, Hyal3, Hyal4, HyalPS1, and PH20/SPAM1. Human Hyal1 and Hyal2 are expressed in most of the tissues. PH20/SPAM1 (hereinafter referred to as PH20) is expressed in the sperm plasma membrane and the acrosomal membrane. However, HyalPS1 is not expressed because it is a pseudogene. Hyaluronidases are divided into, according to a method of cleaving hyaluronic acid, three types: enzymes (EC 3.2.1.35) that cleave β-1,4 bonds between N-acetylglucosamine and glucuronic acid by the use of $H_2O$; enzymes (EC 3.2.1.36) that cleave β-1,3 bonds between N-acetylglucosamine and glucuronic acid by the use of $H_2O$; and bacterial hyaluronidases (EC 4.2.99.1) that cleave β-1,4 bonds without using $H_2O$.

The catalytic amino acids of Hyal1 are D129 and E131, which hydrolyze hyaluronic acid by substrate-assisted catalysis. Hyal1 exhibits the optimum activity at an acidic pH of 3 to 4, and has no enzymatic activity at pH 4.5 or higher. In contrast to Hyal1, PH20 exhibits enzymatic activity at a wide pH range of 3 to 8.

Arming et al. identified that the catalytic amino acids of PH20 are D111 and E113 (Arming et al., 1997). Arming et al. labelled Leu, the first amino acid of PH20 from which the signal sequence was removed, as position 1, and thus the catalytic amino acid residues of the full-length PH20 included in the signal sequence correspond to D146 and E148, respectively.

Hyaluronidase hydrolyzes hyaluronic acid, thereby reducing the viscosity of hyaluronic acid in the extracellular matrix and increasing the permeability thereof into tissue (skin). The subcutaneous area of the skin has a neutral pH of about 7.0 to 7.5. Thus, among the various types of hyaluronidases, PH20 is widely used in clinical practice (Bookbinder et al., 2006). In examples in which PH20 is used in clinical practice, PH20 is used as an eye relaxant and an anesthetic injection additive in ophthalmic surgery, and is also co-administered with an antibody therapeutic agent which is injected subcutaneously (Bookbinder et al., 2006). In addition, based on the property of hyaluronic acid that is overexpressed in tumor cells, PH20 is used to hydrolyze hyaluronic acid in the extracellular matrix of tumor cells, thereby increasing the access of an anticancer therapeutic agent to the tumor cells. In addition, it is also used to promote resorption of body fluids and blood, which are excessively present in tissue.

PH20 was first identified in guinea pig sperm by Lathrop et al. and is also known to be expressed in sperms of different species. Human PH20 gene was cloned by Lin et al. and Gmachl et al. Human PH20 has the amino acid sequence of SEQ ID NO: 1 which consists of 509 amino acid residues, and exhibits 60% amino acid identity with guinea pig PH20. Human PH20 enzyme is encoded from SPAM1 (sperm adhesion molecule-1) gene, and Ser490 of PH20 is present as binding to the glycosylphosphatidylinositol (GPI) on the surface of the sperm plasma membrane and in the acrosomal membrane. Sperm hydrolyzes hyaluronic acid using PH20 when it penetrates oocytes through the hyaluronan-rich cumulus layer of the oocytes. PH20 is present in the amount corresponding to 1% or less of the amount of proteins in sperm, and has six N-glycosylation sites (N82, N166, N235, N254, N368, and N393).

Currently commercially available PH20 is obtained by extraction from the testes of cattle or sheep. Examples thereof include Amphadase® (bovine hyaluronidase) and Vitrase® (sheep hyaluronidase).

Bovine testicular hyaluronidase (BTH) is obtained by removing a signal peptide and 56 amino acids on the C-terminal from bovine wild-type PH20 during post-translational modification. BTH is also a glycoprotein, and has a mannose content of 5% and a glucosamine content of 2.2%, based on the total components including amino acids. When animal-derived hyaluronidase is repeatedly administered to the human body at a high dose, a neutralizing antibody can be produced. Since animal-derived hyaluronidase contains other biomaterials in addition to PH20, it may cause an allergic reaction when administered to the human body (Bookbinder et al., 2006). In particular, the production and the use of PH20 extracted from cattle can be limited due to concerns of mad cow disease. In order to overcome this problem, studies on the recombinant protein of human PH20 have been conducted.

Recombinant protein of human PH20 has been reported to be expressed in yeast (*P. pastoris*), DS-2 insect cells, and animal cells. The recombinant PH20 proteins produced in insect cells and yeast differ from human PH20 in terms of the pattern of N-glycosylation during post-translational modification.

Among hyaluronidases, protein structures of Hyal1 (PDB ID: 2PE4) (Chao et al., 2007) and bee venom hyaluronidase (PDB ID: 1FCQ, 1FCU, 1FCV) are determined. Hyal1 is composed of two domains, a catalytic domain and an EGF-like domain. The catalytic domain is in the form of $(\beta/\alpha)_8$ in which an alpha-helix and a beta-strand, which characterize the secondary structure of the protein, are each repeated eight times (Chao et al., 2007). The EGF-like domain is conserved in all variants in which the C-terminus of Hyal1 is spliced differently. The amino acid sequences of Hyal1 and PH20 are 35.1% identical, and the protein structure of PH20 has not yet been found.

A recombinant protein of human PH20 was developed by Halozyme Therapeutic, Inc. and has been sold under the trade name Hylenex® (Bookbinder et al., 2006; Frost, 2007).

When D146 and E148, which are the catalytic amino acids of PH20, were mutated to asparagine (D146N) and glutamine (E148Q), respectively, there was no enzymatic activity (Arming et al., 1997). In addition, when R246 of PH20 was substituted with glycine, the enzymatic activity was reduced by 90%, and when E319 was substituted with glutamine and R322 was substituted with threonine, the enzymatic activity disappeared. A variant in which 36 amino acids at the C-terminus of PH20 were removed (474-509 amino-acid truncation) showed a 75% reduction in enzymatic activity compared to wild-type PH20. This variant was not secreted extracellularly and remained in HeLa cells. When C-terminal 134 amino acids were removed from PH20, PH20 had no enzymatic activity and was not secreted extracellularly. According to Frost et al., the C-terminal 477-483 region of PH20 is essential for soluble expression (Frost, 2007). The activity of full-length PH20 (1 to 509) or a PH20 variant having a C-terminus truncated at position 467 was merely 10% of a PH20 variant having a C-terminus truncated at one of positions 477 to 483 (Frost, 2007).

Meanwhile, recombinant PH20 still has insufficient thermal stability or expression levels. Therefore, there is a great demand in industry for a recombinant hyaluronidase having further improved characteristics.

SUMMARY OF THE INVENTION

It is an object of the present invention to provide a novel hyaluronidase PH20 variant or fragment thereof which is improved in stability, enzyme activity and expression level, compared to wild-type PH20, preferably mature wild-type PH20.

Another object of the present invention is to provide a composition for treating cancer, comprising the above-described hyaluronidase PH20 variant or fragment thereof, and a method of treating cancer using the same.

To achieve the above objects, the present invention provides a hyaluronidase PH20 variant or fragment thereof, which comprises one or more amino acid residue substitutions in the region corresponding to an alpha-helix region and/or its linker region in the amino acid sequence of wild-type PH20, preferably mature wild-type PH20, and in which portion(s) of the N-terminal and/or C-terminal amino acid residues are selectively deleted.

The present invention also provides a composition for treating cancer, comprising the above-described hyaluronidase PH20 variant or fragment thereof, and a method of treating cancer using the same.

BRIEF DESCRIPTION OF THE DRAWINGS

FIG. 1 shows the protein tertiary structure model of PH20. The protein tertiary structure of PH20 was modeled using, as a template, Hyal1 (PDB ID: 2PE4) (Chao et. al., 2007) whose protein crystal structure was found, in Swiss-Model server (website swissmodel.expasy.org).

FIG. 1 in part A thereof shows the protein tertiary structure model of PH20, and indicates D146 and E148 which are catalytic amino acids. The protein tertiary structure model of PH20 is composed of eight repeats of a beta-strand and an alpha-helix.

FIG. 1 in part B thereof shows an eta (η) 8 loop in which alpha-helix 8 of PH20 and G340 to I344 which form a linker region in the N-terminal region of alpha-helix 8 are located. G340, T341, L342, S343 and I344 residues are each shown.

FIG. 1 in part C thereof shows amino acid residues (C351, Y357, and N363) which interact with the adjacent secondary structure, among the amino acids located in alpha-helix 8 of PH20. C351 forms a disulfide bond with C60 located in alpha-helix 1, Y357 hydrophobically interacts with F315 located between beta-strand 7 and alpha-helix 7, and N363 forms a hydrogen bond with a D69 residue located in alpha-helix 1.

FIG. 2 in graph A compares the protein expression levels of WT (wild type) PH20 and variants constructed in the present invention. WT and variants were expressed by transient transfection in ExpiCHO cells. WT had an expression level of 16.1 mg/L. The protein expression levels of variants based on the variants HM1 and HM6 were higher than that of WT, and the protein expression levels of HM4 and HM7 were the highest. The protein expression level of HM11 obtained by introducing additional amino acid substitutions (Y365F and I367L) into the variant HM6 decreased to 6.4 mg/mL.

FIG. 3 shows experimental results for the variants HM1 and HM6.

FIG. 3 in part A thereof shows the results of SDS-PAGE after purification of WT and the variants HM1 and HM6. Purification was performed using a HisTrap column and a Q Sepharose column. WT and the variants HM1 and HM6 had a molecular weight of approximately 70 kDa (figure legend: M, molecular weight marker; CS, supernatant; FT, flow-through; and Elution, elution fractions).

FIG. 3 in part B thereof shows the enzymatic activity values of WT and the variants HM1 and HM6, measured by turbidimetric assay at pH 7.0. In the present invention, the enzymatic activity value measured by the turbidimetric assay was expressed as specific activity.

FIG. 3 in part C thereof shows the enzymatic activities of WT and the variants HM1 and HM6, measured by substrate-gel assay. After SDS was removed with 2.5% Triton X-100 (w/v) at 4° C., an enzymatic reaction was performed at 37° C. for 1 to 4 h. The variant HM6 renatured faster than WT and the variant HM1 and hydrolyzed hyaluronic acid on polyacrylamide gel. The white band shows hyaluronic acid degraded by WT and the variant proteins.

FIG. 3 in part D thereof shows the enzymatic activities of WT and the variant HM1, measured by substrate-gel assay at pH of 5 to 8. WT and the variant HM1 exhibit activity in the pH range of 5 to 8, and show the highest enzymatic activity at pH 5.0. The variant HM1 has the signal peptide of human serum albumin or human Hyal1. The white band shows hyaluronic acid degraded by WT and the variant protein.

FIG. 3 in part E thereof shows the results of separating WT and the variants HM1 and HM6 by a phenyl column. The variants were eluted faster than WT from the phenyl column.

FIG. 4 shows the results in graphs A and B of analyzing the final product of hyaluronic acid, degraded by WT and the variant HM6, after 10 min and 1 h by means of an Amide-80 column.

FIG. 5 in part A thereof shows SDS-PAGE results after HisTrap column purification for variants HM7, HM8, HM9, HM10 and HM21.

FIG. 5 in part B thereof shows the results of measuring the enzymatic activities of WT and variants HM6, HM8, HM9, HM10, HM21 and HM7 by turbidimetric assay at pH 7.0.

FIG. 5 in part C thereof shows the results of measuring the enzymatic activities of WT and variants HM6, HM8, HM9, HM10, HM21 and HM7 by substrate-gel assay. The bar graph at the bottom of FIG. 5C shows the degree of enzymatic activity obtained by quantifying the band after staining the gel with Alcian blue. The white band shows hyaluronic acid degraded by WT and the variant proteins.

FIG. 5 in part D thereof shows the results of analyzing WT and variants HM8, HM9, HM10, HM21 and HM7 by phenyl column chromatography.

FIG. 5 in part E thereof shows the results of separating WT and variants HM6, HM8, HM9, HM10, HM21 and HM7 depending on their isoelectric points at the pH of 3 to 7 by means of IEF gel.

FIG. 6 shows experimental results for the variant HM11.

FIG. 6 in part A thereof shows the results of purifying protein by HisTrap column chromatography for the variant HM11.

FIG. 6 in part B thereof shows the results of measuring the enzymatic activities of WT and the variant HM11 at pH 7.0 by turbidimetric assay.

FIG. 7 shows experimental results for N-terminally truncated PH20 variants HM40, HM13, HM41, HM24, HM42, and HM25.

FIG. 7 in part A thereof shows the results of purifying protein by HisTrap column chromatography for the PH20 variants HM40, HM13, HM41, HM24, HM42 and HM25.

FIG. 7 in part B thereof shows the expression levels of the PH20 variants HM40, HM13, HM41, HM24, HM42, HM25, HP61 and HP62 in ExpiCHO cells.

FIG. 7 in part C thereof shows the enzymatic activities of the PH20 variants HM40, HM13, HM41, HM24, HM42 HM25, HP61 and HP62 measured at pH 7.0 by turbidimetric assay and expressed as specific activities.

FIG. 7 in part D thereof shows the enzymatic activities of the PH20 variants HM40, HM13, HM41, HM24, and HM42, measured by substrate-gel assay. The white band shows hyaluronic acid degraded by WT and the variant proteins.

FIG. 7 in part E thereof shows the results of analyzing WT and the variants HM40, HM13, HM41, HM24 and HM42 by phenyl column chromatography.

FIG. 7 in part F thereof shows the change in particle size with increasing temperature for the PH20 variants HM40, HM13, HM41 and HM42.

FIG. 8 shows experimental results for C-terminally truncated variants HM14, HM15 and HM16 constructed using HM6 as a template.

FIG. 8 in part A thereof shows the results of SDS-PAGE after HisTrap purification for the variants HM14, HM15 and HM16. As controls, WT and the variant HM6 were included.

FIG. 8 in part B thereof shows the results of measuring the enzymatic activities of WT and the variants HM6, HM14, HM15, and HM16 at pH 7.0 by turbidimetric assay.

FIG. 8 in part C thereof shows the results of measuring the enzymatic activities of WT and the variants HM6, HM14, HM15, and HM16 for 1, 2 and 4 h by substrate-gel assay. The right graph of FIG. 8 in part C thereof is a bar graph showing enzymatic activities measured after staining with Alcian-blue after 1 h of enzymatic reaction. The white band shows hyaluronic acid degraded by WT and the variant proteins.

FIG. 8 in part D thereof shows the results of analyzing WT and the variants HM6, HM14, HM15, and HM16 by phenyl column chromatography.

FIG. 8 in part E thereof shows the results of separating the variants HM14, HM15, and HM16 depending on their isoelectric points at the pH of 3 to 7 by IEF gel.

FIG. 9 shows experimental results for PH20 variants HM19 and HM20 constructed using HM10 as a template.

FIG. 9 in part A thereof shows the results of purified protein by HisTrap column chromatography for the PH20 variants HM19 and HM20.

FIG. 9 in part B thereof shows the results of comparing the enzymatic activities of the PH20 variant HM19 and HM20 at pH 7.0 by turbidimetric assay.

FIG. 9 in part C thereof shows the results of staining SDS gel with Alcian blue dye after 1 h of enzymatic reaction at 37° C. by substrate-gel assay for WT and the variants HM10, HM19, and HM20. The white band shows hyaluronic acid degraded by WT and the variant proteins.

FIG. 10 shows the results of measuring the aggregation temperatures of WT and the PH20 variants by dynamic light scattering (hereinafter referred to as DLS) system. The measurements were performed in triplicate and expressed as mean±S.E. values.

FIG. 11 shows a Stern-Volmer plot obtained after measuring the change in fluorescence of tryptophan residues of WT and PH20 variants by addition of acrylamide (0 to 0.5 M). Among amino acids, tryptophan is excited at 295 nm and emits maximum fluorescence wavelength at 340 nm. Acrylamide is a small molecule that can penetrate a protein structure and quench the fluorescence emission of tryptophan. As the protein structure is more flexible, the quenching of fluorescence by acrylamide is greater. F0 is the fluorescence value in the absence of acrylamide, and F is the fluorescence value in the presence of acrylamide (0 to 0.5 M). The change in the fluorescence value measured was expressed as the ratio F0/F.

FIG. 11 in part A thereof is a Stern-Volmer plot for WT and variants HM1, HM4, HM6 and HM7.

FIG. 11 in part B thereof is a Stern-Volmer plots for WT and variants HM14, HM15 and HM16.

FIG. 12 shows the expression levels of HM10-based PH20 variants in ExpiCHO cells.

FIG. 12 in part A thereof graphically shows the expression levels of respective variants.

FIG. 12 in part B thereof shows the expression levels of respective variants in the table. WT and the PH20 variants had a 6×His-tag at the C-terminus, and the protein expression levels after HisTrap column purification were expressed in mg/L. HM30 to HM33 variants were not expressed in ExpiCHO cells.

FIG. 13 shows Western blot results for cell cultures of variants HM29, HM30, HM31, HM32 and HM33. The C-termini of HM10-based variants HM29, HM30, HM31, HM32 and HM33 were truncated after A467, C464, D461, C358, and C455, respectively. HM29 whose C-terminus was truncated at A467 was expressed in ExpiCHO cells, but variants having a C-terminus truncated at C464 or shorter in length were not expressed in ExpiCHO cells. Primary antibody was rabbit anti-PH20 polyclonal antibody (Abcam) diluted at 1:500. Secondary antibody was Goat anti-rabbit IgG HRP diluted at 1:2,000.

FIG. 14 shows experimental results for C-terminally truncated variants constructed using HM10 as a template.

FIG. 14 in part A thereof shows the results of measuring enzymatic activities at pH 7.0 by turbidimetric assay for C-terminally truncated variants constructed using HM10 as a template.

FIG. 14 in part B thereof compares enzymatic activities depending on the C-terminal truncation sites of 17 PH20 variants (HM43, HM44, HM45, HM20, HM19, HM35, HM36, HM37, HM38, HM39, HM47, HM48, HM49, HM50, HM51, HM52 and HM10) constructed using HM10 as a template.

FIG. 14 in part C thereof shows the results of staining SDS gel with Alcian blue dye after 1 h of enzymatic reaction at 37° C. by substrate-gel assay for some (HM29, HM35, HM36, HM37, HM38, HM39, HM43, HM44 and HM45) of PH20 variants constructed using HM10 as a template. The white band shows hyaluronic acid degraded by WT and the variant proteins.

FIG. 15 shows SDS gel after passage through a final column during protein purification for the HP34 (FIG. 15 in Part a thereof) and HP46 (FIG. 15 in part B thereof) expressed in ExpiCHO cells. HP34 was subjected to a four-step chromatography purification procedure consisting of Q Sepharose, Butyl HP, Heparin and Blue Sepharose columns, and SDS gel is a result obtained after Blue Sepharose column chromatography. HP46 was subjected to a three-step chromatography purification procedure consisting of Q Sepharose, Butyl HP and Heparin columns, and SDS gel is a result obtained after Heparin column chromatography.

FIG. 16 shows the enzymatic activities of 6×His-tag-free PH20 variants HP34 and HP46 constructed using HM21 as a template.

FIG. 16 in part A thereof shows the results of measuring the enzymatic activities of WT and the variants HM21, HP34 and HP46 at pH 7.0 by turbidimetric assay.

FIG. 16 in part B thereof shows the results of measuring the enzymatic activities of HW2 and the variants HM21, HP34 and HP46 at pH 5.3 by Morgan-Elson assay ($K_m$: Michaelis-Menten constant, $k_{cat}$: turnover number, and $k_{cat}/K_m$: catalytic efficiency).

FIG. 17 shows the results of characterization of HM21-Based PH20 Variants.

FIG. 17 in part A thereof shows the results of measuring aggregation temperatures by DLS for 6×His-tag-free PH20 variants HP34 and HP46 constructed using HM21 as a template. As controls, the aggregation temperatures of HW2 and HM21 are shown.

FIG. 17 in part B thereof shows the results of measuring enzymatic activities for 1 h by substrate-gel assay for HW2 and the PH20 variants (HP20, HP34 and HP46).

FIG. 17 in part C thereof shows the results of performing a substrate-gel assay after allowing HW2 and HP46 samples to stand at pH 3.0 and pH 7.0 for 14 h. After SDS-PAGE, SDS was removed with 2.5% Triton X-100 (w/v), and an enzymatic reaction was performed at 37° C. for 1 h.

FIG. 17 in part D thereof shows the expression levels of PH20 variants HM21, HM53, HM54, HM55, HM56, HP59 and HP60 in ExpiCHO cells.

FIG. 17 in part E thereof shows the expression of the enzymatic activity value of PH20 variants HM21, HM53, HM54, HM55, HM56, HP59 and HP60, measured by the turbidimetric assay, as specific activity at pH 5.3.

FIG. 18 shows the results of measuring the stimulating index of CD4+ T cells in treatment with PH20 and PH20 variant at concentrations of 1.5 ng/mL and 15 ng/mL, respectively.

FIG. 19 shows the results of measuring the stimulating index of CD8+ T cells in treatment with PH20 and PH20 variant at concentrations of 1.5 ng/mL and 15 ng/mL, respectively.

DETAILED DESCRIPTION AND PREFERRED EMBODIMENTS OF THE INVENTION

Figure 5:
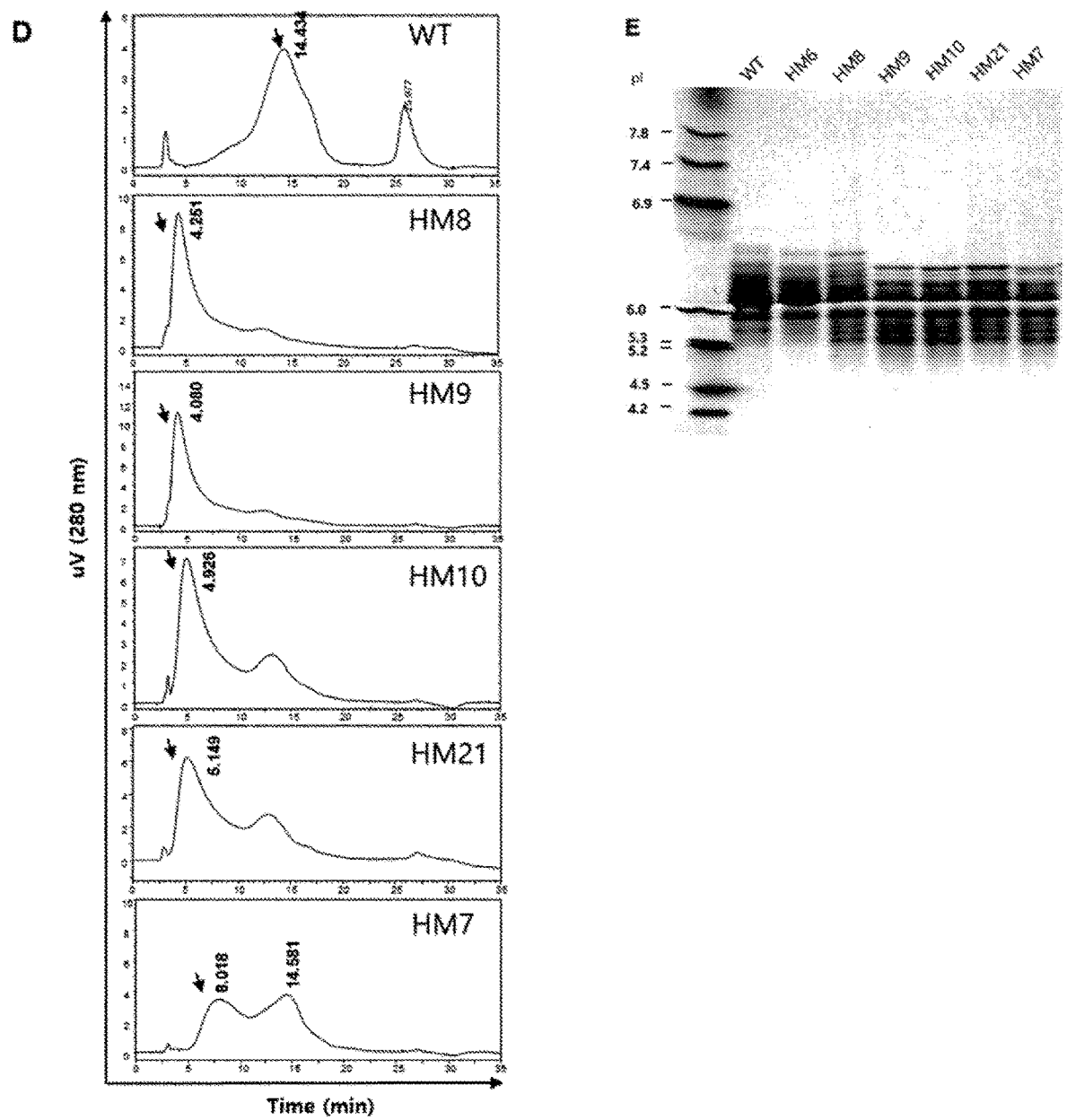
FIG. 5 shows experimental results for G340 to I344 amino acid mutations of PH20.

Unless defined otherwise, all the technical and scientific terms used herein have the same meaning as those generally understood by one of ordinary skill in the art to which the invention pertains. Generally, the nomenclature used herein is well-known and commonly used in the art.

The present invention provides a hyaluronidase PH20 variant or fragment thereof, which comprises one or more amino acid residue substitutions in the region corresponding to an alpha-helix region and/or its linker region, preferably an alpha-helix 8 region (S347 to C381) and/or a linker region (A333 to R346) between alpha-helix 7 and alpha-helix 8, in the amino acid sequence of wild-type PH20, preferably mature wild-type PH20, and in which portion(s) of the N-terminal and/or C-terminal amino acid residues are selectively deleted by truncation.

In the present invention, the positions of amino acid residues in each variant correspond to the amino acid positions of wild-type PH20 having the sequence of SEQ ID NO: 1.

In addition, in the present invention, "mature wild-type PH20" means a protein consisting of amino acid residues L36 to S490 of SEQ ID NO: 1, which lacks M1 to T35, which form a signal peptide, and A491 to L509, which are not related to the substantial function of PH20, in the amino acid sequence of wild-type PH20 having the sequence of SEQ ID NO: 1.

TABLE 1

Amino acid sequence of wild-type PH20

(SEQ ID NO: 1)
MGVLKFKHIFFRSFVKSSGVSQIVFTFLLIPCCLTLNFRAPPVIPNVPFL

WAWNAPSEFCLGKFDEPLDMSLFSFIGSPRINATGQGVTIFYVDRLGYYP

YIDSITGVTVNGGIPQKISLQDHLDKAKKDITFYMPVDNLGMAVIDWEEW

TABLE 1-continued

Amino acid sequence of wild-type PH20

RPTWARNWKPKDVYKNRSIELVQQQNVQLSLTEATEKAKQEFEKAGKDFL

VETIKLGKLLRPNHLWGYYLFPDCYNHHYKKPGYNGSCFNVEIKRNDDLS

WLWNESTALYPSIYLNTQQSPVAATLYVRNRVREAIRVSKIPDAKSPLPV

FAYTRIVFTDQVLKFLSQDELVYTFGETVALGASGIVIWGTLSIMRSMKS

CLLLDNYMETILNPYIINVTLAAKMCSQVLCQEQGVCIRKNWNSSDYLHL

NPDNFAIQLEKGGKFTVRGKPTLEDLEQFSEKFYCSCYSTLSCKEKADVK

DTDAVDVCIADGVCIDAFLKPPMETEEPQIFYNASPSTLSATMFIVSILF

LIISSVASL

Specifically, the PH20 variant or fragment thereof according to the present invention may comprise one or more mutations, preferably amino acid residue substitutions selected from the group consisting of T341A, T341C, T341G, S343E, M345T, K349E, L353A, L354I, N356E and I361T, more preferably selected from the group consisting of T341A, T341C, L354I and N356E in wild-type PH20 having the amino acid sequence of SEQ ID NO: 1.

In the present invention, the term "PH20 variant" is intended to include mutation of portion(s) of amino acid residues, preferably substitution of one or more amino acid residues in the amino acid sequence of wild-type PH20, as well as occurrence of deletion of portion(s) of amino acid residues at N-terminus or C-terminus together with substitution of the amino acid residues, and is used as substantially the same meaning as the expression "PH20 variant or fragment thereof".

In the present invention, the protein tertiary structure of PH20 located outside the active site was studied through the protein structure modeling of human PH20 on the basis of Hyal1 (SEQ ID NO: 2) which is a human hyaluronidase whose protein tertiary structure is known. As a result, amino acids located in the alpha-helix 8 region of PH20 were selected and substituted with the amino acid sequence of alpha-helix 8 of Hyal1, thereby attempting to enhance the thermal stability of the protein structure without affecting the catalytic activity of the enzyme. In particular, alpha-helix 8 is located in the outer portion of the protein tertiary structure of PH20, and there is less interaction with the adjacent alpha-helix or beta-strand than the other alpha-helices of PH20. According to the present invention, it has been found that when the amino acid sequence of the alpha-helix 8 region of human PH20 and a linker region between alpha-helix 7 and alpha-helix 8 is partially substituted with the amino acid sequence of the alpha-helix 8 region of highly hydrophilic Hyal1 and a linker region between alpha-helix 7 and alpha-helix 8 of Hyal1, the enzymatic activity at neutral pH and the protein aggregation temperature ($T_{agg.}$) increase. Based on these experimental results, it has been found that a novel PH20 variant or fragment thereof, which has increased enzymatic activity and thermal stability compared to wild-type PH20, can be provided.

Thus, the PH20 variant according to the present invention comprises one or more amino acid residue substitutions selected from the group consisting of T341A, T341C, T341G, S343E, M345T, K349E, L353A, L354I, N356E and I361T, preferably selected from the group consisting of T341A, T341C, L354I and N356E in the amino acid sequence of wild-type PH20 (having the amino acid sequence of SEQ ID NO: 1), preferably mature wild-type PH20 (having a sequence consisting of amino acid residues L36 to S490 in the amino acid sequence of SEQ ID NO: 1).

The PH20 variant according to the present invention also comprises one or more amino acid residue substitutions in the region corresponding to an alpha-helix region and/or its linker region, preferably an alpha-helix 8 region (S347 to C381) and/or the linker region (A333 to R346) between alpha-helix 7 and alpha-helix 8, more preferably T341 to N363, T341 to I361, L342 to I361, S343 to I361, I344 to I361, M345 to I361, or M345 to N363.

In particular, in the PH20 variant according to the present invention, the alpha-helix 8 region (S347 to C381) and/or the linker region (A333 to R346) between alpha-helix 7 and alpha-helix 8 of the wild-type PH20, preferably the mature wild-type PH20 may be substituted with portion(s) of amino acid residues of the corresponding region (see Tables 2 and 3) of Hyal1 having the sequence of SEQ ID NO: 2, but is not limited thereto.

TABLE 2

Amino acid sequence of wild-type Hyal1

(SEQ ID NO: 2)
MAAHLLPICALFLTLLDMAQGFRGPLLPNRPFTTVWNANTQWCLERHGVD

VDVSVFDVVANPGQTFRGPDMTIFYSSQLGTYPYYTPTGEPVFGGLPQNA

SLIAHLARTFQDILAAIPAPDFSGLAVIDWEAWRPRWAFNWDTKDIYRQR

SRALVQAQHPDWPAPQVEAVAQDQFQGAARAWMAGTLQLGRALRPRGLWG

FYGFPDCYNYDFLSPNYTGQCPSGIRAQNDQLGWLWGQSRALYPSIYMPA

VLEGTGKSQMYVQHRVAEAFRVAVAAGDPNLPVLPYVQIFYDTTNHFLPL

DELEHSLGESAAQGAAGVVLWVSWENTRTKESCQAIKEYMDTTLGPFILN

VTSGALLCSQALCSGHGRCVRRTSHPKALLLLNPASFSIQLTPGGGPLSL

RGALSLEDQAQMAVEFKCRCYPGWQAPWCERKSMW

TABLE 3

Comparison of alpha-helices and amino
acid sequence between PH20 and Hyal1

| alpha-helix | amino acid sequences of PH20 | amino acid sequences of Hyal1 |
|---|---|---|
| alpha-helix 1 | P56~D65 | N39~G48 |
| alpha-helix 3 | S119~M135 | S101~I117 |
| alpha-helix 4' | K161~N176 | K144~H159 |
| alpha-helix 4 | S180~R211 | P163~R194 |
| alpha-helix 5 | F239~S256 | P222~S239 |
| alpha-helix 6 | A274~D293 | K257~G277 |
| alpha-helix 7 | S317~G332 | P299~G314 |
| alpha-helix 8 | S347~C381 | T329~C363 |

More specifically, the novel PH20 variant or fragment thereof according to the present invention preferably comprises an amino acid residue substitution of L354I and/or N356E in the amino acid sequence of wild-type PH20, preferably mature wild-type PH20, and further comprises at least the amino acid residue substitution at one or more positions selected from among T341 to N363, particularly one or more positions selected from the group consisting of T341, L342, S343, I344, M345, S347, M348, K349, L352, L353, D355, E359, I361 and N363, but is not limited thereto.

More preferably, the amino acid residue substitution at one or more positions selected from the group consisting of T341, L342, S343, I344, M345, S347, M348, K349, L352, L353, D355, E359, I361 and N363 may be one or more amino acid residue substitutions selected from the group consisting of T341A, T341C, T341D, T341G, T341S, L342W, S343E, I344N, M345T, S347T, M348K, K349E, L352Q, L353A, D355K, E359D, I361T and N363G, but is not limited thereto.

Preferably, the novel PH20 variant or fragment thereof according to the present invention may comprise amino acid residue substitutions of M345T, S347T, M348K, K349E, L352Q, L353A, L354I, D355K, N356E, E359D and I361T, and may further comprise one or more amino acid residue substitutions selected from the group consisting of T341A, T341C, T341D, T341G, T341S, L342W, S343E, I344N and N363G, but is not limited thereto.

More preferably, the novel PH20 variant or fragment thereof according to the present invention may be any one selected from the following amino acid residue substitution groups, but is not limited thereto:
(a) T341S, L342W, S343E, I344N, M345T, S347T, M348K, K349E, L352Q,
L353A, L354I, D355K, N356E, E359D and I361T;
(b) L342W, S343E, I344N, M345T, S347T, M348K, K349E, L352Q, L353A,
L354I, D355K, N356E, E359D and I361T;
(c) M345T, S347T, M348K, K349E, L352Q, L353A, L354I, D355K, N356E, E359D, I361T and N363G;
(d) T341G, L342W, S343E, I344N, M345T, S347T, M348K, K349E, L352Q, L353A, L354I, D355K, N356E, E359D and I361T;
(e) T341A, L342W, S343E, I344N, M345T, S347T, M348K, K349E, L352Q, L353A, L354I, D355K, N356E, E359D and I361T;
(f) T341C, L342W, S343E, I344N, M345T, S347T, M348K, K349E, L352Q, L353A, L354I, D355K, N356E, E359D and I361T;
(g) T341D, L342W, S343E, I344N, M345T, S347T, M348K, K349E, L352Q, L353A, L354I, D355K, N356E, E359D and I361T;
(h) I344N, M345T, S347T, M348K, K349E, L352Q, L353A, L354I, D355K, N356E, E359D and I361T; and
(i) S343E, I344N, M345T, S347T, M348K, K349E, L352Q, L353A, L354I, D355K, N356E, E359D and I361T.

In the present invention, an expression described by one-letter amino acid residue code together with numbers, such as "S347", means the amino acid residue at each position in the amino acid sequence of SEQ ID NO: 1.

For example, "S347" means that the amino acid residue at position 347 in the amino acid sequence of SEQ ID NO: 1 is serine.

In addition, "S347T" means that serine at position 347 of SEQ ID NO: 1 is substituted with threonine.

The PH20 variant or fragment thereof according to the present invention is interpreted as including variants or fragments thereof in which the amino acid residue at a specific amino acid residue position is conservatively substituted.

As used herein, the term "conservative substitution" refers to modifications of a PH20 variant that involves the substitution of one or more amino acids for amino acids having similar biochemical properties that do not result in loss of the biological or biochemical function of the PH20 variant.

A "conservative amino acid substitution" is one in which the amino acid residue is replaced with an amino acid residue having a similar side chain. Families of amino acid residues having similar side chains have been defined and are well known in the art to which the present invention pertains. These families include amino acids with basic side chains (e.g., lysine, arginine and histidine), amino acids with acidic side chains (e.g., aspartic acid and glutamic acid), amino acids with uncharged polar side chains (e.g., glycine, asparagine, glutamine, serine, threonine, tyrosine, and cysteine), amino acids with nonpolar side chains (e.g., alanine, valine, leucine, isoleucine, proline, phenylalanine, methionine, and tryptophan), amino acids with beta-branched side chains (e.g., threonine, valine, and isoleucine), and amino acids with aromatic side chains (e.g., tyrosine, phenylalanine, tryptophan, and histidine).

It is envisioned that the PH20 variant or fragments thereof of the present invention may still retain the activity although it has conservative amino acid substitutions.

In addition, the PH20 variant or fragment thereof according to the present invention is interpreted to include PH20 variants or fragments thereof having substantially the same function and/or effect as those/that of the PH20 variant or fragment thereof according to the present invention, and having an amino acid sequence homology of at least 80% or 85%, preferably at least 90%, more preferably at least 95%, most preferably at least 99% to the PH20 variant or fragment thereof according to the present invention.

The PH20 variants or fragments thereof according to the present invention have increased expression levels in animal cells and an increased protein refolding rate, thereby increasing high thermal stability, compared to mature wild-type PH20. Furthermore, the enzymatic activity of the PH20 variants or fragments thereof was more increased than or similar to that of mature wild-type PH20 despite an increase in the thermal stability.

Meanwhile, it is known that when the C-terminal region of the mature wild type PH20 is truncated, the enzymatic activity is reduced. However, the PH20 variants according to the present invention, due to the increased protein refolding and thermal stability, exhibited similar or increased enzymatic activities compared to the mature wild type PH 20 despite the C-terminal being truncated. In addition, PH20 variants in this present invention maintained the enzymatic activities when the N-terminal amino acids were truncated up to five amino acids. This indicated that for the protein expression and enzyme activities, the role of amino acid residues from P41 of the N-terminus are important.

Accordingly, the PH20 variant or fragment thereof according to the present invention is characterized in that it comprises portion(s) of amino acid residue substitutions in the alpha-helix 8 region (S347 to C381) and/or the linker region (A333 to R346) between alpha-helix 7 and alpha-helix 8 in the amino acid sequence of wild-type PH20, and one or more of the N-terminal and/or C-terminal amino acid residues are additionally deleted, but is not limited thereto.

In one aspect, the PH20 variant or fragment thereof according to the present invention may be one in which truncation occurs before an amino acid residue selected from the group consisting of M1 to P42 at the N-terminus of the amino acid sequence of SEQ ID NO: 1, preferably before an amino acid residue L36, N37, F38, R39, A40, P41, or P42, so that portion(s) of amino acid residues at the N-terminus are deleted, and/or truncation occurs after an amino acid residue selected from the group consisting of V455 to L509, preferably after an amino acid residue selected from the group consisting of V455 to S490, most preferably after an amino acid residue V455, C458, D461, C464, I465, D466, A467, F468, K470, P471, P472, M473, E474, T475, E476, P478, I480, Y482, A484, P486, T488, or S490 at the C-terminus, so that portion(s) of amino acid residues at the C-terminus are deleted.

The expression "truncation occurs before an amino acid residue selected from the group consisting of M1 to P42 at the N-terminus" means that amino acid residues up to the amino acid residue which immediately precedes the amino acid residue selected from among M1 to P42 at the N-terminus are deleted by truncation.

For example, the expression "truncation occurs before an amino acid residue L36, N37, F38, R39, A40, P41, or P42" respectively means that all amino acid residues from M1 to T35 immediately before L36, all amino acid residues from M1 to L36 immediately before N37, all amino acid residues from M1 to N37 immediately before F38, all amino acid residues from M1 to F38 immediately before R39, all amino acid residues from M1 to R39 immediately before A40, all amino acid residues from M1 to A40 immediately before P41, or all amino acid residues from M1 to P41 immediately before P42 in the amino acid sequence of SEQ ID NO: 1 are removed by truncation, respectively.

In addition, the expression "truncation occurs after an amino acid residue selected from the group consisting of V455 to L509 at the C-terminus" means that an amino acid residue immediately after an amino acid residue selected from among V455 to L509 at the C-terminus is cleaved and deleted.

For example, the expression "cleavage occurs after an amino acid residue V455, C458, D461, C464, I465, D466, A467, F468, K470, P471, P472, M473, E474, T475, E476, P478, I480, Y482, A484, P486, T488 or S490 at the C-terminus" means that amino acid residues starting with the amino acid residue which immediately follows the amino acid residue V455, C458, D461, C464, I465, D466, A467, F468, K470, P471, P472, M473, E474, T475, E476, P478, I480, Y482, A484, P486, T488 or S490, respectively, in the amino acid sequence of SEQ ID NO: 1 are removed by truncation.

Preferably, the novel PH20 variant or fragment thereof according to the present invention may be selected from the group consisting of amino acid sequences of SEQ ID NOs: 60 to 115, but is not limited thereto.

Most preferably, the novel PH20 variant or fragment thereof according to the present invention may have the amino acid sequence of SEQ ID NO: 99. The novel PH20 variant having an amino acid sequence of SEQ ID NO: 99 may comprise 15 amino acid residue substitutions of T341S, L342W, S343E, I344N, M345T, S347T, M348K, K349E, L352Q, L353A, L354I, D355K, N356E, E359D and I361T, and deletion before F38 residue at the N-terminus, and truncation after F468 residue at the C-terminus.

The sequences of the substituted or truncated amino acids in the PH20 variants constructed in the specific embodiments according to the present invention are as shown in Table 11.

A study focused on increasing the enzymatic activity and thermal stability of PH20 by amino acid substitution of an alpha-helix and its linker region, which are secondary structures forming the tertiary structure of the protein, as disclosed in the present invention, has not been previously reported. Previous studies reported that the enzymatic activity of wild-type PH20 changes depending on the truncation positions of amino acid residues located at the C-terminal region. However, in the present invention, a specific alpha-helix forming the secondary structure of PH20 was substituted with the alpha-helix of other human hyaluronidase, thereby constructing PH20 variants having higher stability than wild-type PH20. These variants may be variants in which the interaction of the substituted alpha-helix domain with portions forming other secondary structures of PH20 shows a pattern different from that of wild-type PH20, indicating that the variants have consistent enzymatic activity regardless of the C-terminal truncation position.

In specific embodiment, the novel PH20 variant or fragment thereof according to the present invention, which has increased enzymatic activity and thermal stability compared to mature wild-type PH20, may be one which comprises one or more amino acid residue substitutions selected from the group consisting of T341A, T341C, T341G, S343E, M345T, K349E, L353A, L354I, N356E and I361T, and in which portion(s) of amino acids located in an alpha-helix 8 region (S347 to C381) and/or the linker region (A333 to R346) between alpha-helix 7 and alpha-helix 8 in the amino acid sequence of wild-type PH20, preferably mature wild-type PH20, are substituted with other amino acids.

Specifically, the amino acid substitution in the alpha-helix 8 and the linker region between alpha-helix 7 and alpha-helix 8 comprises the substitution of portion(s) of amino acids in the region of amino acids T341 to N363, T341 to I361, L342 to I361, S343 to I361, I344 to I361, M345 to I361, or M345 to N363.

In order to examine the effect of C-terminal truncation in PH20 variants in which alpha-helix 8 and a linker region between alpha-helix 7 and alpha-helix 8 are substituted, three PH20 variants (HM6, HM10 and HM21) were selected as templates.

HM6 is a variant in which amino acids in M345 to N363 region are substituted with the amino acid sequence of Hyal1 (substitutions of M345T, S347T, M348K, K349E, L352Q, L353A, L354I, D355K, N356E, E359D and I361T in SEQ ID NO: 1). In addition, HM6 is a variant in which the substitution of alpha-helix 8 and a linker region between alpha-helix 7 and alpha-helix 8 is the least substituted variant among the PH20 variants according to the present invention, which do not comprise additional C-terminal truncation (that is, a form in which the C-terminal amino acid residue is S490, like mature wild-type PH20);

HM10 is a variant in which amino acids in L342 to I361 region are substituted with the amino acid sequence of Hyal1 (substitutions of L342W, S343E, I344N, M345T, S347T, M348K, K349E, L352Q, L353A, L354I, D355K, N356E, E359D and I361T in SEQ ID NO: 1), and which has the highest thermal stability while having an enzymatic activity similar to that of mature wild-type PH20 among the PH20 variants according to the present invention, which do not comprise additional C-terminal truncation; and HM21 is a variant in which amino acids in T341 to I361 region are substituted with the amino acid sequence of Hyal1 (substitutions of T341S, L342W, S343E, I344N, M345T, S347T, M348K, K349E, L352Q, L353A, L354I, D355K, N356E, E359D and I361T in SEQ ID NO: 1), which does not comprise additional C-terminal truncation, and which has an enzymatic activity which is about two times higher than that of wild-type PH20 at pH 7.0.

The HM6-based PH20 variants constructed in the present invention have the N-terminus truncated at L36 and the C-terminus truncated after at I465, F468, or P471 as shown in Table 4 below.

TABLE 4

C-terminal amino acid truncated PH20 variants constructed using HM6 as a template

| Variant | Total length | Substituted region | Number of substituted amino acids | Number of truncated amino acids |
|---|---|---|---|---|
| HM6 | 36~490 | M345~I361 | 11 | 0 |
| HM14 | 36~465 | | 11 | 25 |
| HM15 | 36~468 | | 11 | 22 |
| HM16 | 36~471 | | 11 | 19 |

The HM10-based PH20 variants commonly have the N-terminus truncated before the F38 residue and the C-terminus truncated after the V455, C4578, D46, C464, I465, D466, A467, F468, K470, P472, M473, E474, T475, E476, P478, I480, Y482, A484, P486, or T488 residue as shown in Table 5 below.

TABLE 5

C-terminal amino acid truncated PH20 variants constructed using HM10 as a template

| Variant | Total length | Substituted region | Number of substituted amino acids | Number of truncated amino acids |
|---|---|---|---|---|
| HM10 | 36~490 | L342~I361 | 14 | 0 |
| HM52 | 38~488 | | 14 | 4 |
| HM51 | 38~486 | | 14 | 6 |
| HM50 | 38~484 | | 14 | 8 |
| HM49 | 38~482 | | 14 | 10 |
| HM48 | 38~480 | | 14 | 12 |
| HM47 | 38~478 | | 14 | 14 |
| HM39 | 38~476 | | 14 | 16 |
| HM38 | 38~475 | | 14 | 17 |
| HM37 | 38~474 | | 14 | 18 |
| HM36 | 38~473 | | 14 | 19 |
| HM35 | 38~472 | | 14 | 20 |
| HM19 | 38~470 | | 14 | 22 |
| HM20 | 38~468 | | 14 | 24 |
| HM45 | 38~467 | | 14 | 25 |
| HM29 | 36~467 | | 14 | 23 |
| HM44 | 38~466 | | 14 | 26 |
| HM43 | 38~465 | | 14 | 27 |
| HM30 | 36~464 | | 14 | 26 |
| HM31 | 36~461 | | 14 | 29 |
| HM32 | 36~458 | | 14 | 32 |
| HM33 | 36~455 | | 14 | 35 |
| HP19 | 38~470 | | 14 | 22 |
| HP20 | 38~468 | | 14 | 24 |

As shown in the examples of variants which comprise amino acid substitutions in the L342 to I361 region corresponding to the alpha-helix 8 region and the linker region between alpha-helix 7 and alpha-helix 8 of HM10 as a template and in which the N-terminus was truncated before the F38 residue and the C-terminus was truncated at I465, D466, A467, F468, K470, P472, M473, E474, T475, E476, P478, I480, Y482, A484, P486, or T488, the PH20 variants according to the present invention exhibited an enzymatic activity similar to that of mature wild-type PH20 regardless of the C-terminal truncation position.

As shown in Table 6 below, two HM21-based PH20 variants commonly have the N-terminus truncated before the F38 residue and the C-terminus truncated after the F468 or K470 residue.

TABLE 6

C-terminal amino acid truncated PH20 variants constructed using HM21 as a template

| Variant | Total length | Substituted region | Number of substituted amino acids | Number of truncated amino acids |
|---|---|---|---|---|
| HM21 | 38~490 | T341~I361 | 15 | 2 |
| HP34 | 38~470 | | 15 | 22 |
| HP46 | 38~468 | | 15 | 24 |

Variants were constructed using, as a template, HM21 having an enzymatic activity which is about two times higher than that of mature wild-type PH20. These variants are those which comprise amino acid substitutions in the T341 to I361 region corresponding to the alpha-helix 8 region and the linker region between alpha helix 7 and alpha-helix 8 and in which the N-terminus was truncated before the F38 residue, and the C-terminus was truncated after F468 or K470. Surprisingly, these variants maintained the high enzymatic activity of HM21 regardless of the C-terminal truncation position.

In the study conducted by Frost et al., when the length of PH20 is shorter due to the truncation before the amino acid position of 477, the enzymatic activity decreased to about 10% of a variant having a C-terminus truncated after the position 477 (Frost, 2007). However, in the present invention, when amino acids in alpha-helix 8 of PH20 and its linker region were substituted, the enzymatic activity was maintained regardless of the C-terminal truncation position due to the increase in the stability of the protein. This result is very significant in that it solves the problem that the enzymatic activity of wild-type PH20 is reduced due to the C-terminal truncation of wild-type PH20.

In addition, in the present invention, the effect of the N-terminal amino acids of PH20, which has not been known previously, was studied.

In order to examine the effects of N-terminal truncation of amino acids in HM6 variants in which portion(s) of amino acid residues in the region (M345 to I361) corresponding to the alpha-helix 8 region of wild-type PH20 and the linker region between alpha-helix 7 and alpha-helix 8 were substituted with amino acid residues of the corresponding alpha-helix 8 region of Hyal1 and the linker region between alpha-helix 7 and alpha-helix 8 (i.e., substitutions of M345T, S347T, M348K, K349E, L352Q, L353A, L354I, D355K, N356E, E359D or I361T in SEQ ID NO: 1 and comprising no additional C-terminal truncation), variants, in which amino acid residues L36 to V47 in SEQ ID NO: 1 were substituted with FRGPLLPNR (SEQ ID NO: 116) or amino acid residues L36 to A52 in SEQ ID NO: 1 were substituted with FRGPLLPNRPFTTV (SEQ ID NO: 117), were constructed using HM6 as a template. In addition, using HM6 as a template, the variants HM40, HM13, HM41, HM24, HM42 and HM25 were constructed in which the N-terminus in the amino acid sequence of SEQ ID NO: 1 was truncated before the N37, F38, R39, A40, P41 or P42 residue (see Table 7).

TABLE 7

N-terminal amino acid cleaved variants based on HM6

| Variant | Total length | Substituted region | Number of substituted amino acids | Number of truncated amino acids |
|---|---|---|---|---|
| HM6 | 36~490 | M345~I361 | 11 | 0 |
| HM40 | 37~490 | | 11 | 1 |

TABLE 7-continued

N-terminal amino acid cleaved variants based on HM6

| Variant | Total length | Substituted region | Number of substituted amino acids | Number of truncated amino acids |
|---------|--------------|--------------------|-----------------------------------|---------------------------------|
| HM13 | 38~490 | | 11 | 2 |
| HM41 | 39~490 | | 11 | 3 |
| HM24 | 40~490 | | 11 | 4 |
| HM42 | 41~490 | | 11 | 5 |
| HM25 | 42~490 | | 11 | 6 |
| HM17 | | L36~V47, M345~I361 | 23 | |
| HM18 | | L36~A52, M345~I361 | 28 | |

As a result, it was shown that when the N-terminus of HM6 was truncated before the N37, F38, R39, A40 or P41 residue, the enzymatic activity was not greatly influenced; however, when the N-terminus was truncated before the P42 residue, the enzymatic activity significantly decreased, indicating that the N-terminal region of PH20, located after P41, is important for protein expression and enzymatic activity. In addition, when amino acids in the N-terminal L36 to V47 or L36 to A52 region of HM6 were substituted with the amino acids of Hyal1, the variant protein was not expressed in ExpiCHO cells, indicating that the N-terminal region is important for protein expression.

In addition, in the present invention, it was attempted to increase the expression of a recombinant PH20 protein by using the signal peptide of other proteins having a high level of protein expression in animal cells, instead of using the signal peptide specific to PH20.

Therefore, in another aspect, the novel PH20 variant according to the present invention may be one in which the N-terminus further comprises a human growth hormone signal peptide having an amino acid sequence MATGSRT-SLLLAFGLLCLPWLQEGSA of SEQ ID NO: 3, a human serum albumin signal peptide having an amino acid sequence MKWVTFISLLFLFSSAYS of SEQ ID NO: 4, or a human Hyal1 signal peptide having an amino acid sequence MAAHLLPICALFLTLLDMAQG of SEQ ID NO: 5, as shown in Table 8 below, instead of the signal peptide of wild-type PH20, which consists of M1 to T35, but is not limited thereto.

The expression "instead of the signal peptide of wild-type PH20, which consists of M1 to T35" means a case in which the signal peptide of wild-type PH20 is partially or completely deleted; thus, it does not perform its function. In addition, the expression is meant to include a case in which portion(s) of the N-terminus is further deleted, for example, a case in which truncation occurs before the N37, F38, R39, A40, P41 or P42 residue occurs so that an additional deletion of the N-terminus together with the deletion of the signal peptide of wild-type PH20 occurs.

TABLE 8

Amino acid sequences of signal peptide of human growth hormone, human serum albumin or human Hyal1

| | Amino acid sequences | SEQ NO. |
|---|----------------------|---------|
| human growth hormone | MATGSRTSLLLAFGLLCLPWLQEGSA | 3 |
| human serum albumin | MKWVTFISLLFLFSSAYS | 4 |
| human Hyal1 | MAAHLLPICALFLTLLDMAQG | 5 |

In another aspect, the present invention provides a composition for treating cancer comprising the novel PH20 variant according to the present invention, and a method for treating cancer using the same.

Cancers or carcinomas that can be treated by the novel PH20 variant according to the present invention are not limited particularly, but includes both solid cancers and blood cancers. The cancer may be selected from the group consisting of skin cancer such as melanoma, liver cancer, hepatocellular carcinoma, gastric cancer, breast cancer, lung cancer, ovarian cancer, bronchial cancer, nasopharyngeal cancer, laryngeal cancer, pancreatic cancer, bladder cancer, colorectal cancer, colon cancer, cervical cancer, brain cancer, prostate cancer, bone cancer, thyroid cancer, parathyroid cancer, kidney cancer, esophageal cancer, biliary tract cancer, testicular cancer, rectal cancer, head and neck cancer, spinal cancer, ureteral cancer, osteosarcoma, neuroblastoma, fibrosarcoma, rhabdomyosarcoma, astrocytoma, neuroblastoma and glioma, but is not limited thereto. Preferably, cancers that can be treated by the composition according to the present invention may be selected from the group consisting of colorectal cancer, breast cancer, lung cancer, and kidney cancer, but are not limited thereto.

The composition of the present invention may be a pharmaceutical composition. The pharmaceutical composition may further comprise a pharmaceutically acceptable carrier. The carrier that is typically used in the formulation of drugs may be one or more selected from the group consisting of, but not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrups, methyl cellulose, methyl-hydroxybenzoate, propyl-hydroxybenzoate, talc, magnesium stearate, and mineral oil. In addition, the pharmaceutical composition may further comprise one or more selected from the group consisting of diluents, excipients, lubricants, wetting agents, sweeteners, aromatics, emulsifiers, suspensions, and preservatives which are commonly used in manufacturing pharmaceutical compositions.

The pharmaceutical composition of the present invention may be administered orally or parenterally. The parenteral administration is carried out by intravenous injection, subcutaneous injection, intramuscular injection, intraperitoneal injection, endothelial administration, topical administration, intranasal administration, intrapulmonary administration, rectal administration, and the like. For the oral administration, the active ingredient in the composition needs to be formulated into a coated dosage form or into a dosage form which can protect the active ingredient from being disintegrated in stomach considering that peptides and proteins are digested in stomach. In addition, the present composition may be administered via any device by which the active ingredient can move to the target cell of interest.

The pharmaceutical composition may be formulated in the form of solutions, suspensions, syrups or emulsions in oils or aqueous media, or in the form of extracts, grains, powders, granules, tablets or capsules, and may additionally include dispersing or stabilizing agents for the purpose of formulation.

In particular, the composition for treating cancer according to the present invention is characterized for its use in combined treatment with other anticancer drugs.

An anticancer drug that can be used for combined treatment with the novel PH20 variant according to the present invention is preferably a chemical anticancer drug, an antibody-based anticancer drug, an RNAi, or a cell therapeutic agent, but is not limited thereto.

The anticancer drug that can be used for combined treatment with the novel PH20 variant according to the present invention is preferably an immuno-oncologic agent, more preferably an immune checkpoint inhibitor, but is not limited thereto.

In another aspect, the present invention relates to a nucleic acid encoding the PH20 variant or a variant thereof.

The nucleic acids, as used herein, may be present in cells, in the cell lysate, or in the partially purified or substantially pure form. "Isolated" or "substantially pure", when referring to nucleic acids, refer to those that have been purified away from other cellular components or other contaminants, e.g., other cellular nucleic acids or proteins, by standard techniques, including alkaline/SDS treatment, CsCl banding, column chromatography, agarose gel electrophoresis, and others well known in the art. The nucleic acids of the present invention may be DNA or RNA.

In still another aspect, the present invention relates to vector comprising the nucleic acid. For expression of the PH20 variant or fragment thereof according to the present invention, a DNA encoding the PH20 variant can be obtained by standard molecular biology techniques (e.g., PCR amplification or cDNA cloning using a hybridoma that expresses the PH20 variant), and the DNA can be inserted into an expression vector such that it is "operably linked" to transcriptional and translational control sequences.

As used herein, the term "operably linked" is intended to mean that a gene encoding the PH20 variant or fragment thereof is ligated into a vector such that transcriptional and translational control sequences serve their intended function of regulating the transcription and translation of the gene encoding the PH20 variant or fragment thereof. The expression vector and expression control sequences are chosen to be compatible with the expression host cell used. The genes encoding the PH20 variant are inserted into the expression vector by standard methods (e.g., ligation of complementary restriction enzyme sites on a fragment of the gene encoding the PH20 variant or fragment thereof and vector, or blunt end ligation if no restriction enzyme sites are present).

In addition, the recombinant expression vectors carry regulatory sequences that control the expression of a gene encoding the PH20 variant in the host cell. The term "regulatory sequence" may include promoters, enhancers and other expression control elements (e.g., polyadenylation signals) that control the transcription or translation of the genes encoding the PH20 variant or fragment thereof. It will be appreciated by those skilled in the art that the design of the expression vector, including the selection of regulatory sequences, may depend on such factors as the choice of the host cell to be transformed, the level of expression of protein desired, etc.

In yet another aspect, the present invention relates to a host cell comprising the nucleic acid or the vector. The host cell according to the present invention is preferably selected from the group consisting of animal cells, plant cells, yeasts, *E. coli*, and insect cells, but is not limited thereto.

Specifically, the host cell according to the present invention may be prokaryotic cells such as *E. coli, Bacillus subtilis, Streptomyces* sp., *Pseudomonas* sp., *Proteus mirabilis* or *Staphylococcus* sp., fungi such as *Aspergillus* sp., yeasts such as *Pichia pastoris, Saccharomyces cerevisiae, Schizosaccharomyces* sp. and *Neurospora crassa*, and eukaryotic cells such as lower eukaryotic cells, and higher other eukaryotic cells such as insect cells.

In addition, the host cells may be derived from plants or mammals. Preferably, examples of the host cells include, but are not limited to, monkey kidney cells (COS7), NSO cells, SP2/0, Chinese hamster ovary (CHO) cells, W138, baby hamster kidney (BHK) cells, MDCK, myeloma cells, HuT 78 cells and HEK293 cells. More preferably, CHO cells may be used.

The nucleic acid or the vector is transfected into a host cell. "Transfection" can be performed using various techniques that are generally used to introduce foreign nucleic acid (DNA or RNA) into prokaryotic or eukaryotic cells, for example, electrophoresis, calcium phosphate precipitation, DEAE-dextran transfection or lipofection. In order to express the PH20 variant or fragment thereof of the present invention, various combinations of expression vectors and host cells can be employed. The preferred expression vector for eukaryotic cells comprises expression regulatory sequences derived from, but not limited to, SV40, bovine papillomavirus, adenovirus, adeno-associated virus, cytomegalovirus and retrovirus. The expression vector, which can be used for bacterial hosts, comprises bacterial plasmids, such as, pET, pRSET, pBluescript, pGEX2T, pUC vector, col E1, pCR1, pBR322, pMB9 and the derivatives thereof, obtained from *E. coli*; a plasmid having broad host range, such as, RP4; phage DNAs exemplified by various phage lambda derivatives, such as, λgt10, λgt11 and NM989; and other DNA phages, such as, M13 and filamentous single-stranded DNA phage. The expression vector available for yeast cells may be 2 °C. plasmid and its derivatives. The expression vector for insect cells is pVL941.

In a further aspect, the present invention relates to a method for producing a PH20 variant or fragment thereof, the method comprising a step of culturing the host cell and expressing the PH20 variant or fragment thereof according to the present invention.

When a recombinant expression vector capable of expressing the PH20 variant or fragment thereof is introduced into mammalian host cells, the PH20 variant or fragment thereof can be produced by culturing the host cells for a period of time such that the PH20 variant or fragment thereof is expressed in the host cells, preferably a sufficient period of time such that the PH20 variant is secreted into the medium during culture of the host cells.

In some cases, the expressed PH20 variant can be isolated from the host cells and purified to homogeneity. Isolation or purification of the PH20 variant can be performed by conventional isolation/purification methods (e.g., chromatography) that are used for proteins. The chromatography may be one or more combinations selected from affinity chromatography, ion exchange chromatography, and hydrophobic chromatography, but is not limited thereto. In addition to the chromatography, a combination of filtration, ultrafiltration, salting out, dialysis, and the like may be used.

Hereinafter, the present invention will be described in further detail with reference to working examples. It will be obvious to a person having ordinary skill in the art that these working examples are illustrative purposes only and are not to be construed to limit or change the scope of the present invention.

Working Examples

Hereinafter, the present invention will be described in further detail with reference to working examples. It will be obvious to a person having ordinary skill in the art that these working examples are illustrative purposes only and are not to be construed to limit or change the scope of the present invention.

Working Example 1. Construction of PH20 Variants

For construction of PH20 variants, the cDNA (clone ID: hMU002604) of wild-type PH20 was purchased from the Korean Human Gene Bank. Wild-type PH20 encodes amino acids from L36 to S490. The PH20 gene was amplified by polymerase chain reaction (hereinafter referred to as PCR) and inserted into the XhoI and NotI restriction enzyme sites of a pcDNA3.4-TOPO vector. For expression in ExpiCHO cells, the signal peptide of human growth hormone, human serum albumin or human Hyal1 was used as a signal peptide instead of the original signal peptide of PH20. For protein purification using a HisTrap column, the DNA sequence of a 6×His-tag was located at the 3'-end of the PH20 cDNA. The amino acid substitution of PH20 variants was performed using PCR method, and the amino acid substitution was confirmed by DNA sequencing.

The list of primers used in cloning of the PH20 variants are summarized in Table 9 below, and the specific sequences of the primers are summarized in Table 10 below.

TABLE 9

List of primers used in cloning of PH20 variants

| Clone | Primer 1 | Primer 2 | Primer 3 |
|---|---|---|---|
| cB4202 | ALB-SP-Xho | ALB-PH20-MR | SPAM1-6H-Not |
| cB4203-HM1 | ALB-SP-Xho | PH20_M345-364-F | SPAMl-6H-not |
| cB4203-HM2 | ALB-SP-Xho | PH20_Y365-L380-F | SPAM1-7H-not |
| cB4203-HM3 | ALB-SP-Xho | PH20_M345-L380-F | SPAM1-8H-not |
| cB4203-HM4 | ALB-SP-Xho | B4203-HM4-F | SPAM1-9H-not |
| cB4203-HM5 | ALB-SP-Xho | B4203-HM5-F | SPAM1-10H-not |
| cB4203-HM6 | ALB-SP-Xho | PH20-G363N | SPAM1-6H-not |
| cB4203-HM7 | ALB-SP-Xho | PH20-G363N | SPAM1-12H-not |
| cB4203-HM8 | ALB-SP-Xho | cB4203-HM8-M | SPAM1-13H-not |
| cB4203-HM9 | ALB-SP-Xho | cB4203-HM9-M | SPAM1-14H-not |
| cB4203-HM10 | ALB-SP-Xho | cB4203-HM10-M | SPAM1-6H-Not |
| cB4203-HM11 | ALB-SP-Xho | 4203-HM11 | SPAM1-16H-not |
| cB4203-HM12 | ALB-SP-Xho | 4203-HM12 | SPAM1-17H-not |
| cB4203-HM13 | ALB-SP-Xho | SASP-LN-del-R | SPAM1-18H-not |
| cB4203-HM14 | ALB-SP-Xho | — | I465-6H-not |
| cB4203-HM15 | ALB-SP-Xho | — | F468-6H-not |
| cB4203-HM16 | ALB-SP-Xho | — | P471-6H-not |
| cB4203-HM17 | ALB-SP-Xho | PH20-HM17 | SPAM1-22H-not |
| cB4203-HM18 | ALB-SP-Xho | PH20-HM18 | SPAM1-23H-not |
| cB4203-HM19 | ALB-SP-Xho | SASP-LN-del-R | K470-6H-not |
| cB4003-HP19 | ALB-SP-Xho | K470-not | |
| cB4203-HM20 | ALB-SP-Xho | SASP-LN-del-R | F468-6H-not |
| cB4003-HP20 | ALB-SP-Xho | F468-not | |
| cB4203-HM21 | ALB-SP-Xho | M21-mega-F | SPAM1-6H-Not |
| cB4203-HM24 | ALB-SP-Xho | M24-R | SPAM1-6H-not |
| cB4203-HM25 | ALB-SP-Xho | M25-R | SPAM1-6H-not |
| cB4203-HM26 | ALB-SP-Xho | B4-HM26 | SPAM1-6H-not |
| cB4203-HM27 | ALB-SP-Xho | B4-HM27 | SPAM1-6H-not |
| cB4203-HM28 | ALB-SP-Xho | B4-HM28 | SPAM1-6H-not |
| cB4203-HM29 | ALB-SP-Xho | B4-HM29 | |
| cB4203-HM30 | ALB-SP-Xho | B4-HM30 | |
| cB4203-HM31 | ALB-SP-Xho | B4-HM31 | |
| cB4203-HM32 | ALB-SP-Xho | B4-HM32 | |
| cB4203-HM33 | ALB-SP-Xho | B4-m33 | |
| cB4003-HP34 | ALB-SP-Xho | M21-mega-F | K470-not |
| cB4203-HM35 | ALB-SP-Xho | SASP-LN-del-R | P472-6H-not |
| cB4003-HP35 | ALB-SP-Xho | P472-not | |
| cB4203-HM36 | ALB-SP-Xho | SASP-LN-del-R | M473-6H-not |
| cB4003-HP36 | ALB-SP-Xho | M473-not | |
| cB4203-HM37 | ALB-SP-Xho | SASP-LN-del-R | E474-6H-not |
| cB4003-HP37 | ALB-SP-Xho | E474-not | |
| cB4203-HM38 | ALB-SP-Xho | SASP-LN-del-R | T475-6H-not |
| cB4003-HP38 | ALB-SP-Xho | T475-not | |
| cB4203-HM39 | ALB-SP-Xho | SASP-LN-del-R | E476-6H-not |
| cB4003-HP39 | ALB-SP-Xho | SASP-LN-del-R | E476-not |
| cB4203-HM40 | ALB-SP-Xho | M40-mega | SPAM1-6H-Not |
| cB4203-HM41 | ALB-SP-Xho | M41-mega | SPAM1-6H-Not |
| cB4203-HM42 | ALB-SP-Xho | m42-mega | SPAM1-6H-not |
| cB4203-HM43 | ALB-SP-Xho | I465-6H-not | |
| cB4203-HM44 | ALB-SP-Xho | D466-6H-not | |
| cB4203-HM45 | ALB-SP-Xho | B4-HM29 | |
| cB4003-HP46 | ALB-SP-Xho | F468-Not | |
| cB4203-HM47 | ALB-SP-Xho | P478-H-Not | |
| cB4203-HM48 | ALB-SP-Xho | I480-H-Not | |
| cB4203-HM49 | ALB-SP-Xho | Y482-H-Not | |

TABLE 9-continued

List of primers used in cloning of PH20 variants

| Clone | Primer 1 | Primer 2 | Primer 3 |
|---|---|---|---|
| cB4203-HM50 | ALB-SP-Xho | A484-H-not | |
| cB4203-HM51 | ALB-SP-Xho | P4-8-6-H-not | |
| cB4203-HM52 | ALB-SP-Xho | SASP-LN-del-R | T488-H-not |

TABLE 10

Primer sequences used in cloning of PH20 variants

| Primer | SEQ NO. | Nucleotide Sequences (5' -> 3') |
|---|---|---|
| ALB-SP-Xho | 6 | GAA TAT CTC GAG GCC ACC ATG AAG TGG GTT ACA |
| SPAM1-6H-Not | 7 | CTA ATT GCG GCC GCT CAT TAG TGG TGA TGG TGA TGA TGG AG AAA CCA ATT CTG C |
| ALB-PH20-MR | 8 | TAA CAG GAG GTG CTC TGA AAT TCA GAG AGT AAG CAG AGG AG |
| PH20_M345-P364-F | 9 | ATG GGG AAC CCT CAG TAT AAC AAG AAC CAA GGA ATC ATG TCA GGC CAT CAA GGA GTA TAT GGA CAC TAC ACT GGG GCC CTA CAT AAT CAA CGT CAC AC |
| PH20_Y365-L380-F | 10 | ATG GAG ACT ATA CTG AAT CCT TTC ATC CTG AAC GTG ACC AGT GGG GCC CTT CTC TGC AGT CAA GCC CTG TGC CAG GAG CAA GGA GTG TG |
| PH20_M345-L380-F* | 11 | ATG GAC ACT ACA CTG GGG CCC TTC ATC CTG AAC GTG ACC AGT GGG GCC CTT CTC TGC AGT CAA GCC CTG TGC CAG GAG CAA GGA GTG TG |
| B4203-HM4-F | 12 | ACT GTT GCT CTG GGT GCT TCT GGA ATT GTA ATA TGG GTA AGC TGG GAA AAT ACA AGA ACC AG GAA TCA TGT CA |
| B4203-HM5-F | 13 | AGC AAG GAG TGT GTA TAA GGA AAA CCA GCC ACC CAA AAG ACT ATC TTC ACC TCA ACC CAG A |
| PH20-G363N | 14 | AGT ATA TGG ACA CTA CAC TGA ACC CCT ACA TAA TCA ACG TCA C |
| cB4203-HM8-M | 15 | ATT GTA ATA TGG GGA ACC CTC AGT AAT ACA AGA ACC AG GAA TC |
| cB4203-HM9-M | 16 | ATT GTA ATA TGG GGA ACC CTC GAA AAT ACA AGA ACC AAG GAA TC |
| cB4203-HM10-M | 17 | ATT GTA ATA TGG GGA ACC TGG GAA AAT ACA AGA ACC AG GAA TC |
| 4203-HM11 | 18 | ACA CTA CAC TGA ACC CCT TCA TAC TCA ACG TCA CCC TAG CAG CCA |
| 4203-HM12 | 19 | ACA CTA CAC TGA ACC CCT TCA TAC TCA ACG TCA CCC TAT CAG GCA AAA TGT GTA GCC AAG TGC |
| SASP-LN-del-R | 20 | TAA CAG GAG GTG CTC TGA AAG AGT AAG CAG AGG AG |
| I465-6H-not | 21 | CTA ATT GCG GCC GCT CAT TAG TGG TGA TGG TGA TGA TGT ATA CAG ACA CCA TCA GC |
| F468-6H-not | 22 | CTA ATT GCG GCC GCT CAT TAG TGG TGA TGG TGA TGA TGA AAA GCA TCT ATA CAG ACA CC |
| P471-6H-not | 23 | CTA ATT GCG GCC GCT CAT TAG TGG TGA TGG TGA TGA TGA GGT TTT AGA AAA GCA TCT ATA C |

TABLE 10-continued

Primer sequences used in cloning of PH20 variants

| Primer | SEQ NO. | Nucleotide Sequences (5' -> 3') |
|---|---|---|
| PH20-HM17 | 24 | TCC AGG CCC AGA GGA AAG GCC GGT TGG GTA GCA AGG GGC CCC TAA AAG AGT AAG CAG AGG AG |
| PH20-HM18 | 25 | TCA CTT GGG GCA TTC CAG ACG GTG GTG AAG GGC CGG TTG GGT AGC AAG GGG CCC CTA AAA GAG TAA GCA GAG GAG |
| K470-not | 26 | CTA ATT GCG GCC GCT CAT TAG TGG TGA TGG TGA TGA TGT TTT AGA AAA GCA TCT ATA C |
| F468-not | 27 | CTA ATT GCG GCC GCT CAT TAA AAA GCA TCT ATA CAG ACA CC |
| M21-mega-F | 28 | AAT TGT AAT ATG GGG AAG CTG GGA AAA TAC AAG AA |
| M24-R | 29 | TGG AAT AAC AGG AGG TGC AGA GTA AGC AGA GGA GA |
| M25-R | 30 | TTT GGA ATA ACA GGA GAG TAA GCA GAG GAG A |
| B4-HM26 | 31 | AGT TTT GAA ATT CCT TTC TCT GGA TGA GCT GGA GCA CAG CCT GGG GGA GAG TGC GGC CCA GGG TGC TTC TGG AAT TG |
| B4-HM27 | 32 | ATG AGC TGG AGC ACA GCT TTG GGG AGA GTG CGG CCC AG |
| B4-HM28 | 33 | ATT CCT TTC TCA AGA TGA ACT TGA GCA CAG CTT TGG CGA AAC TGT TGC |
| B4-HM29 | 34 | CTA ATT GCG GCC GCT CAT TAG TGG TGA TGG TGA TGA TGA GCA TCT ATA CAG ACA CC |
| B4-HM30 | 35 | CTA ATT GCG GCC GCT CAT TAG TGG TGA TGG TGA TGA TGA CAG ACA CCA TCA GCA ATA C |
| B4-HM31 | 36 | CTA ATT GCG GCC GCT CAT TAG TGG TGA TGG TGA TGA TGA TCA GCA ATA CAC ACA TC |
| B4-HM32 | 37 | CTA ATT GCG GCC GCT CAT TAG TGG TGA TGG TGA TGA TGA CAC ACA TCA ACA GCA TC |
| B4-HM33 | 38 | CTA ATT GCG GCC GCT CAT TAG TGG TGA TGG TGA TGA TGA ACA GCA TCA GTG TCT TTT AC |
| P472-not | 39 | GTT ATA GCG GCC GCT CAT TAG GGA GGT TTT AGA AAA GCA TC |
| M473-not | 40 | GTT ATA GCG GCC GCT CAT TAC ATG GGA GGT TTT AGA AAA GCA TC |
| E474-not | 41 | GTT ATA GCG GCC GCT CAT TAC TCC ATG GGA GGT TTT AGA AAA GC |
| T475-not | 42 | GTT ATA GCG GCC GCT CAT TAT GTC TCC ATG GGA GGT TTT AG |
| M40-mega | 43 | TAA CAG GAG GTG CTC TGA AAT TAG AGT AAG CAG AGG AG |
| M41-mega | 44 | TGG AAT AAC AGG AGG TGC TCT AGA GTA AGC AGA GGA G |
| M42-mega | 45 | TTT GGA ATA ACA GGA GGA GAG TAA GCA GAG GAG |
| D466-6H-not | 46 | CTA ATT GCG GCC GCT CAT TAG TGG TGA TGG TGA TGA TGA TCT ATA CAG ACA CCA TCA GC |
| P478-H-Not | 47 | GAT AAT GCG GCC GCT CAT TAG TGG TGA TGG TGA TGA TGA GGT TCT TCT GTC TCC ATG GG |

TABLE 10-continued

Primer sequences used in cloning of PH20 variants

| Primer | SEQ NO. | Nucleotide Sequences (5' -> 3') |
|---|---|---|
| I480-H-Not | 48 | GAT AAT GCG GCC GCT CAT TAG TGG TGA TGG TGA TGA TGA ATT TGA GGT TCT TCT GTC TCC |
| Y482-H-Not | 49 | GAT AAT GCG GCC GCT CAT TAG TGG TGA TGG TGA TGA TGG TAG AAA ATT TGA GGT TCT TCT G |
| A484-H-not | 50 | GAT AAT GCG GCC GCT CAT TAG TGG TGA TGG TGA TGA TGA GCA TTG TAG AAA ATT TGA GGT TC |
| P486-H-not | 51 | GAT AAT GCG GCC GCT CAT TAG TGG TGA TGG TGA TGA TGG GGT GAA GCA TTG TAG AAA ATT TGA GG |
| T488-H-not | 52 | GAT AAT GCG GCC GCT CAT TAG TGG TGA TGG TGA TGA TGT GTG GAG GGT GAA GCA TTG TAG |
| K470-6H-not | 53 | CTA ATT GCG GCC GCT CAT TAG TGG TGA TGG TGA TGA TGT TTT AGA AAA GCA TCT ATA C |
| P472-6H-not | 54 | GTT ATA GCG GCC GCT CAT TAG TGG TGA TGG TGA TGA TGG GGA GGT TTT AGA AAA GCA TC |
| M473-6H-not | 55 | GTT ATA GCG GCC GCT CAT TAG TGG TGA TGG TGA TGA TGC ATG GGA GGT TTT AGA AAA GCA TC |
| E474-6H-not | 56 | GTT ATA GCG GCC GCT CAT TAG TGG TGA TGG TGA TGA TGC TCC ATG GGA GGT TTT AGA AAA GC |
| T475-6H-not | 57 | GTT ATA GCG GCC GCT CAT TAG TGG TGA TGG TGA TGA TGT GTC TCC ATG GGA GGT TTT AG |
| E476-6H-not | 58 | GTT ATA GCG GCC GCT CAT TAG TGG TGA TGG TGA TGA TGT TCT GTC TCC ATG GGA GG |
| E476-not | 59 | GTT ATA GCG GCC GCT CAT TAT TCT GTC TCC ATG GGA GG |

After finding the PH20 variant with increased enzymatic activity and thermal stability, the 6×His-tag-free cDNA of the PH20 variant was also constructed.

When the cell density of ExpiCHO cells reached $6 \times 10^6$/mL, a plasmid comprising the wild-type or variant PH20 cDNA inserted in the pcDNA3.4-TOPO vector was transfected into the ExpiCHO cells by ExpiFectamine CHO reagent. As a cell culture medium, ExpiCHO expression medium (100 to 500 mL) was used. After transfection, the ExpiCHO cells were shake-cultured at 130 rpm for a total of 6 days, during which the cells were cultured at 37° C. for 1 day and further cultured at lower temperature of 32° C. for 5 days. After completion of the culture, the cell supernatant was collected by centrifugation at 10,000 rpm for 30 min.

The recombinant proteins of the C-terminal 6×His-attached wild-type PH20 and variant PH20, produced in the ExpiCHO cells, were purified in three steps (performed using a HisTrap column, a Q Sepharose column and a Phenyl column, respectively) by an AKTA prime system.

For protein purification using the HisTrap column, buffer A (20 mM sodium phosphate, pH 7.5, 0.5 M NaCl) and buffer B (20 mM sodium phosphate, pH 7.5, 0.5 M NaCl, 0.5 M imidazole) were prepared. The protein was bound to the HisTrap column, and the column was flushed with 5 column volumes (CV) of buffer A to remove non-specifically bound proteins. It was confirmed that the conductivity was maintained at constant level, the column was flushed with 5 CV of 20% buffer B to elute the protein. The eluted protein was dialyzed with dialysis buffer (20 mM sodium phosphate, pH 7.5, 50 mM NaCl). For protein purification using the Q Sepharose column, buffer A (20 mM sodium phosphate, pH 7.5) and buffer B (20 mM sodium phosphate, pH 7.5, 0.5 M NaCl) were prepared. The protein was bound to the Q Sepharose column, and the column was flushed with 5 CV of buffer A to remove nonspecifically bound proteins, and then 5 CV of buffer B was flushed at concentration gradient of 0 to 100% to elute the protein.

For protein purification using the phenyl column, buffer A (20 mM sodium phosphate, pH 7.0, 1.5 M $(NH_4)_2SO_4$) and buffer B (20 mM sodium phosphate, pH 7.0) were prepared. The protein was bound to the phenyl column, and the column was flushed with 5 CV of buffer A to remove nonspecifically bound proteins, and then 5 CV of buffer B was flushed at concentration gradient of 0 to 100% to elute the protein.

The enzymatic activities of wild-type PH20 and variant PH20 were measured by turbidimetric assay, substrate-gel assay, and Morgan-Elson assay.

The turbidimetric assay is a method of measuring the absorbance in the precipitate produced when hyaluronic acid is mixed with albumin (BSA). When hyaluronic acid is hydrolyzed by PH20, the absorbance of the precipitate produced when mixed with albumin decreases. Hyaluronidase PH20 (Sigma) was diluted to 1, 2, 5, 7.5, 10, 15, 20, 30, 50 and 60 units/mL, and prepared in each tube. The purified protein sample was dissolved in enzyme diluent buffer (20 mM Tris.HCl, pH 7.0, 77 mM NaCl, 0.01% (w/v) bovine serum albumin) and diluted to 100×, 300×, 600×, 1200× and 2400× and prepared in each tube. In fresh tubes, the hyaluronic acid solution having a concentration of 3 mg/mL was diluted 10-fold to a concentration of 0.3 mg/mL so that the volume of each tube became 180 μL. 60 μL of enzyme was added to and mixed with the diluted hyaluronic acid solution and allowed to react at 37° C. for 45 min. After completion of the reaction, 50 μL of the reacted enzyme and 250 μL of acidic albumin solution were added to each well of a 96-well plate and shaken for 10 min, and then the absorbance was measured at 600 nm by spectrophotometer.

In the substrate-gel assay, the protein was electrophoresed on 10% SDS gel (including 0.17 mg/mL hyaluronic acid) for 1 h, and SDS was removed with 2.5% Triton X-100 (w/v) at 4° C. for 2 h. Thereafter, an enzymatic reaction was performed in the buffer (50 mM sodium phosphate, pH 7.0, 150 mM NaCl) at 37° C. (which is the optimum temperature for PH20) for 1 to 4 h, and the protein was stained with 0.5% Alcian blue reagent. Alcian blue reagent not bound to the hyaluronic acid was removed using de-staining solution. The SDS gel stained with Alcian blue was imaged, and then the band was quantified.

The thermal stability of the protein was measured by a method of measuring the aggregation temperature by dynamic light scattering (DLS), a method of measuring the melting temperature ($T_m$) in real-time PCR using Sypro-Orange dye, a method of measuring the enzymatic activity after leaving the protein to stand at predetermined temperature for a predetermined time, etc. In the method of measuring the aggregation temperature by DLS, the aggregation of molecules is measured using light scattering, and thus the sensitivity is high, and the aggregation temperature is generally lower than the melting temperature of the protein ($T_m$).

The sequences of the substituted or truncated amino acids in the PH20 variants constructed in the present invention are shown in Table 11 below.

Among the variants according to the present invention, the variant having the 6×His-tag attached to the C-terminus of PH20 was named HM; the variant free of the 6×His-tag was named HP; mature wild-type PH20 (L36 to S490) having the 6×His-tag attached to the C-terminus was named WT; and mature wild-type PH20 (L36 to Y482) having the C-terminus truncated after Y482 while being free of the 6×His-tag was named HW2.

TABLE 11

Amino acid sequences of PH20 variants according to the present invention and substitution/cleavage characteristics thereof

| Name | SEQ NO. | Substitution | Amino Acid Sequence |
|---|---|---|---|
| HM1 | 60 | 12 amino acids substitution of M345T, S347T, M348K, K349E, L352Q, L353A, L354I, D355K, N356E, E359D, I361T and N363G. | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGILSITRTKES CQAIKEYMDTTLGPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM2 | 61 | 7 amino acids substitution of Y365F, I367L, L371S, A372G, K374L, M375L and V379A | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGILSITRTKES CQAIKEYMDTTLNPFILNVISGALLCSQALCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM3 | 62 | 19 amino acids substitution of M345T, S347T, M348K, K349E, L352Q, L353A, L354I, D355K, N356E, E359D, I361T, N363G, Y365F, I367L, L371S, A372G, K374L, M375L and V379A | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGILSITRTKES CQAIKEYMDTTLGPFILNVISGALLCSQALCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| HM4 | 63 | 17 amino acids substitution of G340V, T341S, L342W, S343E, I344N, M345T, S347T, M348K, K349E, L352Q, L353A, L354I, D355K, N356E, E359D, I361T and N363G | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWVSWENTRTKES CQAIKEYMDTTLGPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM6 | 64 | 11 amino acids substitution of M345T, S347T, M348K, K349E, L352Q, L353A, L354I, D355K, N356E, E359D and I361T | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLSITRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM7 | 65 | 16 amino acids substitution of G340V, T341S, L342W, S343E, I344N, M345T, S347T, M348K, K349E, L352Q, L353A, L354I, D355K, N356E, E359D and I361T | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWVSWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM8 | 66 | 12 amino acids substitution of I344N, M345T, S347T, M348K, K349E, L352Q, L353A, L354I, D355K, N356E, E359D and I361T | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLSNTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM9 | 67 | 13 amino acids substitution of S343E, I344N, M345T, S347T, M348K, K349E, L352Q, L353A, L354I, D355K, N356E, E359D and I361T | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| HM10 | 68 | 14 amino acids substitution of L342W, S343E, I344N, M345T, S347T, M348K, K349E, L352Q, L353A, L354I, D355K, N356E, E359D and I361T | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM11 | 69 | 13 amino acids substitution of M345T, S347T, M348K, K349E, L352Q, L353A, L354I, D355K, N356E, E359D, I361T, Y365F and I367L | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLSITRTKES CQAIKEYMDTTLNPFILNVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM12 | 70 | 15 amino acids substitution of M345T, S347T, M348K, K349E, L352Q, L353A, L354I, D355K, N356E, E359D, I361T, Y365F, I367L, L371S and A372G | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLSITRTKES CQAIKEYMDTTLNPFILNVISGAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM13 | 71 | 11 amino acids substitution of M345T, S347T, M348K, K349E, L352Q, L353A, L354I, D355K, N356E, E359D and I361T, and truncation before F38 at the N-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGTLSITRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETEEPQIFYNASPSTLS |
| HM14 | 72 | 11 amino acids substitution of M345T, S347T, M348K, K349E, L352Q, L353A, L354I, D355K, N356E, E359D and I361T, and truncation after I465 at the C-terminus | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLSITRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCI |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| HM15 | 73 | 11 amino acids substitution of M345T, S347T, M348K, K349E, L352Q, L353A, L354I, D355K, N356E, E359D and I361T, and truncation after F468 at the C-terminus | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLSITRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAF |
| HM16 | 74 | 11 amino acids substitution of M345T, S347T, M348K, K349E, L352Q, L353A, L354I, D355K, N356E, E359D and I361T, and truncation after P471 at the C-terminus | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGTLSITRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKP |
| HM17 | 75 | Substitution of L36~V47 with FRGPLLPNR, and amino acids substitution of M345T, S347T, M348K, K349E, L352Q, L353A, L354I, D355K, N356E, E359D and I361T | FRGPLLPNRPFLWAWNAPSEFCLGKFDEPLDMSLF SFIGSPRINATGQGVTIFYVDRLGYYPYIDSITGV TVNGGIPQKISLQDHLDKAKKDITFYMPVDNLGMA VIDWEEWRPTWARNWKPKDVYKNRSIELVQQQNVQ LSLTEATEKAKQEFEKAGKDFLVETIKLGKLLRPN HLWGYYLFPDCYNHHYKKPGYNGSCFNVEIKRNDD LSWLWNESTALYPSIYLNTQQSPVAATLYVRNRVR EAIRVSKIPDAKSPLPVFAYTRIVFTDQVLKFLSQ DELVYTFGETVALGASGIVIWGILSITRTKESCQA IKEYMDTTLNPYIINVTLAAKMCSQVLCQEQGVCI RKNWNSSDYLHLNPDNFAIQLEKGGKFTVRGKPTL EDLEQFSEKFYCSCYSTLSCKEKADVKDTDAVDVC IADGVCIDAFLKPPMETEEPQIFYNASPSTLS |
| HM18 | 76 | Substitution of L36~A52 with FRGPLLPNRPFTTV, and amino acids substitution of M345T, S347T, M348K, K349E, L352Q, L353A, L354I, D355K, N356E, E359D and I361T | FRGPLLPNRPFTTVWNAPSEFCLGKFDEPLDMSLF SFIGSPRINATGQGVTIFYVDRLGYYPYIDSITGV TVNGGIPQKISLQDHLDKAKKDITFYMPVDNLGMA VIDWEEWRPTWARNWKPKDVYKNRSIELVQQQNVQ LSLTEATEKAKQEFEKAGKDFLVETIKLGKLLRPN HLWGYYLFPDCYNHHYKKPGYNGSCFNVEIKRNDD LSWLWNESTALYPSIYLNTQQSPVAATLYVRNRVR EAIRVSKIPDAKSPLPVFAYTRIVFTDQVLKFLSQ DELVYTFGETVALGASGIVIWGILSITRTKESCQA IKEYMDTTLNPYIINVTLAAKMCSQVLCQEQGVCI RKNWNSSDYLHLNPDNFAIQLEKGGKFTVRGKPTL EDLEQFSEKFYCSCYSTLSCKEKADVKDTDAVDVC IADGVCIDAFLKPPMETEEPQIFYNASPSTLS |
| HM19 | 77 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after K470 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLK |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| HM20 | 78 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after F468 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAF |
| HM21 | 79 | 15 amino acids substitution of T341S, L342W, S343E, I344N, M345T, S347T, M348K, K349E, L352Q, L353A, L354I, D355K, N356E, E359D and I361T | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGSWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM24 | 80 | 11 amino acids substitution of M345T, S347T, M348K, K349E, L352Q, L353A, L354I, D355K, N356E, E359D and I361T, and truncation before A40 at the N-terminus | APPVIPNVPFLWAWNAPSEFCLGKFDEPLDMSLFS FIGSPRINATGQGVTIFYVDRLGYYPYIDSITGVT VNGGIPQKISLQDHLDKAKKDITFYMPVDNLGMAV IDWEEWRPTWARNWKPKDVYKNRSIELVQQQNVQL SLTEATEKAKQEFEKAGKDFLVETIKLGKLLRPNH LWGYYLFPDCYNHHYKKPGYNGSCFNVEIKRNDDL SWLWNESTALYPSIYLNTQQSPVAATLYVRNRVRE AIRVSKIPDAKSPLPVFAYTRIVFTDQVLKFLSQD ELVYTEGETVALGASGIVIWGILSITRTKESCQAI KEYMDTTLNPYIINVTLAAKMCSQVLCQEQGVCIR KNWNSSDYLHLNPDNFAIQLEKGGKFTVRGKPTLE DLEQFSEKFYCSCYSTLSCKEKADVKDTDAVDVCI ADGVCIDAFLKPPMETEEPQIFYNASPSTLS |
| HM25 | 81 | 11 amino acids substitution of M345T, S347T, M348K, K349E, L352Q, L353A, L354I, D355K, N356E, E359D and I361T, truncation before P42 at the N-terminus | PVIPNVPFLWAWNAPSEFCLGKFDEPLDMSLFSFI GSPRINATGQGVTIFYVDRLGYYPYIDSITGVIVN GGIPQKISLQDHLDKAKKDITFYMPVDNLGMAVID WEEWRPTWARNWKPKDVYKNRSIELVQQQNVQLSL TEATEKAKQEFEKAGKDFLVETIKLGKLLRPNHLW GYYLFPDCYNHHYKKPGYNGSCFNVEIKRNDDLSW LWNESTALYPSIYLNTQQSPVAATLYVRNRVREAI RVSKIPDAKSPLPVFAYTRIVFTDQVLKFLSQDEL VYTEGETVALGASGIVIWGILSITRTKESCQAIKE YMDTTLNPYIINVTLAAKMCSQVLCQEQGVCIRKN WNSSDYLHLNPDNFAIQLEKGGKFTVRGKPTLEDL EQFSEKFYCSCYSTLSCKEKADVKDTDAVDVCIAD GVCIDAFLKPPMETEEPQIFYNASPSTLS |
| HM29 | 82 | 14 amino acids substitution of L342W, S343E, I344N, M345T, S347T, M348K, K349E, L352Q, L353A, L354I, D355K, N356E, | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| | | E359D and I361T, truncation before L36 at the N-terminus, and truncation after A467 at the C-terminus | LSQDELVYTEGETVALGASGIVIWGTWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDA |
| HM30 | 83 | 14 amino acids substitution of L342W, S343E, I344N, M345T, S347T, M348K, K349E, L352Q, L353A, L354I, D355K, N356E, E359D and I361T, truncation before L36 at the N-terminus, and truncation after C464 at the C-terminus | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTEGETVALGASGIVIWGTWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVC |
| HM31 | 84 | 14 amino acids substitution of L342W, S343E, I344N, M345T, S347T, M348K, K349E, L352Q, L353A, L354I, D355K, N356E, E359D and I361T, truncation before L36 at the N-terminus, and truncation after D461 at the C-terminus | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTEGETVALGASGIVIWGTWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIAD |
| HM32 | 85 | 14 amino acids substitution of L342W, S343E, I344N, M345T, S347T, M348K, K349E, L352Q, L353A, L354I, D355K, N356E, E359D and I361T, truncation before L36 at the N-terminus, and truncation after C458 at the C-terminus | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTEGETVALGASGIVIWGTWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVC |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| HM33 | 86 | 14 amino acids substitution of L342W, S343E, I344N, M345T, S347T, M348K, K349E, L352Q, L353A, L354I, D355K, N356E, E359D and I361T, truncation before L36 at the N-terminus, and truncation after V455 at the C-terminus | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTEGETVALGASGIVIWGTWENTRTKES CQAIKEYMDTTLNPYIINVTLAAKMCSQVLCQEQG VCIRK̄NWN̄S̄SDYLHLNPDNFAIQLEKGGKFTVRGK PTLEDLEQFSEKFYCSCYSTLSCKEKADVKDTDAV |
| HP34 | 87 | 15 amino acids substitution of T341S, L342W, S343E, I344N, M345T, S347T, M348K, K349E, L352Q, L353A, L354I, D355K, N356E, E359D and I361T, truncation before F38 at the N-terminus, and truncation after K470 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGSWENTRTKESCQ AIKEYMDTT**LNPYIINVTLAAKMCSQVLCQEQGVC IRK̄NWN̄S̄SDYLHLNPDNFAIQLEKGGKFTVRGKPT LEDLEQFSEKFYCSCYSTLSCKEKADVKDTDAVDV CIADGVCIDAFLK |
| HM35 | 88 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after P472 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGTWENTRTKESCQ AIKEYMDTTLNPYIINVTLAAKMCSQVLCQEQGVC IRK̄NWN̄S̄SDYLHLNPDNFAIQLEKGGKFTVRGKPT LEDLEQFSEKFYCSCYSTLSCKEKADVKDTDAVDV CIADGVCIDAFLKPP |
| HM36 | 89 | 14 amino acids substitution of L342W, S343E, I344N, M345T, S347T, M348K, K349E, L352Q, L353A, L354I, D355K, N356E, E359D and I361T, truncation before F38 at the N-terminus, | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGTWENTRTKESCQ AIKEYMDTTLNPYIINVTLAAKMCSQVLCQEQGVC IRK̄NWN̄S̄SDYLHLNPDNFAIQLEKGGKFTVRGKPT LEDLEQFSEKFYCSCYSTLSCKEKADVKDTDAVDV CIADGVCIDAFLKPPM |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| | | and truncation after M473 at the C-terminus | |
| HM37 | 90 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after E474 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPME |
| HM38 | 91 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after T475 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMET |
| HM39 | 92 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after E476 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETE |
| HM40 | 93 | 11 amino acids substitution of M345T, S347T, M348K, K349E, L352Q, L353A, L354I, D355K, N356E, E359D | NFRAPPVIPNVPFLWAWNAPSEFCLGKFDEPLDMS LFSFIGSPRINATGQGVTIFYVDRLGYYPYIDSIT GVTVNGGIPQKISLQDHLDKAKKDITFYMPVDNLG MAVIDWEEWRPTWARNWKPKDVYKNRSIELVQQQN VQLSLTEATEKAKQEFEKAGKDFLVETIKLGKLLR PNHLWGYYLFPDCYNHHYKKPGYNGSCFNVEIKRN DDLSWLWNESTALYPSIYLNTQQSPVAATLYVRNR |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| | | and I361T, and truncation before N37 at the N-terminus | VREAIRVSKIPDAKSPLPVFAYTRIVFTDQVLKFL SQDELVYTEGETVALGASGIVIWGILSITRTKESC QAIKEYMDTTLNPYIINVTLAAKMCSQVLCQEQGV CIRKNWNSSDYLHLNPDNFAIQLEKGGKFTVRGKP TLEDLEQFSEKFYCSCYSTLSCKEKADVKDTDAVD VCIADGVCIDAFLKPPMETEEPQIFYNASPSTLS |
| HM41 | 94 | 11 amino acids substitution of M345T, S347T, M348K, K349E, L352Q, L353A, L354I, D355K, N356E, E359D and I361T, and truncation before R39 at the N-terminus | RAPPVIPNVPFLWAWNAPSEFCLGKFDEPLDMSLF SFIGSPRINATGQGVTIFYVDRLGYYPYIDSITGV TVNGGIPQKISLQDHLDKAKKDITFYMPVDNLGMA VIDWEEWRPTWARNWKPKDVYKNRSIELVQQQNVQ LSLTEATEKAKQEFEKAGKDFLVETIKLGKLLRPN HLWGYYLFPDCYNHHYKKPGYNGSCFNVEIKRNDD LSWLWNESTALYPSIYLNTQQSPVAATLYVRNRVR EAIRVSKIPDAKSPLPVFAYTRIVFTDQVLKFLSQ DELVYTEGETVALGASGIVIWGILSITRTKESCQA IKEYMDTTLNPYIINVTLAAKMCSQVLCQEQGVCI RKNWNSSDYLHLNPDNFAIQLEKGGKFTVRGKPIL EDLEQFSEKFYCSCYSTLSCKEKADVKDTDAVDVC IADGVCIDAFLKPPMETEEPQIFYNASPSTLS |
| HM42 | 95 | 11 amino acids substitution of M345T, S347T, M348K, K349E, L352Q, L353A, L354I, D355K, N356E, E359D and I361T, and truncation before P41 at the N-terminus | PPVIPNVPFLWAWNAPSEFCLGKFDEPLDMSLFSF IGSPRINATGQGVTIFYVDRLGYYPYIDSITGVTV NGGIPQKISLQDHLDKAKKDITFYMPVDNLGMAVI DWEEWRPTWARNWKPKDVYKNRSIELVQQQNVQLS LTEATEKAKQEFEKAGKDFLVETIKLGKLLRPNHL WGYYLFPDCYNHHYKKPGYNGSCFNVEIKRNDDLS WLWNESTALYPSIYLNTQQSPVAATLYVRNRVREA IRVSKIPDAKSPLPVFAYTRIVFTDQVLKFLSQDE LVYTEGETVALGASGIVIWGILSITRTKESCQAIK EYMDTTLNPYIINVTLAAKMCSQVLCQEQGVCIRK NWNSSDYLHLNPDNFAIQLEKGGKFTVRGKPTLED LEQFSEKFYCSCYSTLSCKEKADVKDTDAVDVCIA DGVCIDAFLKPPMETEEPQIFYNASPSTLS |
| HM43 | 96 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after I465 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGSWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCI |
| HM44 | 97 | 14 amino acids substitution of L342W, S343E, I344N, M345T, S347T, M348K, K349E, L352Q, L353A, L354I, D355K, N356E, | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| | | E359D and I361T, truncation before F38 at the N-terminus, and truncation after D466 at the C-terminus | QDELVYTEGETVALGASGIVIWGSWENTRTKESCQAIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCID |
| HM45 | 98 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after A467 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGSWENTRTKESCQAIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDA |
| HP46 | 99 | 15 amino acids substitution of T341S, L342W, S343E, I344N, M345T, S347T, M348K, K349E, L352Q, L353A, L354I, D355K, N356E, E359D and I361T, truncation before F38 at the N-terminus, and truncation after F468 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGSWENTRTKESCQAIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAF |
| HM47 | 100 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after P478 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGTWENTRTKESCQAIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETEEP |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| HM48 | 101 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after I480 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETEEPQI |
| HM49 | 102 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after Y482 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETEEPQIFY |
| HM50 | 103 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after A484 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETEEPQIFYNA |
| HM51 | 104 | 14 amino acids substitution of L342W, S343E, I344N, M345T, S347T, M348K, K349E, L352Q, L353A, L354I, D355K, N356E, E359D and I361T, truncation before F38 at the N-terminus, | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETEEPQIFYNASP |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| | | and truncation after P486 at the C-terminus | |
| HM52 | 105 | 14 amino acids substitution of L342W, S343E, I344N, M345T, S347T, M348K, K349E, L352Q, L353A, L354I, D355K, N356E, E359D and I361T, truncation before F38 at the N-terminus, and truncation after T488 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGTWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAFLKPPMETEEPQIFYNASPST |
| HM53 | 106 | 15 amino acids substitution of T341G, L342W, S343E, I344N, M345T, S347T, M348K, K349E, L352Q, L353A, L354I, D355K, N356E, E359D and I361T, truncation before L36 at the N-terminus, and truncation after S490 at the C-terminus | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTFGETVALGASGIVIWGGWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM54 | 107 | 15 amino acids substitution of T341A, L342W, S343E, I344N, M345T, S347T, M348K, K349E, L352Q, L353A, L354I, D355K, N356E, E359D and I361T, truncation before L36 at the N-terminus, and truncation after S490 at the C-terminus | LNFRAPPVIPNVPFLWAWNAPSEFCLGKFDEPLDM SLFSFIGSPRINATGQGVTIFYVDRLGYYPYIDSI TGVTVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTEGETVALGASGIVIWGAWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HM55 | 108 | 15 amino acids substitution of T341C, L342W, S343E, I344N, M345T, S347T, M348K, K349E, L352Q, L353A, | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| | | L354I, D355K, N356E, E359D and I361T, truncation before L36 at the N-terminus, and truncation after S490 at the C-terminus | RVREAIRVSKIPDAKSPLPVFAYTRIVFTDQVLKF LSQDELVYTEGETVALGASGIVIWGCWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQ109IFYNASPS TLS |
| HM56 | 109 | 15 amino acids substitution of T341D, L342W, S343E, I344N, M345T, S347T, M348K, K349E, L352Q, L353A, L354I, D355K, N356E, E359D and I361T, truncation before L36 at the N-terminus, and truncation after S490 at the C-terminus | LNFRAPPVIPNVPFLWAWNAPSEFCLGKFDEPLDM SLFSFIGSPRINATGQGVTIFYVDRLGYYPYIDSI TGVIVNGGIPQKISLQDHLDKAKKDITFYMPVDNL GMAVIDWEEWRPTWARNWKPKDVYKNRSIELVQQQ NVQLSLTEATEKAKQEFEKAGKDFLVETIKLGKLL RPNHLWGYYLFPDCYNHHYKKPGYNGSCFNVEIKR NDDLSWLWNESTALYPSIYLNTQQSPVAATLYVRN RVREAIRVSKIPDAKSPLPVFAYTRIVFTDQVLKF LSQDELVYTEGETVALGASGIVIWGDWENTRTKES CQAIKEYMDTTLNPYIINVTLAAKMCSQVLCQEQG VCIRKNWNSSDYLHLNPDNFAIQLEKGGKFTVRGK PTLEDLEQFSEKFYCSCYSTLSCKEKADVKDTDAV DVCIADGVCIDAFLKPPMETEEPQIFYNASPSTLS |
| HP57 | 110 | 12 amino acids substitution of I344N, M345T, S347T, M348K, K349E, L352Q, L353A, L354I, D355K, N356E, E359D and I361T, truncation before F38 at the N-terminus, and truncation after F468 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGILSNTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAF |
| HP58 | 111 | 13 amino acids substitution of S343E, I344N, M345T, S347T, M348K, K349E, L352Q, L353A, L354I, D355K, N356E, E359D and I361T, truncation before F38 at the N-terminus, and truncation after F468 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGTLENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAF |
| HP59 | 112 | 15 amino acids substitution of T341A, L342W, | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM |

TABLE 11-continued

Amino acid sequences of PH20 variants according to the present invention and substitution/cleavage characteristics thereof

| Name | SEQ NO. | Substitution | Amino Acid Sequence |
|---|---|---|---|
| | | S343E, I344N, M345T, S347T, M348K, K349E, L352Q, L353A, L354I, D355K, N356E, E359D and I361T truncation before F38 at the N-terminus, and truncation after F468 at the C-terminus | AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGAWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAF |
| HP60 | 113 | 15 amino acids substitution of T341G, L342W, S343E, I344N, M345T, S347T, M348K, K349E, L352Q, L353A, L354I, D355K, N356E, E359D and I361T, truncation before F38 at the N-terminus, and truncation after F468 at the C-terminus | FRAPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTFGETVALGASGIVIWGGWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAF |
| HP61 | 114 | 16 amino acids substitution of A40G, T341S, L342W, S343E, I344N, M345T, S347T, M348K, K349E, L352Q, L353A, L354I, D355K, N356E, E359D and I361T, truncation before F38 at the N-terminus, and truncation after F468 at the C-terminus | FRGPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGSWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAF |
| HP62 | 115 | Removal of P42, 15 amino acids substitution of T341S, L342W, S343E, I344N, M345T, S347T, M348K, K349E, L352Q, L353A, L354I, D355K, N356E, E359D and I361T, truncation before F38 at the N-terminus, | FRGPPVIPNVPFLWAWNAPSEFCLGKFDEPLDMSL FSFIGSPRINATGQGVTIFYVDRLGYYPYIDSITG VTVNGGIPQKISLQDHLDKAKKDITFYMPVDNLGM AVIDWEEWRPTWARNWKPKDVYKNRSIELVQQQNV QLSLTEATEKAKQEFEKAGKDFLVETIKLGKLLRP NHLWGYYLFPDCYNHHYKKPGYNGSCFNVEIKRND DLSWLWNESTALYPSIYLNTQQSPVAATLYVRNRV REAIRVSKIPDAKSPLPVFAYTRIVFTDQVLKFLS QDELVYTEGETVALGASGIVIWGSWENTRTKESCQ AIKEYMDTTLNPYIINVTLAAKMCSQVLCQEQGVC IRKNWNSSDYLHLNPDNFAIQLEKGGKFTVRGKPT LEDLEQFSEKFYCSCYSTLSCKEKADVKDTDAVDV CIADGVCIDAF |

TABLE 11-continued

Amino acid sequences of PH20 variants according
to the present invention and substitution/cleavage
characteristics thereof

| Name | SEQ NO. | Substitution | Amino Acid Sequence |
|---|---|---|---|
| | | and truncation after F468 at the C-terminus | |

Working Example 2. Construction of PH20 Variants HM1 and HM6

As shown in FIG. 1 in part B thereof, amino acid residues M345 to N363 of PH20 correspond to the alpha-helix 8 region and the linker region between alpha-helix 7 and alpha-helix 8 in the protein tertiary structure model. Among the amino acids of alpha-helix 8, C351 forms a disulfide bond with C60 of alpha-helix 1; Y357 forms hydrophobic interaction with F315 of alpha-helix 7; and N363 forms a hydrogen bond with D69 of alpha-helix 1, thereby stabilizing secondary structures adjacent to alpha-helix 8 (FIG. 1 in part C thereof).

In order to construct variants having higher enzymatic activity and thermal stability than WT by substituting amino acids located in the alpha-helix 8 region of PH20 and the linker region between alpha-helix 7 and alpha-helix 8, the following variants were constructed: the variant HM1 in which 12 amino acids in the M345 to N363 region were substituted; the variant HM2 in which 7 amino acids in the Y365 to V379 region were substituted; and the variant HM3 in which 19 amino acids in the M345 to V379 region were substituted. Among the amino acids located in alpha-helix 8 of PH20, C351, which is involved in disulfide bonding, and Y357 which is involved in hydrophobic interaction, were not substituted. The substituted amino acid sequences in the variants HM1, HM2 and HM3 are shown in Table 11 above. When ExpiCHO cells were transfected with the pcDNA3.4-TOPO plasmid comprising the gene of the variant HM1, HM2 or HM3, the variant HM1 was expressed in the ExpiCHO cells (FIG. 3 in part a thereof), and the variants HM2 and HM3 were not expressed in the cells. Whether the protein was be expressed was confirmed not only by measurement of the enzymatic activity, but also by Western blot analysis using an antibody (Abcam, ab 193009) against human PH20. The epitope of the antibody is Q173 to P222 region. These experimental results suggest that amino acid substitution of Y365 to V379 region of the amino acid sequence of alpha-helix 8, used in construction of the variants HM2 and HM3, causes a serious effect on the protein structure; thus, the proteins of the variants HM2 and HM3 were not expressed. The expression level of the variant HM1 was 3.4-fold higher than that of wild-type WT (FIG. 2). The variant HM1 is one in which the hydrogen bond between N363 of alpha-helix 8 and D69 of alpha-helix 1 was removed by substituting N363 with glycine (FIG. 1 in part C thereof). To restore the hydrogen bond between N363 and D69, G363 in HM1 was substituted with asparagine, thereby constructing the variant HM6. The substituted amino acids in the variant HM6 are shown in Table 11 above.

The variant HM6 was expressed in ExpiCHO cells, and the expression level thereof was similar to that of the variant HM1 (the expression level was 3.4-fold higher than that of WT) (FIG. 2). When the enzymatic activity was measured by turbidimetric assay, it was shown that the enzymatic activity of the variant HM6 was 1.3-fold higher than that of WT (FIG. 3 in part B thereof). In the substrate-gel assay, generally, SDS is removed with 2.5% Triton X-100 (w/v) after SDS-PAGE, and enzymatic reaction is performed at 37° C. for 1 to 4 h, during which the extent to which hyaluronidase hydrolyzes hyaluronic acid is measured using Alcian blue dye. It is known that when SDS is removed from the substrate gel, protein refolding immediately occurs, and the substrate does not affect the protein refolding. When the enzymatic activities of WT and the variants HM1 and HM6 were measured by the substrate-gel assay at 37° C. for 1 to 4 h, HM6 exhibited higher enzymatic activity than those of WT and the variant HM1 (FIG. 3 in part C thereof). This result suggests that protein refolding of the variants HM1 and HM6 and the resulting renaturation were faster than those of WT and that the constructed variants exhibit higher enzymatic activity than WT. When the signal peptide of PH20 itself was used, the expression level of the protein in ExpiCHO cells was low, and to solve this problem, the signal peptide sequence of human serum albumin or human Hyal1 was used. As shown in FIG. 3 in part C thereof, when each of the signal peptides of human serum albumin and human Hyal1 was used as the signal peptide of the variant HM1, the expression of the protein increased, and there was no significant difference between the two signal peptides. When the enzymatic activity was measured by the substrate-gel assay, WT having the signal peptide of human serum albumin and the variant HM1 having the signal peptide of human serum albumin or Hyal1 exhibited enzymatic activity at the pH ranging from 5 to 8 (FIG. 3 in part D thereof). In the present invention, the signal peptide of human serum albumin was used as the signal peptide of the variant constructed after HM1.

When the thermal stabilities of WT and the variants HM1 and HM6 were compared based on the aggregation temperatures, the aggregation temperatures were 46.5° C., 53.0° C. and 50.5° C., respectively, indicating that the aggregation temperatures of the variants HM1 and HM6 were 6.5° C. and 4.0° C. higher, than that of WT, respectively (FIG. 10). The results of measuring the aggregation temperatures were consistent with the protein refolding results shown in the substrate-gel assay. These results suggest for the first time that the hydrogen bond formed by the N363 residue of alpha-helix 8 plays an important role in the thermal stability and enzymatic activity of PH20.

In addition, when the hydrophilic/hydrophobic natures of WT and the variants HM1 and HM6 were compared using a phenyl column chromatography, HM1 and HM6 were all eluted earlier than WT. This suggests that the variants HM1 and HM6 have a more hydrophilic nature than WT due to the substitution of the amino acids. However, the variants HM1 and HM6 eluted from the phenyl column showed two peaks, unlike WT, and exhibited the same molecular weight when treated with PNGase F. This appears to be a difference caused by N-glycosylation (FIG. 3 in part E thereof).

Working Example 3. Construction of PH20 Variants HM4, HM7, HM8, HM9, HM10, HM11 and HM12

It is believed that the fact that the amino acid substitution of the M345 to N363 and M345 to I361 regions by construction of the variants HM1 and HM6 in Working Example 2 resulted in an increase in both the enzymatic activity and thermal stability of PH20 has made great advances in terms of protein engineering. Thus, based on the variants HM1 and HM6, other amino acids in the N-terminal and C-terminal directions were additionally substituted.

First, the variants HM4 and HM7 were constructed, which comprise the substituted amino acids in the variants HM1 and HM6 and in which the amino acids between G340 and I344 were additionally substituted with G340V, T341S, L342W, S343E and I344N. The sequences of the substituted amino acid sequences in the variants HM4 and HM7 are shown in Table 11 above. The variants HM4 and HM7 were expressed in ExpiCHO cells. The results of protein purification for HM7 are shown in FIG. 5 in part A thereof. HM4 and HM7 showed an increase in protein expression of 6.3-fold compared to WT, and showed increases in aggregation temperature of 10° C. and 11.5° C., respectively, compared to WT. However, the enzymatic activities of HM4 and HM7, measured by turbidimetric assay, were merely about 15% of that of WT (FIG. 5 in part B thereof). Enzymatic activity and thermal stability generally have a trade-off relationship, but in the present invention, it appeared that the substitution introduced in the variants HM1 and HM6 increased the thermal stability of the variants while maintaining the enzymatic activity, and the enzymatic activities of the variants HM4 and HM7 decreased due to an excessive increase in the thermal stability. An increase in aggregation temperature of 11.5° C., which appeared in the variants HM4 and HM7 is a very significant result in terms of protein engineering. When the structural flexibilities of the proteins were analyzed by a Stern-Volmer plot, it was shown that the structural flexibilities of HM1, HM6, HM4 and HM7, obtained by substituting alpha-helix 8 and its linker region, were all higher than that of WT (FIG. 11 in part A thereof). This result suggests that the increase in local thermal stability resulted in an increase in the flexibility of the entire protein structure.

The difference between the variants HM6 and HM7 is amino acids between G340 and I344. In order to identify amino acids which are involved in the increased thermal stability of the variant HM7, the following variants were made based on the variant HM6: HM8 having substitution I344N; HM9 having substitutions S343 and I344N; HM10 having substitutions L342W, S343E and 344N; and HM21 having substitutions T341S, L342W, S343E and I344N. The sequences of the substituted amino acids in the variants HM8, HM9, HM10 and HM21 are shown in Table 11 above. The variants HM8, HM9, HM10 and HM21 were expressed in ExpiCHO cells (FIG. 5 in part A thereof). As I344N, S343E and L342W were introduced in the N-terminal direction of alpha-helix 8 based on the variant HM6, the aggregation temperatures of the variants HM8, HM9 and HM10 increased to 52.5° C., 53° C. and 55.5° C., respectively (FIG. 10). However, the variants HM8, HM9 and HM10 maintained enzymatic activities similar to that of WT (FIG. 5 in part B thereof). This result suggests that the amino acid substitutions introduced in the variants HM8, HM9 and HM10 had a local effect on the thermal stabilities of the enzymes but had no significant effect on the enzymatic activities. However, HM21 showed reduced thermal stability compared to HM10, but showed approximately 2-fold higher property compared to WT at pH 7.0. When WT and each variant were allowed to react with the substrate for 1 h in the substrate-gel assay, the enzymatic activity shown was in the order of HM21>HM10>HM9>HM8>HM6>WT (FIG. 5 in part C thereof).

When the physical properties of the variants HM7, HM8, HM9, HM10 and HM21 were examined using a phenyl column chromatography, these PH20 variants were eluted earlier than WT, suggesting that these variants all have a hydrophilic nature. However, the pattern of the main peak at the amino acid substitution position appeared differently (FIG. 5 in part D thereof).

The variant HM7 also showed two peaks in the phenyl column chromatography, like the variants HM1 and HM6, suggesting that two different types were present.

In order to examine the patterns of migration of WT and the variants depending on their isoelectric points, isoelectric focusing (hereinafter referred to as IEF) analysis was performed (FIG. 5 in part E thereof). On IEF gel, WT and the variant HM6 and HM8 showed similar migration patterns, and the variants HM9, HM10, HM21 and HM7 comprising the S343E mutation migrated to a more acidic region. This result suggests that a change in the isoelectric point of the protein occurs due to the introduction of glutamic acid by S344E substitution of the amino acid between G340 and I344.

In addition, based on the variant HM6, other amino acids in the C-terminal regions of alpha-helix 8 were substituted, thereby constructing the variants HM11 and HM12. The sequences of the substituted amino acids in the variants HM11 and HM12 are shown in Table 11 above. The variant HM11 was expressed in ExpiCHO cells, but the expression level thereof was lower than that of WT (FIG. 2), and the variant HM12 was not expressed in ExpiCHO cells. The variant HM11 exhibited an activity corresponding to 32% of that of WT (FIG. 6 in part B thereof).

Working Example 4. Construction of N-Terminal Amino Acid-Truncated PH20 Variants Based on HM6

The C-terminal region of PH20 is already well known to play an important role in the expression and enzymatic activity of PH20, but the role of the N-terminal region of PH20 is not well known. In order to examine the effect of truncation of the amino acid at the N-terminal region of PH20 on the enzymatic activity, variants HM40, HM13, HM41, HM24, HM42 and HM25 having the N-terminus truncated at N37, F38, R39, A40, P41 or P42 were constructed based on the variant HM6 (Table 11). Furthermore, HP61 and HP62 with modifications at the N-terminal amino acids were additionally constructed.

The variants HM40, HM13, HM41, HM24, HM42, HP61 and HP62 were expressed in ExpiCHO cells, but HM25 was not expressed (FIG. 7 in parts A and B thereof). The N-terminal truncated PH20 variants showed a difference in enzyme activity depending on the position where the N-terminus started. The variants HM40, HM13 and HM41, in which one to three amino acids were truncated, showed enzymatic activity similar to that of the template HM6, but HM24 and HM42, in which four to five amino acids were truncated, showed slightly lower activity than HM6 (FIG. 7 in part C thereof). However, HM25 in which six amino acids were truncated were little expressed in ExpiCHO cells, and the enzymatic activity was also significantly low (3.5 U/μg). It appears that changes in the enzymatic activities of HP61 and HP62 with modifications at N-terminal amino acids are not significant.

Regarding the enzymatic activities of the N-terminal truncated PH20 variants, measured by the substrate-gel assay (1 h of reaction), the enzymatic activities of HM40, HM13 and HM41 were similar to that of the template HM6, but the enzymatic activities of HM24 and HM42 were lower than that of HM6 (FIG. 7 in part D thereof). HM25 in which six amino acids were truncated could not be analyzed, because the amount of the protein produced was small.

When the physical properties of the variants HM40, HM13, HM41, HM24 and HM42 were analyzed using a phenyl column chromatography, these variants were eluted from the column earlier than WT, suggesting that these variants have a hydrophilic nature (FIG. 7 in part E thereof). This result suggests that the variants HM40, HM13, HM41, HM24 and HM42 constructed based on the variant HM6 maintained the hydrophilic nature of HM6 when considering the characteristics of L36 to A40 residues.

The aggregation temperatures of the N-terminal truncated PH20 variants, measured by DLS, were different among the variants depending on the position where the amino acid started (FIG. 7 in part F thereof). Although the N-terminal amino acid residues of the variants HM40, HM13, HM41 and HM42 were truncated, they showed an aggregation temperature of 50° C. or higher, indicating that the characteristics of the template HM6 were remained intact. Among these variants, the variants HM40 and HM42 exhibited an aggregation temperature which was 3 to 4° C. higher than that of HM6, indicating that the thermal stability of these variants increased. In addition, in order to examine the effect of substitution of the N-terminal amino acids of PH20 on protein expression and enzymatic activity, the following variants were constructed: the variant HM17 in which N-terminal amino acid sequences 36 to 47 (LNFRAPPVIPNV) SEQ ID NO: 118) of PH20 were substituted with FRGPLLPNR (SEQ ID NO: 116); and the variant HM18 in which N-terminal amino acid sequences 36 to 52 (LNFRAPPVIPNVPFLWA) (SEQ ID NO: 119) of PH20 were substituted with FRGPLLPNRPFTTV (SEQ ID NO: 117). The sequences of the substituted amino acids in the variants HM17 and HM18 are shown in Table 11 above. The variants HM17 and HM18 were not expressed in ExpiCHO cells. This suggests that, even when up to five amino acids located at the N-terminus were truncated, the variants showed protein expression and enzymatic activity; however, substitution of more amino acid sequences, such as 36 to 47 sequences or 36 to 52 sequences, had an effect on protein refolding.

Working Example 5. Construction of the C-Terminal Amino Acid-Truncated HM6-Based Variants HM14, HM15 and HM16 of PH20

The C-terminal region of PH20 is known to play an important role in protein expression and enzymatic activity. In the present invention, the variants HM14, HM15 and HM16, in which the C-terminal amino acids were truncated at I465, F468 and K471, respectively, were constructed based on the variant HM6. The sequences of the substituted amino acids in these variants HM14, HM15 and HM16 are shown in Table 11 above. These variants HM14, HM15 and HM16 were expressed in ExpiCHO cells (FIG. 8 in part A thereof), and the protein expression levels thereof were in the order of HM16>HM15>HM14, indicating that the protein expression levels decreased as the number of C-terminal amino acids truncated increased (FIG. 8 in part A thereof). However, the enzymatic activities of the variants HM14, HM15 and HM16 were in the order of HM16>HM14 (..WT)>HM15 (FIG. 8 in part B thereof). According to Frost et al., the C-terminal 477-483 region of PH20 is necessary for soluble expression, and when the C-terminus is truncated at C467, the enzymatic activity of the variant is only 10% of a PH20 variant whose C-terminus was truncated at 477 to 483, and when the C-terminus is truncated before 467, the variant has no enzymatic activity. However, the C-terminal truncated variants HM14, HM15 and HM16 constructed based on the variant HM6 in the present invention showed increased protein refolding due to amino acid substitution of the M345 to I361 region, and thus the thermal stability thereof increased. For this reason, even when the C-terminus was truncated after I465, F468 or P471, the variant showed enzymatic activity similar to that of WT, and the enzymatic activity thereof did not significantly decrease.

The structural flexibilities of WT and the variants HM14, HM15 and HM16 were examined by fluorescence quenching using acrylamide (FIG. 11 in part B thereof). The variants HM14, HM15 and HM16 were all structurally more flexible than WT. This result suggests that the C-terminal truncated variants constructed using the variant HM6 also maintained their structural flexibility.

The enzymatic activities of the variants HM14, HM15 and HM16, measured by turbidimetric assay, were also confirmed in substrate-gel assay (FIG. 8 in part C thereof).

When the physical properties of the C-terminal truncated variants were analyzed using a phenyl column chromatography, the variants HM14, HM15 and HM16 were all eluted earlier than WT, indicating that they had a hydrophilic nature. In addition, the hydrophilicities of these variants were in the order of HM16>HM14>HM15 (FIG. 8 in part D thereof).

Working Example 6. Construction of the HM10-Based Variants HM19 and HM20 Comprising N-Terminal and C-Terminal Amino Acid Truncation The PH20 variants constructed in the present invention were based on HM6, and HM8, HM9 and HM10, in which amino acid residues G340 to I344 were additionally substituted, exhibited better performance than WT in terms of protein expression levels, enzymatic activities and thermal stabilities. The variants HM19 and HM20 were constructed which had an N-terminus truncated at F38 and a C-terminus truncated at K470 or F468 based on HM10 having high enzymatic activity and thermal stability among variants HM8, HM9 and HM10. HM19 and HM20 were all expressed in ExpiCHO cells and purified using a HisTrap column chromatography (FIG. 9 in part A thereof). When the enzymatic activities of these variants were measured by turbidimetric assay, HM19 and HM20 exhibited an enzymatic activity which was 10% higher than that of WT (FIG. 9 in part B thereof). In substrate-gel assay, HM19 and HM20 also exhibited higher enzymatic activity than WT (FIG. 9 in part C thereof).

Working Example 7. Characterization of HM10-Based PH20 Variants

The expression levels of HM10-based C-terminal truncated variants in ExpiCHO cells showed a tendency to decrease as the length of the C-terminal region became shorter, and these variants were not expressed when the C-terminus was truncated at C464 or shorter (FIG. 12). C464 is necessary because it forms a disulfide bond with C437 and is important for maintaining the protein structure.

In order to examine whether the variant is not expressed in ExpiCHO cells when the C-terminus is truncated at 464 or shorter, Western blot analysis was performed. As shown in FIG. 13, the HM30, HM31, HM32 and HM33 variants were not detected in Western blots.

The enzymatic activities of the HM10-based C-terminal truncated variants, measured by turbidimetric assay, are shown in FIG. 14 in part A thereof and 14 in part B thereof. The C-terminal truncated PH20 variants exhibited an enzymatic activity of ±20% compared to WT. When the C-terminus was truncated after 1480 or beyond, the enzyme activity increased overall. In addition, the variants HP19 and HP20, obtained by removing the 6×His-tag from HM19 and HM20, showed decreases in enzymatic activity of 23% and 9.6%, respectively, compared to when the 6×His-tag was present. This suggests that the 6His-tag has an effect on the enzymatic activity.

When the enzymatic activities of the HM10-based C-terminal truncated variants were measured by substrate-gel assay, these variants exhibited higher enzymatic activity than WT and showed enzymatic activity similar to that of the template HM10, indicating that the difference in enzymatic activity depending on the length of the C-terminal region was not significant (FIG. 14 in part C thereof).

Working Example 8. Characterization of HM21-Based PH20 Variants

The variant HP34 was purified by four-step column chromatography (FIG. 15 in part A thereof), and the variant HP46 was purified by three-step column chromatography (FIG. 15 in part B thereof). The amounts of HP34 and HP46 produced were 1.73 mg/L and 25.6 mg/L, respectively. HP34 and HP46 are 6×His-tag-free variants, and the process of purifying these variants differs from the process of purifying variants having the 6×His-tag, and thus it is difficult to compare the expression levels of the proteins.

In turbidimetric assay, the activities of HP34 and HP46 were 45.6 U/μg and 47.2 U/μg, respectively, which were about 2-fold higher than that of WT and were about 10% higher than that of the template HM21 (FIG. 16 in part A thereof).

The kinetics of each variant was measured by Morgan-Elson assay, and the results of the measurement are shown in FIG. 16 in part B thereof. The catalytic efficiencies ($k_{cat}/K_m$) of HP34 and HP46 were 1.7 to 2 times higher than that of wild-type HW2. This result is consistent with the result that the specific activity was higher than that of WT. The Michaelis constant ($K_m$) was lower in these variants than in HW2, indicating the substrate affinities of these variants increased. From these results, it can be concluded that the HM21, HP34 and HP46 variants bind strongly to the substrate and have the property of converting the substrate into a product with high efficiency. This property is attributable to the effect of substitution of T341 with serine. It can be predicted that substituting threonine located at position 341 with an amino acid, such as alanine, glycine, aspartic acid or the like, would influence the enzymatic activity.

The aggregation temperatures of HP34 and HP46, measured by DLS, were 51.5° C. and 51.0° C., respectively, which were similar to that of the template HM21 and were about 5° C. higher than that of HW2, indicating that these variants were thermally stable (FIG. 17 in part A thereof). The enzymatic activity of HP34, measured by substrate-gel assay, was similar to that of HP20, whereas HP46 exhibited higher enzymatic activity than HP20, indicating that the protein refolding of HM21 as a template was better than that of HM10 (FIG. 17 in part B thereof).

Wild-type HW2 and the variant HP46 were left to stand overnight at pH 7.0 and pH 3.0, and then the enzymatic activities thereof were compared by substrate-gel assay. As a result, it was shown that HP46 exhibited high activity not only at pH 7.0 but also at pH 3.0, indicating that it had excellent stability (FIG. 17 in part C thereof).

HM53, HM54, HM55, HM56, HP59 and HP60 are variants having a mutation at the amino acid at position 341, among HM21-based variants. It was confirmed that the mutation of the amino acid at position 341 had various effects on the expression level and activity of the variants (FIG. 17 in parts D and E).

Working Example 9. In Vitro Immunogenicity Assay of PH20 Variant

Biopharmaceuticals with higher molecular weights than those of low-molecular-weight synthetic chemicals have a risk of triggering unintended immune responses when they enter the human body. An outside contact surface, created by refolding or interaction with adjacent domains in the secondary structure or tertiary structure of a large-molecular-weight biomaterial, can promote immune response to the biomaterial by providing an epitope to the immune system in the human body. This immune response can produce an anti-drug antibody (ADA), and this response can inhibit the drug's effectiveness, or cause hypersensitivity to the drug, or promote clearance of the drug in the human body. The immune response to the drug may therefore affect the results in clinical trials, and may cause serious abnormal reactions upon long-term use. This immune response can be influenced by various factors, and triggered by the specific response to the drug itself or disease, or by factors that depend on the method of drug administration or individual patients. Factors caused by the drug itself include the similarity or dissimilarity of the biopharmaceuticals to human peptides, posttranslational modification, impurities, aggregate formation, and the characteristics of the formulation. Factors that varies among individual patients include sex, reactivity with other drugs being taken, and genetic factors depending on the type of human leukocyte antigen (HLA).

This immunogenic response is triggered by CD4+ T cells or CD8+ T cells that recognize epitopes regardless of the cause of the immune response. Because of HLA class II gene diversity in individuals, epitopes of CD4+ T cells are different among individuals, and therefore the responsiveness to biopharmaceuticals in CD4+ T cells in each blood provided by the healthy donor can be a very important criterion for evaluating immune responses that may arise in clinical processes. CD4+ T cells are activated by antigen presenting cells (APCs) recognizing the antigens presented through their type II MHC (major histocompatibility complex). Activated CD4+ T cells release cytokines that activate macrophages, cytotoxic T cells, and B cells, resulting in high levels of antibody production. On the contrary, CD8+ T cells have direct cytotoxicity and directly remove cells infected with antigens, damaged cells, or cells that lost their function. CD8+ T cells have T cell receptors that can recognize specific antigen peptides bound to type I MHC molecules located on the surface of every cell. CD8+ T cells can also be activated by recognizing antigens presented by antigen presenting cells, and this activation can be further enhanced by cytokines of CD4+ T cells. Therefore, when the activation level of CD4+ T cells and CD8+ T cells by new biomaterials is measured in vitro, it is possible to predict immunogenic responses that can be induced in clinical processes. In this working example, in order to predict the immunogenicity of the PH20 variant in comparison with a control, CD4+ T cells and CD8+ T cells were isolated from PBMCs, and then treated with 1.5 ng/mL and 15 ng/mL of the control PH20 and the PH20 variant (HP46), and then the distributions of activated CD4+ T cells and CD8+ T cells were measured. The activation level of each type of T cells was measured using Stimulating Index, and Stimulating Index (SI) is defined as follows. If the SI value of cells is 2 or more, it can be determined that the cells were activated at the significant level.

Stimulating Index (SI)=(T-cell activation level after treatment with test sample)/(T-cell activation level after treatment with vehicle)

Immunogenic responses may vary depending on the HLA type. Therefore, experiments for measuring responses in more various HLA types were performed using T cells isolated from PBMCs provided from 10 healthy donors. The HLA types of the 10 PBMCs used are shown in Table 12 below.

TABLE 12

| | HLA types of tested PBMCs | | | | | | | | | | | |
|---|---|---|---|---|---|---|---|---|---|---|---|---|
| No. | HLA A | | HLA B | | HLA C1 | | DRB1 | | DQB1 | | DPB1 | |
| 1 | 0206 | 3303 | 3501 | 5801 | 0302 | 0801 | 1405 | 1501 | 0303 | 0602 | 0201 | 0301 |
| 2 | 0201 | 0207 | 4601 | 5101 | 0102 | 1502 | 0803 | 1101 | 0301 | 0601 | 0201 | 0202 |
| 3 | 0206 | 3101 | 1501 | 3501 | 0304 | 0401 | 0803 | 0901 | 0303 | 0601 | 0201 | 0501 |
| 4 | 0101 | 3101 | 1501 | 1517 | 0303 | 0701 | 1302 | 1501 | 0602 | 0604 | 0401 | 0501 |
| 5 | 0201 | 3101 | 5101 | 6701 | 0702 | 1402 | 0401 | 0403 | 0301 | 0302 | 0201 | 0401 |
| 6 | 0201 | 1101 | 1501 | 3901 | 0401 | 0702 | 0102 | 0901 | 0402 | 0501 | 0101 | 1401 |
| 7 | 0201 | 0206 | 4002 | 5502 | 0102 | 0304 | 0802 | 1454 | 0302 | 0502 | 0402 | 0501 |
| 8 | 0201 | 0201 | 1501 | 4001 | 0303 | 0304 | 0802 | 1406 | 0301 | 0302 | 0501 | 1301 |
| 9 | 1101 | 2402 | 4006 | 5101 | 0801 | 1502 | 0701 | 0901 | 0202 | 0303 | 0201 | 1301 |
| 10 | 2602 | 3101 | 4002 | 5101 | 0304 | 1502 | 0405 | 1501 | 0401 | 0602 | 0201 | 0501 |

The results of measuring the activation levels of CD4+ and CD8+ T cells treated with each of PH20 and the PH20 variant are summarized in Table 13 below. When looking at the results of measuring the activation levels of CD4+ and CD8+ T cells, it appears that PH20 and the PH20 variant all show relatively low activation levels. In the case of PH20, the activation level of CD4+ T cells was measured to be 2 or more in two experiments, and in the case of the PH20 variant, the activation of CD4+ T cells was not detected. In the case of PH20, the activation of CD8+ T cells was detected in one experiment, and in the case of the PH20 variant, the activation of CD8+ T cells was also detected in one experiment. However, in the case of PH20, the SI value was measured to be 2 or more at both 1.5 ng/mL and 15 ng/mL, but in the case of the PH20 variant, an SI value of 2 or less at 1.5 ng/mL and an SI value of 2 or more at 15 ng/mL were measured (see FIGS. 18 and 19).

Therefore, at the lower concentration, the activation level of CD8+ T cells was observed to be low in the case of the PH20 variant, and it is determined that the activation level of CD8+ T cells by PH20 is higher than the activation level of CD8+ T cells by the PH20 variant. The conclusions drawn from the above results are as follows:

1) the activation levels of CD4+ T cells and CD8+ T cells by PH20 and the PH20 variant are relatively low; and
2) the possibility of activation of CD4+ T cells and CD8+ T cells by the PH20 variant is lower than that by PH20.

From these results, it is expected that the PH20 variant will have a lower possibility of triggering an immunogenic response in clinical processes than PH20.

TABLE 13

| Stimulating Index (SI) measured from in vitro immunogenicity assay results | | | | | | | |
|---|---|---|---|---|---|---|---|
| | CD4 | | | | CD8 | | | |
| PBMC | PH20 (ng/mL) | | PH20 variant (ng/mL) | | PH20 (ng/mL) | | PH20 variant (ng/mL) | |
| No. | 1.5 | 15 | 1.5 | 15 | 1.5 | 15 | 1.5 | 15 |
| 1 | 1.03 | 0.859 | 0.728 | 1.176 | 1.38 | 1.42 | 1.22 | 1.60 |
| 2 | 1.05 | 0.09 | 0.596 | 0.922 | 1.20 | 1.11 | 1.00 | 1.07 |

TABLE 13-continued

Stimulating Index (SI) measured from in vitro immunogenicity assay results

| PBMC No. | CD4 | | | | CD8 | | | |
|---|---|---|---|---|---|---|---|---|
| | PH20 (ng/mL) | | PH20 variant (ng/mL) | | PH20 (ng/mL) | | PH20 variant (ng/mL) | |
| | 1.5 | 15 | 1.5 | 15 | 1.5 | 15 | 1.5 | 15 |
| 3 | 1.90 | 1.44 | 1.56 | 1.12 | 1.43 | 1.31 | 1.59 | 1.35 |
| 4 | 2.51 | 2.79 | 0.788 | 1.82 | 1.28 | 1.90 | 0.579 | 0.974 |
| 5 | 1.27 | 1.47 | 1.09 | 1.14 | 0.987 | 0.932 | 0.972 | 1.02 |
| 6 | 0.825 | 0.834 | 0.998 | 0.946 | 0.904 | 1.13 | 1.09 | 0.986 |
| 7 | 2.07 | 2.07 | 1.43 | 1.90 | 2.08 | 2.34 | 1.30 | 2.46 |
| 8 | 0.898 | 1.079 | 0.967 | 0.822 | 0.926 | 1.06 | 0.896 | 0.813 |
| 9 | 0.882 | 0.957 | 0.895 | 0.941 | 0.853 | 0.993 | 0.950 | 1.09 |
| 10 | 0.983 | 0.970 | 1.12 | 1.13 | 1.15 | 1.08 | 1.15 | 1.24 |

Industrial Applicability

The PH20 variants or fragments thereof according to the present invention have increased protein expression levels and show an increase in protein aggregation temperature of 4-11.5° C. or so when expressed in CHO (ExpiCHO) cells so that they can be efficiently produced while having high thermal stability, compared to the mature wild-type PH20.

Further, as the result of substrate-gel assay, one of tests to measure the activity of hyaluronidase, the PH20 variants or fragments thereof according to the present invention have improved protein refolding so that they are renatured faster than that of the mature wild-type PH20, and the original enzymatic activity is maintained regardless of the C-terminal truncation position.

Furthermore, the PH20 variants or fragments thereof according to the present invention have low immunogenicity so that they can be repeatedly administered to the human body.

REFERENCES

Arming, S., Strobl, B., Wechselberger, C., and Kreil, G. (1997). In vitro mutagenesis of PH-20 hyaluronidase from human sperm. Eur J Biochem 247, 810-814.

Bookbinder, L. H., Hofer, A., Haller, M. F., Zepeda, M. L., Keller, G. A., Lim, J. E., Edgington, T. S., Shepard, H. M., Patton, J. S., and Frost, G. I. (2006). A recombinant human enzyme for enhanced interstitial transport of therapeutics. J Control Release 114, 230-241.

Chao, K. L., Muthukumar, L., and Herzberg, O. (2007). Structure of human hyaluronidase-1, a hyaluronan hydrolyzing enzyme involved in tumor growth and angiogenesis. Biochemistry 46, 6911-6920.

Frost, G. I. (2007). Recombinant human hyaluronidase (rHuPH20): an enabling platform for subcutaneous drug and fluid administration. Expert Opin Drug Deliv 4, 427-440.

The invention claimed is:

1. A PH20 variant, wherein the amino acid sequence of the PH20 variant is SEQ ID NO: 1 with modifications consisting of:
   (a) amino acid residue substitutions M345T, S347T, M348K, K349E, L352Q, L353A, L354I, D355K, N356E, E359D and I361T relative to SEQ ID NO: 1, and one or more amino acid residue substitutions selected from the group consisting of T341A, T341G, T341S, L342W, S343E, I344N and N363G relative to SEQ ID NO: 1;
   (b) an N-terminus deletion of amino acid residues M1 to T35, M1 to L36, M1 to N37, M1 to F38, M1 to R39, or M1 to A40 of SEQ ID NO: 1; and
   (c) a C-terminus deletion, wherein the C-terminus of the PH20 variant ends with an amino acid residue selected from any one of I465 to S490 of SEQ ID NO: 1.

2. The PH20 variant of claim 1, wherein the amino acid residue substitutions relative to SEQ ID NO: 1 consist of the amino acid residue substitutions in any one of the following groups of amino acid residue substitutions:
   (a) T341S, L342W, S343E, I344N, M345T, S347T, M348K, K349E, L352Q, L353A, L354I, D355K, N356E, E359D and I361T;
   (b) L342W, S343E, I344N, M345T, S347T, M348K, K349E, L352Q, L353A, L354I, D355K, N356E, E359D and I361T;
   (c) M345T, S347T, M348K, K349E, L352Q, L353A, L354I, D355K, N356E, E359D, I361T and N363G;
   (d) T341G, L342W, S343E, I344N, M345T, S347T, M348K, K349E, L352Q, L353A, L354I, D355K, N356E, E359D and I361T;
   (e) T341A, L342W, S343E, I344N, M345T, S347T, M348K, K349E, L352Q, L353A, L354I, D355K, N356E, E359D and I361T;
   (f) I344N, M345T, S347T, M348K, K349E, L352Q, L353A, L354I, D355K, N356E, E359D and I361T; and
   (g) S343E, I344N, M345T, S347T, M348K, K349E, L352Q, L353A, L354I, D355K, N356E, E359D and I361T.

3. The PH20 variant of claim 1, wherein the C-terminus of the PH20 variant ends with amino acid residue I465, D466, A467, F468, K470, P471, P472, M473, E474, T475, E476, P478, I480, Y482, A484, P486, T488, or S490 of SEQ ID NO: 1.

4. A PH20 variant comprising the amino acid sequence of any one of the amino acid sequences of SEQ ID NOs: 60, 63 to 69, 71 to 74, 77 to 80, 82, and 87 to 115.

5. A PH20 variant comprising the amino acid sequence of SEQ ID NO: 99.

6. The PH20 variant of claim 4, wherein the amino acid sequence of the PH20 variant consists of any one of the amino acid sequences of SEQ ID NOs: 60, 63 to 69, 71 to 74, 77 to 80, 82, and 87 to 115.

7. A PH20 variant, wherein the amino acid sequence of the PH20 variant consists of the amino acid sequence of SEQ ID NO:99.

8. A PH20 variant, wherein the amino acid sequence of the PH20 variant is SEQ ID NO: 1 with modifications consisting of:
   (a) amino acid residue substitutions consisting of T341S, L342W, S343E, I344N, M345T, S347T, M348K, K349E, L352Q, L353A, L354I, D355K, N356E, E359D, and I361T relative to SEQ ID NO: 1;
   (b) an N-terminus deletion of amino acid residues M1 to T35, M1 to L36, M1 to N37, M1 to F38, M1 to R39, or M1 to A40; and
   (c) a C-terminus deletion, wherein the C-terminus of the PH20 variant ends with an amino acid residue selected from any one of I465 to S490 of SEQ ID NO: 1.

9. The PH20 variant of claim 8, wherein the N-terminus deletion is a deletion of amino acid residues M1 to T35, M1 to L36, M1 to N37, or M1 to F38 of SEQ ID NO: 1.

10. The PH20 variant of claim 8, wherein the N-terminus deletion is a deletion of amino acid residues M1 to T35, M1 to L36, M1 to N37, or M1 to F38 of SEQ ID NO: 1, and the C-terminus of the PH20 variant ends with amino acid residue I465, D466, A467, F468, K470, P471, P472, M473, E474, T475, E476, P478, I480, Y482, A484, P486, T488, or S490 of SEQ ID NO: 1.

11. The PH20 variant of claim 8, wherein the N-terminus deletion is a deletion of amino acid residues M1 to T35, M1 to L36, M1 to N37, or M1 to F38 of SEQ ID NO: 1, and the C-terminus of the PH20 variant ends with amino acid residue I465, F468, or P471 of SEQ ID NO: 1.

12. The PH20 variant of claim 8, wherein the N-terminus deletion is a deletion of amino acid residues M1 to T35, M1 to L36, M1 to N37, M1 to F38, or M1 to R39 of SEQ ID NO: 1, and the C-terminus of the PH20 variant ends with amino acid residue F468 of SEQ ID NO: 1.

13. The PH20 variant of claim 12, wherein the N-terminus deletion is a deletion of amino acid residues M1 to T35, M1 to L36, M1 to N37, or M1 to F38 of SEQ ID NO: 1.

14. A PH20 variant, wherein the amino acid sequence of the PH20 variant is SEQ ID NO: 1 with modifications consisting of:

(a) amino acid residue substitutions, wherein the amino acid residue substitutions consist of amino acid residue substitutions in the region T341 to I361 of SEQ ID NO: 1, wherein the amino acid residue substitutions in the region T341 to I361 comprise amino acid residue substitutions M345T, S347T, M348K, K349E, L352Q, L353A, L354I, D355K, N356E, E359D, and I361T relative to SEQ ID NO: 1, and one or more amino acid residue substitutions selected from the group consisting of T341A, T341C, T341D, T341G, T341S, L342W, and S343E relative to SEQ ID NO: 1, and wherein the amino acid residue substitutions in the region do not comprise an amino acid residue substitution at amino acid residue C351 or Y357 relative to SEQ ID NO: 1;
(b) an N-terminus deletion of amino acid residues M1 to T35, M1 to L36, M1 to N37, M1 to F38, M1 to R39, or M1 to A40 of SEQ ID NO: 1; and
(c) a C-terminus deletion, wherein the C-terminus of the PH20 variant ends with an amino acid residue selected from any one of I465 to S490 of SEQ ID NO: 1.

15. The PH20 variant of claim 14, wherein the one or more amino acid residue substitutions is selected from the group consisting of T341A, T341G, T341S, L342W, and S343E relative to SEQ ID NO: 1.

16. The PH20 variant of claim 14, wherein the amino acid residue substitutions in the region consist of the amino acid residue substitutions in any one of the following groups of amino acid residue substitutions:
   (a) T341S, L342W, S343E, I344N, M345T, S347T, M348K, K349E, L352Q, L353A, L354I, D355K, N356E, E359D, and I361T;
   (b) L342W, S343E, I344N, M345T, S347T, M348K, K349E, L352Q, L353A, L354I, D355K, N356E, E359D, and I361T;
   (c) T341D, L342W, S343E, I344N, M345T, S347T, M348K, K349E, L352Q, L353A, L354I, D355K, N356E, E359D, and I361T;
   (d) T341G, L342W, S343E, I344N, M345T, S347T, M348K, K349E, L352Q, L353A, L354I, D355K, N356E, E359D, and I361T;
   (e) T341A, L342W, S343E, I344N, M345T, S347T, M348K, K349E, L352Q, L353A, L354I, D355K, N356E, E359D, and I361T;
   (f) T341C, L342W, S343E, I344N, M345T, S347T, M348K, K349E, L352Q, L353A, L354I, D355K, N356E, E359D, and I361T; and
   (g) S343E, I344N, M345T, S347T, M348K, K349E, L352Q, L353A, L354I, D355K, N356E, E359D, and I361T.

17. The PH20 variant of claim 1, wherein the C-terminus of the PH20 variant ends with an amino acid residue selected from any one of D466 to S490 of SEQ ID NO: 1.

18. The PH20 variant of claim 1, wherein the one or more amino acid residue substitutions is selected from the group consisting of T341S, L342W, S343E, I344N, and N363G relative to SEQ ID NO: 1.

19. A PH20 variant comprising the amino acid sequence of SEQ ID NO: 60, 63, 64, 65, 66, 67, 68, 69, 71, 72, 73, 74, 77, 78, 79, 80, 82, 87, 88, 89, 90, 91, 92, 93, 94, 95, 97, 98, 99, 100, 101, 102, 103, 104, 105, 106, 107, 112, 113, 114, or 115.

20. The PH20 variant of claim 19, wherein the amino acid sequence of the PH20 variant consists of the amino acid sequence of SEQ ID NO: 60, 63, 64, 65, 66, 67, 68, 69, 71, 72, 73, 74, 77, 78, 79, 80, 82, 87, 88, 89, 90, 91, 92, 93, 94, 95, 97, 98, 99, 100, 101, 102, 103, 104, 105, 106, 107, 112, 113, 114, or 115.

21. The PH20 variant of claim 1, wherein the C-terminus of the PH20 variant ends with amino acid residue I465, D466, A467, F468, K470, P471, P472, M473, E474, T475, E476, P478, I480, or Y482 of SEQ ID NO: 1.

22. The PH20 variant of claim 1, wherein the N-terminus deletion is a deletion of amino acid residues M1 to T35, M1 to L36, M1 to N37, or M1 to F38 of SEQ ID NO: 1, and wherein the C-terminus of the PH20 variant ends with amino acid residue I465, D466, A467, F468, K470, P471, P472, M473, E474, T475, E476, P478, I480, or Y482 of SEQ ID NO: 1.

23. The PH20 variant of claim 8, wherein the N-terminus deletion is a deletion of amino acid residues M1 to T35, M1 to L36, M1 to N37, or M1 to F38 of SEQ ID NO: 1, and wherein the C-terminus of the PH20 variant ends with amino acid residue I465, D466, A467, F468, K470, P471, P472, M473, E474, T475, E476, P478, I480, or Y482 of SEQ ID NO: 1.

24. The PH20 variant of claim 8, wherein the N-terminus deletion is a deletion of amino acid residues M1 to T35, M1 to L36, M1 to N37, M1 to F38, or M1 to R39 of SEQ ID NO: 1.

25. The PH20 variant of claim 8, wherein the C-terminus of the PH20 variant ends with amino acid residue F468 of SEQ ID NO: 1.

26. The PH20 variant of claim 2, wherein the C-terminus of the PH20 variant ends with amino acid residue F468 of SEQ ID NO: 1.

27. The PH20 variant of claim 8, wherein the C-terminus of the PH20 variant ends with amino acid residue Y482 of SEQ ID NO: 1.

28. The PH20 variant of claim 24, wherein the C-terminus of the PH20 variant ends with amino acid residue Y482 of SEQ ID NO: 1.

29. The PH20 variant of claim 8, wherein the C-terminus of the PH20 variant ends with amino acid residue I465, D466, A467, F468, K470, or P471 of SEQ ID NO: 1.

30. The PH20 variant of claim 24, wherein the C-terminus of the PH20 variant ends with amino acid residue I465, D466, A467, F468, K470, or P471 of SEQ ID NO: 1.

31. A PH20 variant, wherein the amino acid sequence of the PH20 variant is SEQ ID NO: 1 with modifications consisting of:
   (a) amino acid residue substitutions consisting essentially of amino acid residue substitutions in the region T341 to I361 of SEQ ID NO: 1, wherein the amino acid residue substitutions in the region T341 to I361 comprise amino acid residue substitutions M345T, S347T, M348K, K349E, L352Q, L353A, L354I, D355K, N356E, E359D, and I361T relative to SEQ ID NO: 1, and one or more amino acid residue substitutions selected from the group consisting of T341A, T341C, T341D, T341G, T341S, L342W, and S343E relative to SEQ ID NO: 1, and wherein the amino acid residue substitutions in the region do not comprise an amino acid residue substitution at amino acid residue C351 or Y357 relative to SEQ ID NO: 1;
   (b) an N-terminus deletion of amino acid residues M1 to T35, M1 to L36, M1 to N37, M1 to F38, M1 to R39, or M1 to A40 of SEQ ID NO: 1; and
   (c) a C-terminus deletion, wherein the C-terminus of the PH20 variant ends with an amino acid residue selected from any one of 1465 to S490 of SEQ ID NO: 1.

32. The PH20 variant of claim 31, wherein the one or more amino acid residue substitutions is selected from the group consisting of T341A, T341G, T341S, L342W, and S343E relative to SEQ ID NO: 1.

33. The PH20 variant of claim 31, wherein the amino acid residue substitutions in the region consist of the amino acid residue substitutions in any one of the following groups of amino acid residue substitutions:
  (a) T341S, L342W, S343E, I344N, M345T, S347T, M348K, K349E, L352Q, L353A, L354I, D355K, N356E, E359D, and I361T;
  (b) L342W, S343E, I344N, M345T, S347T, M348K, K349E, L352Q, L353A, L354I, D355K, N356E, E359D, and I361T;
  (c) T341D, L342W, S343E, I344N, M345T, S347T, M348K, K349E, L352Q, L353A, L354I, D355K, N356E, E359D, and I361T;
  (d) T341G, L342W, S343E, I344N, M345T, S347T, M348K, K349E, L352Q, L353A, L354I, D355K, N356E, E359D, and I361T;
  (e) T341A, L342W, S343E, I344N, M345T, S347T, M348K, K349E, L352Q, L353A, L354I, D355K, N356E, E359D, and I361T;
  (f) T341C, L342W, S343E, I344N, M345T, S347T, M348K, K349E, L352Q, L353A, L354I, D355K, N356E, E359D, and I361T; and
  (g) S343E, I344N, M345T, S347T, M348K, K349E, L352Q, L353A, L354I, D355K, N356E, E359D, and I361T.

34. The PH20 variant of claim 31, wherein the amino acid residue substitutions in the region consist of T341S, L342W, S343E, I344N, M345T, S347T, M348K, K349E, L352Q, L353A, L354I, D355K, N356E, E359D, and I361T relative to SEQ ID NO: 1.

35. The PH20 variant of claim 31, wherein the amino acid residue substitutions in the region consist of T341S, L342W, S343E, I344N, M345T, S347T, M348K, K349E, L352Q, L353A, L354I, D355K, N356E, E359D, and I361T relative to SEQ ID NO: 1, and the N-terminus deletion is a deletion of amino acid residues M1 to T35, M1 to L36, M1 to N37, or M1 to F38 of SEQ ID NO: 1.

36. A PH20 variant, wherein the amino acid sequence of the PH20 variant is SEQ ID NO: 1 with modifications consisting of:
  (a) amino acid residue substitutions relative to SEQ ID NO: 1, wherein the amino acid residue substitutions consist essentially of:
    amino acid residue substitutions M345T, S347T, M348K, K349E, L352Q, L353A, L354I, D355K, N356E, E359D and I361T relative to SEQ ID NO: 1, and
    one or more amino acid residue substitutions selected from the group consisting of T341A, T341G, T341S, L342W, S343E, I344N and N363G relative to SEQ ID NO: 1;
  (b) an N-terminus deletion of amino acid residues M1 to T35, M1 to L36, M1 to N37, M1 to F38, M1 to R39, or M1 to A40 of SEQ ID NO: 1; and
  (c) a C-terminus deletion, wherein the C-terminus of the PH20 variant ends with an amino acid residue selected from any one of I465 to S490 of SEQ ID NO: 1.

37. The PH20 variant of claim 36, wherein the C-terminus of the PH20 variant ends with amino acid residue I465, D466, A467, F468, K470, P471, P472, M473, E474, T475, E476, P478, I480, Y482, A484, P486, T488, or S490 of SEQ ID NO: 1.

38. The PH20 variant of claim 36, wherein the C-terminus of the PH20 variant ends with an amino acid residue selected from any one of D466 to S490 of SEQ ID NO: 1.

39. The PH20 variant of claim 36, wherein the one or more amino acid residue substitutions is selected from the group consisting of T341S, L342W, S343E, I344N, and N363G relative to SEQ ID NO: 1.

40. The PH20 variant of claim 36, wherein the C-terminus of the PH20 variant ends with amino acid residue I465, D466, A467, F468, K470, P471, P472, M473, E474, T475, E476, P478, I480, or Y482 of SEQ ID NO: 1.

41. The PH20 variant of claim 36, wherein the N-terminus deletion is a deletion of amino acid residues M1 to T35, M1 to L36, M1 to N37, or M1 to F38 of SEQ ID NO: 1, and wherein the C-terminus of the PH20 variant ends with amino acid residue I465, D466, A467, F468, K470, P471, P472, M473, E474, T475, E476, P478, I480, or Y482 of SEQ ID NO: 1.

42. A protein comprising the PH20 variant of claim 1.
43. A protein comprising the PH20 variant of claim 2.
44. A protein comprising the PH20 variant of claim 8.
45. A protein comprising the PH20 variant of claim 14.
46. A protein comprising the PH20 variant of claim 16.
47. A protein comprising the PH20 variant of claim 31.
48. A protein comprising the PH20 variant of claim 33.
49. A protein comprising the PH20 variant of claim 36.

\* \* \* \* \*

UNITED STATES PATENT AND TRADEMARK OFFICE
CERTIFICATE OF CORRECTION

| | |
|---|---|
| PATENT NO. | : 12,371,683 B2 |
| APPLICATION NO. | : 16/628258 |
| DATED | : July 29, 2025 |
| INVENTOR(S) | : Soon Jae Park et al. |

It is certified that error appears in the above-identified patent and that said Letters Patent is hereby corrected as shown below:

On the Title Page

(54) Title, and in the Specification Column 1, Line 3, delete "COMPRISING" and insert --CONTAINING--;

(57) Abstract, Lines 1-5, before "PH20", delete "The present invention is related to the field of protein engineering technology which increases the enzymatic activity and thermal stability of human hyaluronidase which is an enzyme that hydrolyzes hyaluronic acid; and more particularly to hyaluronidase";

(57) Abstract, Line 6, delete "thereof, which comprise" and insert --thereof comprising--;

(57) Abstract, Line 8, delete "and" and insert --and/or--;

(57) Abstract, Line 11, delete "cleaved" and insert --truncated--;

(57) Abstract, Line 11, delete the paragraph break after "additionally.";

(57) Abstract, Line 12, after "Specifically,", delete "the present invention relates to";

(57) Abstract, Line 13, delete "thereof, which" and insert --thereof--;

(57) Abstract, Line 18, after "comprise", delete "the";

(57) Abstract, Line 21, delete "one or more" and insert --portion(s) of--;

Page 4, (56) Other Publications, Line 31, delete "forRefusal" and insert --for Refusal--;

Signed and Sealed this
Sixteenth Day of December, 2025

John A. Squires
*Director of the United States Patent and Trademark Office*

CERTIFICATE OF CORRECTION (continued)
U.S. Pat. No. 12,371,683 B2

Page 5, (56) Other Publications, Line 49, delete "*coli*and" and insert --*coli* and--;

In the Specification

Column 1, Line 24, delete "Q303380 Sub SeqListing ST25.txt;" and insert --Q303380_Sub_SeqListing_ST25.txt;--;

Column 4, Line 25, after "template,", insert --(Chao et al., 2007),--;

Column 4, Line 33, delete "(n)" and insert --(η)--;

Column 4, Line 34, delete "1344" and insert --I344--;

Column 4, Line 36, delete "1344" and insert --I344--;

Column 4, Line 54, delete "1367L)" and insert --I367L)--;

Column 5, Line 17, Brief Description of the Drawings, delete "Hya11." and insert --Hyal1.--;

Column 5, Line 39, delete "5C" and insert --5 in part C thereof--;

Column 7, Line 47, delete "Part a" and insert --part A--;

Column 13, Lines 29-30, delete "an amino acid residue immediately after an", insert --amino acid residues starting with the amino acid residue which immediately follows the--;

Column 13, Lines 31-32, delete "is cleaved and deleted." and insert --are deleted by truncation.--;

Column 13, Line 33, delete "cleavage" and insert --"truncation--;

Column 14, Line 66, before "I465,", delete "at";

Column 19, Line 5, delete "for" and insert --by--;

Column 23, Table 10, for primer SPAM1-6H-Not, Line 2 of the sequence, delete "TGA TGA TGG AG AAA CCA ATT CTG C" and insert --TGA TGA TGG AAG AAA CCA ATT CTG C--;

Column 23, Table 10, for primer B4203-HM4-F, Line 3 of the sequence, delete "AG GAA TCA TGT CA" and insert --AAG GAA TCA TGT CA--;

Column 23, Table 10, for primer cB4203-HM8-M, Line 2 of the sequence, delete "AGA ACC AG GAA TC" and insert --AGA ACC AAG GAA TC--;

Column 23, Table 10, for primer cB4203-HM10-M, Line 2 of the sequence, delete "AGA ACC AG GAA TC" and insert --AGA ACC AAG GAA TC--;

Column 57, Line 45, after "FIG. 3 in part", delete "a" and insert --A--;

Column 57, Line 49, delete "ab 193009)" and insert --ab193009)--;

Column 59, Line 20, delete "1344" and insert --I344--;

Column 59, Line 55, delete "344N;" and insert --I344N;--;

Column 61, Line 40, delete "SEQ" and insert --(SEQ--;

Column 62, Line 7, delete "(..WT)" and insert --(≡WT)--;

Column 62, Line 16, delete "1361" and insert --I361--;

Column 62, Line 46, delete "1344" and insert --I344--;

Column 63, Line 16, delete "1480" and insert --I480--;

Column 63, Line 54, delete "($K_m$" and insert --($K_m$)--;

Column 67, Line 29, delete "renatured" and insert --re-natured--;

In the Claims

In Claim 2, Column 225, Line 55, delete "1361T;" and insert --I361T;--;

In Claim 3, Column 225, Line 63, delete "1480," and insert --I480,--;

In Claim 8, Column 226, Line 32, after "substitutions", delete "consisting of";

In Claim 14, Column 227, Line 5, delete "1361" and insert --I361--;

In Claim 16, Column 227, Line 37, delete "1361T;" and insert --I361T;--;

In Claim 21, Column 228, Line 4, delete "1480," and insert --I480,--;

In Claim 22, Column 228, Line 10, delete "1480," and insert --I480,--;

In Claim 23, Column 228, Line 17, delete "1480," and insert --I480,--;

CERTIFICATE OF CORRECTION (continued)
U.S. Pat. No. 12,371,683 B2

In Claim 31, Column 228, Line 46, delete "1361" and insert --I361--;

In Claim 31, Column 228, Line 47, delete "1361" and insert --I361--;

In Claim 31, Column 228, Line 63, delete "1465" and insert --I465--;

In Claim 36, Column 230, Line 13, delete "1465" and insert --I465--;

In Claim 37, Column 230, Line 17, delete "1480," and insert --I480,--;

In Claim 40, Column 230, Line 28, delete "1480," and insert --I480,--; and

In Claim 41, Column 230, Line 34, delete "1480," and insert --I480,--.

```
SEQUENCE LISTING

<160> NUMBER OF SEQ ID NOS: 115

<210> SEQ ID NO 1
<211> LENGTH: 509
<212> TYPE: PRT
<213> ORGANISM: Artificial Sequence
<220> FEATURE:
<223> OTHER INFORMATION: Synthetic Sequence

<400> SEQUENCE: 1

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
                20                  25                  30

Cys Leu Thr Leu Asn Phe Arg Ala Pro Pro Val Ile Pro Asn Val Pro
            35                  40                  45

Phe Leu Trp Ala Trp Asn Ala Pro Ser Glu Phe Cys Leu Gly Lys Phe
        50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110
```

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
            500                 505

<210> SEQ ID NO 2
<211> LENGTH: 435
<212> TYPE: PRT

<213> ORGANISM: Artificial Sequence
<220> FEATURE:
<223> OTHER INFORMATION: Synthetic Sequence

<400> SEQUENCE: 2

```
Met Ala Ala His Leu Leu Pro Ile Cys Ala Leu Phe Leu Thr Leu Leu
1               5                   10                  15

Asp Met Ala Gln Gly Phe Arg Gly Pro Leu Leu Pro Asn Arg Pro Phe
            20                  25                  30

Thr Thr Val Trp Asn Ala Asn Thr Gln Trp Cys Leu Glu Arg His Gly
        35                  40                  45

Val Asp Val Asp Val Ser Val Phe Asp Val Val Ala Asn Pro Gly Gln
    50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
            85                  90                  95

Pro Gln Asn Ala Ser Leu Ile Ala His Leu Ala Arg Thr Phe Gln Asp
            100                 105                 110

Ile Leu Ala Ala Ile Pro Ala Pro Asp Phe Ser Gly Leu Ala Val Ile
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
            165                 170                 175

Gly Ala Ala Arg Ala Trp Met Ala Gly Thr Leu Gln Leu Gly Arg Ala
            180                 185                 190

Leu Arg Pro Arg Gly Leu Trp Gly Phe Tyr Gly Phe Pro Asp Cys Tyr
        195                 200                 205

Asn Tyr Asp Phe Leu Ser Pro Asn Tyr Thr Gly Gln Cys Pro Ser Gly
    210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
            245                 250                 255

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
        275                 280                 285

Ile Phe Tyr Asp Thr Thr Asn His Phe Leu Pro Leu Asp Glu Leu Glu
    290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
            325                 330                 335

Lys Glu Tyr Met Asp Thr Thr Leu Gly Pro Phe Ile Leu Asn Val Thr
            340                 345                 350

Ser Gly Ala Leu Leu Cys Ser Gln Ala Leu Cys Ser Gly His Gly Arg
        355                 360                 365

Cys Val Arg Arg Thr Ser His Pro Lys Ala Leu Leu Leu Leu Asn Pro
    370                 375                 380

Ala Ser Phe Ser Ile Gln Leu Thr Pro Gly Gly Gly Pro Leu Ser Leu
```

```
                385                 390                 395                 400
Arg Gly Ala Leu Ser Leu Glu Asp Gln Ala Gln Met Ala Val Glu Phe
                    405                 410                 415

Lys Cys Arg Cys Tyr Pro Gly Trp Gln Ala Pro Trp Cys Glu Arg Lys
                420                 425                 430

Ser Met Trp
        435

<210> SEQ ID NO 3
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 3

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 4
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 4

Met Lys Trp Val Thr Phe Ile Ser Leu Leu Phe Leu Phe Ser Ser Ala
1               5                   10                  15

Tyr Ser

<210> SEQ ID NO 5
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 5

Met Ala Ala His Leu Leu Pro Ile Cys Ala Leu Phe Leu Thr Leu Leu
1               5                   10                  15

Asp Met Ala Gln Gly
            20

<210> SEQ ID NO 6
<211> LENGTH: 33
<212> TYPE: DNA
<213> ORGANISM: Artificial Sequence
<220> FEATURE:
<223> OTHER INFORMATION: Synthetic Sequence

<400> SEQUENCE: 6
gaatatctcg aggccaccat gaagtgggtt aca                          33

<210> SEQ ID NO 7
<211> LENGTH: 55
<212> TYPE: DNA
<213> ORGANISM: Artificial Sequence
<220> FEATURE:
<223> OTHER INFORMATION: Synthetic Sequence

<400> SEQUENCE: 7
```
ctaattgcgg ccgctcatta gtggtgatgg tgatgatgga agaaaccaat tctgc        55

<210> SEQ ID NO 8
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 8
taacaggagg tgctctgaaa ttcagagagt aagcagagga g                       41

<210> SEQ ID NO 9
<211> LENGTH: 98
<212> TYPE: DNA
<213> ORGANISM: Artificial Sequence
<220> FEATURE:
<223> OTHER INFORMATION: Synthetic Sequence

<400> SEQUENCE: 9
atggggaacc ctcagtataa caagaaccaa ggaatcatgt caggccatca aggagtatat   60
ggacactaca ctggggccct acataatcaa cgtcacac                           98

<210> SEQ ID NO 10
<211> LENGTH: 89
<212> TYPE: DNA
<213> ORGANISM: Artificial Sequence
<220> FEATURE:
<223> OTHER INFORMATION: Synthetic Sequence

<400> SEQUENCE: 10
atggagacta tactgaatcc tttcatcctg aacgtgacca gtggggccct tctctgcagt   60
caagccctgt gccaggagca aggagtgtg                                     89

<210> SEQ ID NO 11
<211> LENGTH: 89
<212> TYPE: DNA
<213> ORGANISM: Artificial Sequence
<220> FEATURE:
<223> OTHER INFORMATION: Synthetic Sequence

<400> SEQUENCE: 11
atggacacta cactggggcc cttcatcctg aacgtgacca gtggggccct tctctgcagt   60
caagccctgt gccaggagca aggagtgtg                                     89

<210> SEQ ID NO 12
<211> LENGTH: 74
<212> TYPE: DNA
<213> ORGANISM: Artificial Sequence
<220> FEATURE:
<223> OTHER INFORMATION: Synthetic Sequence

<400> SEQUENCE: 12
actgttgctc tgggtgcttc tggaattgta atatgggtaa gctgggaaaa tacaagaacc   60
aaggaatcat gtca                                                     74

<210> SEQ ID NO 13
<211> LENGTH: 61
<212> TYPE: DNA
<213> ORGANISM: Artificial Sequence
<220> FEATURE:
<223> OTHER INFORMATION: Synthetic Sequence

```
<400> SEQUENCE: 13
agcaaggagt gtgtataagg aaaaccagcc acccaaaaga ctatcttcac ctcaacccag    60
a                                                                    61

<210> SEQ ID NO 14
<211> LENGTH: 43
<212> TYPE: DNA
<213> ORGANISM: Artificial Sequence
<220> FEATURE:
<223> OTHER INFORMATION: Synthetic Sequence

<400> SEQUENCE: 14
agtatatgga cactacactg aacccctaca taatcaacgt cac                      43

<210> SEQ ID NO 15
<211> LENGTH: 44
<212> TYPE: DNA
<213> ORGANISM: Artificial Sequence
<220> FEATURE:
<223> OTHER INFORMATION: Synthetic Sequence

<400> SEQUENCE: 15
attgtaatat ggggaaccct cagtaataca agaaccaagg aatc                     44

<210> SEQ ID NO 16
<211> LENGTH: 44
<212> TYPE: DNA
<213> ORGANISM: Artificial Sequence
<220> FEATURE:
<223> OTHER INFORMATION: Synthetic Sequence

<400> SEQUENCE: 16
attgtaatat ggggaaccct cgaaaataca agaaccaagg aatc                     44

<210> SEQ ID NO 17
<211> LENGTH: 44
<212> TYPE: DNA
<213> ORGANISM: Artificial Sequence
<220> FEATURE:
<223> OTHER INFORMATION: Synthetic Sequence

<400> SEQUENCE: 17
attgtaatat ggggaacctg ggaaaataca agaaccaagg aatc                     44

<210> SEQ ID NO 18
<211> LENGTH: 45
<212> TYPE: DNA
<213> ORGANISM: Artificial Sequence
<220> FEATURE:
<223> OTHER INFORMATION: Synthetic Sequence

<400> SEQUENCE: 18
acactacact gaacccttc atactcaacg tcaccctagc agcca                     45

<210> SEQ ID NO 19
<211> LENGTH: 63
<212> TYPE: DNA
<213> ORGANISM: Artificial Sequence
<220> FEATURE:
<223> OTHER INFORMATION: Synthetic Sequence

<400> SEQUENCE: 19
acactacact gaacccttc atactcaacg tcaccctatc aggcaaaatg tgtagccaag    60
tgc                                                                  63
```

<210> SEQ ID NO 20
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 20
taacaggagg tgctctgaaa gagtaagcag aggag          35

<210> SEQ ID NO 21
<211> LENGTH: 56
<212> TYPE: DNA
<213> ORGANISM: Artificial Sequence
<220> FEATURE:
<223> OTHER INFORMATION: Synthetic Sequence

<400> SEQUENCE: 21
ctaattgcgg ccgctcatta gtggtgatgg tgatgatgta tacagacacc atcagc          56

<210> SEQ ID NO 22
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 22
ctaattgcgg ccgctcatta gtggtgatgg tgatgatgaa aagcatctat acagacacc          59

<210> SEQ ID NO 23
<211> LENGTH: 61
<212> TYPE: DNA
<213> ORGANISM: Artificial Sequence
<220> FEATURE:
<223> OTHER INFORMATION: Synthetic Sequence

<400> SEQUENCE: 23
ctaattgcgg ccgctcatta gtggtgatgg tgatgatgag gttttagaaa agcatctata          60
c          61

<210> SEQ ID NO 24
<211> LENGTH: 62
<212> TYPE: DNA
<213> ORGANISM: Artificial Sequence
<220> FEATURE:
<223> OTHER INFORMATION: Synthetic Sequence

<400> SEQUENCE: 24
tccaggccca gaggaaaggc cggttgggta gcaaggggcc cctaaaagag taagcagagg          60
ag          62

<210> SEQ ID NO 25
<211> LENGTH: 75
<212> TYPE: DNA
<213> ORGANISM: Artificial Sequence
<220> FEATURE:
<223> OTHER INFORMATION: Synthetic Sequence

<400> SEQUENCE: 25
tcacttgggg cattccagac ggtggtgaag ggccggttgg gtagcaaggg gcccctaaaa          60
gagtaagcag aggag          75

<210> SEQ ID NO 26
<211> LENGTH: 58
<212> TYPE: DNA
<213> ORGANISM: Artificial Sequence
<220> FEATURE:
<223> OTHER INFORMATION: Synthetic Sequence

<400> SEQUENCE: 26
ctaattgcgg ccgctcatta gtggtgatgg tgatgatgtt ttagaaaagc atctatac    58

<210> SEQ ID NO 27
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 27
ctaattgcgg ccgctcatta aaaagcatct atacagacac c                      41

<210> SEQ ID NO 28
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 28
aattgtaata tggggaagct gggaaaatac aagaa                             35

<210> SEQ ID NO 29
<211> LENGTH: 35
<212> TYPE: DNA
<213> ORGANISM: Artificial Sequence
<220> FEATURE:
<223> OTHER INFORMATION: Synthetic Sequence

<400> SEQUENCE: 29
tggaataaca ggaggtgcag agtaagcaga ggaga                             35

<210> SEQ ID NO 30
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 30
tttggaataa caggagagta agcagaggag a                                 31

<210> SEQ ID NO 31
<211> LENGTH: 77
<212> TYPE: DNA
<213> ORGANISM: Artificial Sequence
<220> FEATURE:
<223> OTHER INFORMATION: Synthetic Sequence

<400> SEQUENCE: 31
agttttgaaa ttcctttctc tggatgagct ggagcacagc ctgggggaga gtgcggccca    60
gggtgcttct ggaattg                                                  77

<210> SEQ ID NO 32
<211> LENGTH: 38
<212> TYPE: DNA
<213> ORGANISM: Artificial Sequence

```
<220> FEATURE:
<223> OTHER INFORMATION: Synthetic Sequence

<400> SEQUENCE: 32
atgagctgga gcacagcttt ggggagagtg cggcccag                              38

<210> SEQ ID NO 33
<211> LENGTH: 48
<212> TYPE: DNA
<213> ORGANISM: Artificial Sequence
<220> FEATURE:
<223> OTHER INFORMATION: Synthetic Sequence

<400> SEQUENCE: 33
attcctttct caagatgaac ttgagcacag ctttggcgaa actgttgc                   48

<210> SEQ ID NO 34
<211> LENGTH: 56
<212> TYPE: DNA
<213> ORGANISM: Artificial Sequence
<220> FEATURE:
<223> OTHER INFORMATION: Synthetic Sequence

<400> SEQUENCE: 34
ctaattgcgg ccgctcatta gtggtgatgg tgatgatgag catctataca gacacc          56

<210> SEQ ID NO 35
<211> LENGTH: 58
<212> TYPE: DNA
<213> ORGANISM: Artificial Sequence
<220> FEATURE:
<223> OTHER INFORMATION: Synthetic Sequence

<400> SEQUENCE: 35
ctaattgcgg ccgctcatta gtggtgatgg tgatgatgac agacaccatc agcaatac        58

<210> SEQ ID NO 36
<211> LENGTH: 56
<212> TYPE: DNA
<213> ORGANISM: Artificial Sequence
<220> FEATURE:
<223> OTHER INFORMATION: Synthetic Sequence

<400> SEQUENCE: 36
ctaattgcgg ccgctcatta gtggtgatgg tgatgatgat cagcaataca cacatc          56

<210> SEQ ID NO 37
<211> LENGTH: 56
<212> TYPE: DNA
<213> ORGANISM: Artificial Sequence
<220> FEATURE:
<223> OTHER INFORMATION: Synthetic Sequence

<400> SEQUENCE: 37
ctaattgcgg ccgctcatta gtggtgatgg tgatgatgac acatcaac agcatc            56

<210> SEQ ID NO 38
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 38
ctaattgcgg ccgctcatta gtggtgatgg tgatgatgaa cagcatcagt gtcttttac      59
```

<210> SEQ ID NO 39
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 39
gttatagcgg ccgctcatta gggaggtttt agaaaagcat c                    41

<210> SEQ ID NO 40
<211> LENGTH: 44
<212> TYPE: DNA
<213> ORGANISM: Artificial Sequence
<220> FEATURE:
<223> OTHER INFORMATION: Synthetic Sequence

<400> SEQUENCE: 40
gttatagcgg ccgctcatta catgggaggt tttagaaaag catc                 44

<210> SEQ ID NO 41
<211> LENGTH: 44
<212> TYPE: DNA
<213> ORGANISM: Artificial Sequence
<220> FEATURE:
<223> OTHER INFORMATION: Synthetic Sequence

<400> SEQUENCE: 41
gttatagcgg ccgctcatta ctccatggga ggttttagaa aagc                 44

<210> SEQ ID NO 42
<211> LENGTH: 41
<212> TYPE: DNA
<213> ORGANISM: Artificial Sequence
<220> FEATURE:
<223> OTHER INFORMATION: Synthetic Sequence

<400> SEQUENCE: 42
gttatagcgg ccgctcatta tgtctccatg ggaggtttta g                    41

<210> SEQ ID NO 43
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 43
taacaggagg tgctctgaaa ttagagtaag cagaggag                        38

<210> SEQ ID NO 44
<211> LENGTH: 37
<212> TYPE: DNA
<213> ORGANISM: Artificial Sequence
<220> FEATURE:
<223> OTHER INFORMATION: Synthetic Sequence

<400> SEQUENCE: 44
tggaataaca ggaggtgctc tagagtaagc agaggag                         37

<210> SEQ ID NO 45
<211> LENGTH: 33
<212> TYPE: DNA
<213> ORGANISM: Artificial Sequence
<220> FEATURE:
<223> OTHER INFORMATION: Synthetic Sequence

```
<400> SEQUENCE: 45
tttggaataa caggaggaga gtaagcagag gag                           33

<210> SEQ ID NO 46
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 46
ctaattgcgg ccgctcatta gtggtgatgg tgatgatgat ctatacagac accatcagc   59

<210> SEQ ID NO 47
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 47
gataatgcgg ccgctcatta gtggtgatgg tgatgatgag gttcttctgt ctccatggg    59

<210> SEQ ID NO 48
<211> LENGTH: 60
<212> TYPE: DNA
<213> ORGANISM: Artificial Sequence
<220> FEATURE:
<223> OTHER INFORMATION: Synthetic Sequence

<400> SEQUENCE: 48
gataatgcgg ccgctcatta gtggtgatgg tgatgatgaa tttgaggttc ttctgtctcc   60

<210> SEQ ID NO 49
<211> LENGTH: 61
<212> TYPE: DNA
<213> ORGANISM: Artificial Sequence
<220> FEATURE:
<223> OTHER INFORMATION: Synthetic Sequence

<400> SEQUENCE: 49
gataatgcgg ccgctcatta gtggtgatgg tgatgatggt agaaaatttg aggttcttct   60
g                                                                  61

<210> SEQ ID NO 50
<211> LENGTH: 62
<212> TYPE: DNA
<213> ORGANISM: Artificial Sequence
<220> FEATURE:
<223> OTHER INFORMATION: Synthetic Sequence

<400> SEQUENCE: 50
gataatgcgg ccgctcatta gtggtgatgg tgatgatgag cattgtagaa aatttgaggt   60
tc                                                                 62

<210> SEQ ID NO 51
<211> LENGTH: 65
<212> TYPE: DNA
<213> ORGANISM: Artificial Sequence
<220> FEATURE:
<223> OTHER INFORMATION: Synthetic Sequence

<400> SEQUENCE: 51
```

```
gataatgcgg ccgctcatta gtggtgatgg tgatgatggg gtgaagcatt gtagaaaatt    60
tgagg                                                                65

<210> SEQ ID NO 52
<211> LENGTH: 60
<212> TYPE: DNA
<213> ORGANISM: Artificial Sequence
<220> FEATURE:
<223> OTHER INFORMATION: Synthetic Sequence

<400> SEQUENCE: 52
gataatgcgg ccgctcatta gtggtgatgg tgatgatgtg tggagggtga agcattgtag    60

<210> SEQ ID NO 53
<211> LENGTH: 58
<212> TYPE: DNA
<213> ORGANISM: Artificial Sequence
<220> FEATURE:
<223> OTHER INFORMATION: Synthetic Sequence

<400> SEQUENCE: 53
ctaattgcgg ccgctcatta gtggtgatgg tgatgatgtt ttagaaaagc atctatac     58

<210> SEQ ID NO 54
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 54
gttatagcgg ccgctcatta gtggtgatgg tgatgatggg gaggttttag aaaagcatc    59

<210> SEQ ID NO 55
<211> LENGTH: 62
<212> TYPE: DNA
<213> ORGANISM: Artificial Sequence
<220> FEATURE:
<223> OTHER INFORMATION: Synthetic Sequence

<400> SEQUENCE: 55
gttatagcgg ccgctcatta gtggtgatgg tgatgatgca tgggaggttt tagaaaagca    60
tc                                                                   62

<210> SEQ ID NO 56
<211> LENGTH: 62
<212> TYPE: DNA
<213> ORGANISM: Artificial Sequence
<220> FEATURE:
<223> OTHER INFORMATION: Synthetic Sequence

<400> SEQUENCE: 56
gttatagcgg ccgctcatta gtggtgatgg tgatgatgct ccatgggagg ttttagaaaa    60
gc                                                                   62

<210> SEQ ID NO 57
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 57
gttatagcgg ccgctcatta gtggtgatgg tgatgatgtg tctccatggg aggttttag    59
```

<210> SEQ ID NO 58
<211> LENGTH: 56
<212> TYPE: DNA
<213> ORGANISM: Artificial Sequence
<220> FEATURE:
<223> OTHER INFORMATION: Synthetic Sequence

<400> SEQUENCE: 58
gttatagcgg ccgctcatta gtggtgatgg tgatgatgtt ctgtctccat gggagg    56

<210> SEQ ID NO 59
<211> LENGTH: 38
<212> TYPE: DNA
<213> ORGANISM: Artificial Sequence
<220> FEATURE:
<223> OTHER INFORMATION: Synthetic Sequence

<400> SEQUENCE: 59
gttatagcgg ccgctcatta ttctgtctcc atgggagg    38

<210> SEQ ID NO 60
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 60

```
Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240
```

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Gly Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455

<210> SEQ ID NO 61
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 61

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Phe Ile Leu Asn Val Thr Ser
                325                 330                 335

Gly Ala Leu Leu Cys Ser Gln Ala Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455

<210> SEQ ID NO 62
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 62

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
            50                  55                  60

Pro Tyr Ile Asp Ser Ile Thr Gly Val Thr Val Asn Gly Gly Ile Pro
 65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
            115                 120                 125

Tyr Lys Asn Arg Ser Ile Glu Leu Val Gln Gln Asn Val Gln Leu
            130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
                180                 185                 190

His Tyr Lys Lys Pro Gly Tyr Asn Gly Ser Cys Phe Asn Val Glu Ile
            195                 200                 205

Lys Arg Asn Asp Asp Leu Ser Trp Leu Trp Asn Glu Ser Thr Ala Leu
210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
            275                 280                 285

Thr Phe Gly Glu Thr Val Ala Leu Gly Ala Ser Gly Ile Val Ile Trp
            290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Gly Pro Phe Ile Leu Asn Val Thr Ser
                325                 330                 335

Gly Ala Leu Leu Cys Ser Gln Ala Leu Cys Gln Glu Gln Gly Val Cys
                340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
            370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
            435                 440                 445

Ala Ser Pro Ser Thr Leu Ser
            450                 455

<210> SEQ ID NO 63
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 63

```
Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Val Ser Trp Glu Asn Thr Arg Thr Lys Glu Ser Cys Gln Ala Ile Lys
305                 310                 315                 320

Glu Tyr Met Asp Thr Thr Leu Gly Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365
```

```
Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
                420                 425                 430

Phe Leu Lys Pro Pro Met Glu Thr Glu Pro Gln Ile Phe Tyr Asn
                435                 440                 445

Ala Ser Pro Ser Thr Leu Ser
    450                 455

<210> SEQ ID NO 64
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 64

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
            115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
                180                 185                 190

His Tyr Lys Lys Pro Gly Tyr Asn Gly Ser Cys Phe Asn Val Glu Ile
            195                 200                 205

Lys Arg Asn Asp Asp Leu Ser Trp Leu Trp Asn Glu Ser Thr Ala Leu
            210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
                260                 265                 270
```

```
Phe Thr Asp Gln Val Leu Lys Phe Leu Ser Gln Asp Glu Leu Val Tyr
            275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455

<210> SEQ ID NO 65
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 65

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
            85                  90                  95

Thr Phe Tyr Met Pro Val Asp Asn Leu Gly Met Ala Val Ile Asp Trp
        100                 105                 110

Glu Glu Trp Arg Pro Thr Trp Ala Arg Asn Trp Lys Pro Lys Asp Val
    115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175
```

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Val Ser Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455

<210> SEQ ID NO 66
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 66

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

```
Gln Lys Ile Ser Leu Gln Asp His Leu Asp Lys Ala Lys Lys Asp Ile
             85                  90                  95

Thr Phe Tyr Met Pro Val Asp Asn Leu Gly Met Ala Val Ile Asp Trp
        100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
        130                 135             140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
        210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
        290                 295                 300

Gly Thr Leu Ser Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
        370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455

<210> SEQ ID NO 67
<211> LENGTH: 455
<212> TYPE: PRT
<213> ORGANISM: Artificial Sequence
<220> FEATURE:
<223> OTHER INFORMATION: Synthetic Sequence
```

<400> SEQUENCE: 67

```
Leu Asn Phe Arg Ala Pro Pro Val Ile Pro Asn Val Pro Phe Leu Trp
1               5                   10                  15
Ala Trp Asn Ala Pro Ser Glu Phe Cys Leu Gly Lys Phe Asp Glu Pro
            20                  25                  30
Leu Asp Met Ser Leu Phe Ser Phe Ile Gly Ser Pro Arg Ile Asn Ala
        35                  40                  45
Thr Gly Gln Gly Val Thr Ile Phe Tyr Val Asp Arg Leu Gly Tyr Tyr
    50                  55                  60
Pro Tyr Ile Asp Ser Ile Thr Gly Val Thr Val Asn Gly Gly Ile Pro
65                  70                  75                  80
Gln Lys Ile Ser Leu Gln Asp His Leu Asp Lys Ala Lys Lys Asp Ile
                85                  90                  95
Thr Phe Tyr Met Pro Val Asp Asn Leu Gly Met Ala Val Ile Asp Trp
            100                 105                 110
Glu Glu Trp Arg Pro Thr Trp Ala Arg Asn Trp Lys Pro Lys Asp Val
        115                 120                 125
Tyr Lys Asn Arg Ser Ile Glu Leu Val Gln Gln Asn Val Gln Leu
    130                 135                 140
Ser Leu Thr Glu Ala Thr Glu Lys Ala Lys Gln Glu Phe Glu Lys Ala
145                 150                 155                 160
Gly Lys Asp Phe Leu Val Glu Thr Ile Lys Leu Gly Lys Leu Leu Arg
                165                 170                 175
Pro Asn His Leu Trp Gly Tyr Tyr Leu Phe Pro Asp Cys Tyr Asn His
            180                 185                 190
His Tyr Lys Lys Pro Gly Tyr Asn Gly Ser Cys Phe Asn Val Glu Ile
        195                 200                 205
Lys Arg Asn Asp Asp Leu Ser Trp Leu Trp Asn Glu Ser Thr Ala Leu
    210                 215                 220
Tyr Pro Ser Ile Tyr Leu Asn Thr Gln Gln Ser Pro Val Ala Ala Thr
225                 230                 235                 240
Leu Tyr Val Arg Asn Arg Val Arg Glu Ala Ile Arg Val Ser Lys Ile
                245                 250                 255
Pro Asp Ala Lys Ser Pro Leu Pro Val Phe Ala Tyr Thr Arg Ile Val
            260                 265                 270
Phe Thr Asp Gln Val Leu Lys Phe Leu Ser Gln Asp Glu Leu Val Tyr
        275                 280                 285
Thr Phe Gly Glu Thr Val Ala Leu Gly Ala Ser Gly Ile Val Ile Trp
    290                 295                 300
Gly Thr Leu Glu Asn Thr Arg Thr Lys Glu Ser Cys Gln Ala Ile Lys
305                 310                 315                 320
Glu Tyr Met Asp Thr Thr Leu Asn Pro Tyr Ile Ile Asn Val Thr Leu
                325                 330                 335
Ala Ala Lys Met Cys Ser Gln Val Leu Cys Gln Glu Gln Gly Val Cys
            340                 345                 350
Ile Arg Lys Asn Trp Asn Ser Ser Asp Tyr Leu His Leu Asn Pro Asp
        355                 360                 365
Asn Phe Ala Ile Gln Leu Glu Lys Gly Gly Lys Phe Thr Val Arg Gly
    370                 375                 380
Lys Pro Thr Leu Glu Asp Leu Glu Gln Phe Ser Glu Lys Phe Tyr Cys
385                 390                 395                 400
Ser Cys Tyr Ser Thr Leu Ser Cys Lys Glu Lys Ala Asp Val Lys Asp
```

```
                    405                 410                 415
Thr Asp Ala Val Asp Val Cys Ile Ala Asp Gly Val Cys Ile Asp Ala
                420                 425                 430

Phe Leu Lys Pro Pro Met Glu Thr Glu Glu Pro Gln Ile Phe Tyr Asn
            435                 440                 445

Ala Ser Pro Ser Thr Leu Ser
        450                 455

<210> SEQ ID NO 68
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 68

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Trp Glu Asn Thr Arg Thr Lys Glu Ser Cys Gln Ala Ile Lys
```

```
            305                 310                 315                 320
Glu Tyr Met Asp Thr Thr Leu Asn Pro Tyr Ile Ile Asn Val Thr Leu
                    325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
                355                 360                 365

Asn Phe Ala Ile Gln Leu Glu Lys Gly Gly Lys Phe Thr Val Arg Gly
            370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                    405                 410                 415

Thr Asp Ala Val Asp Val Cys Ile Ala Asp Gly Val Cys Ile Asp Ala
                420                 425                 430

Phe Leu Lys Pro Pro Met Glu Thr Glu Glu Pro Gln Ile Phe Tyr Asn
            435                 440                 445

Ala Ser Pro Ser Thr Leu Ser
450                 455

<210> SEQ ID NO 69
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 69

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
```

```
            210                 215                 220
Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
                260                 265                 270

Phe Thr Asp Gln Val Leu Lys Phe Leu Ser Gln Asp Glu Leu Val Tyr
                275                 280                 285

Thr Phe Gly Glu Thr Val Ala Leu Gly Ala Ser Gly Ile Val Ile Trp
                290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Phe Ile Leu Asn Val Thr Leu
                325                 330                 335

Ala Ala Lys Met Cys Ser Gln Val Leu Cys Gln Glu Gln Gly Val Cys
                340                 345                 350

Ile Arg Lys Asn Trp Asn Ser Ser Asp Tyr Leu His Leu Asn Pro Asp
                355                 360                 365

Asn Phe Ala Ile Gln Leu Glu Lys Gly Gly Lys Phe Thr Val Arg Gly
                370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
                420                 425                 430

Phe Leu Lys Pro Pro Met Glu Thr Glu Pro Gln Ile Phe Tyr Asn
                435                 440                 445

Ala Ser Pro Ser Thr Leu Ser
    450                 455

<210> SEQ ID NO 70
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 70

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
                35                  40                  45

Thr Gly Gln Gly Val Thr Ile Phe Tyr Val Asp Arg Leu Gly Tyr Tyr
                50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
```

```
            115                 120                 125
Tyr Lys Asn Arg Ser Ile Glu Leu Val Gln Gln Asn Val Gln Leu
            130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
            195                 200                 205

Lys Arg Asn Asp Asp Leu Ser Trp Leu Trp Asn Glu Ser Thr Ala Leu
            210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
            275                 280                 285

Thr Phe Gly Glu Thr Val Ala Leu Gly Ala Ser Gly Ile Val Ile Trp
            290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Phe Ile Leu Asn Val Thr Ser
                325                 330                 335

Gly Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
            370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
            435                 440                 445

Ala Ser Pro Ser Thr Leu Ser
            450                 455

<210> SEQ ID NO 71
<211> LENGTH: 453
<212> TYPE: PRT
<213> ORGANISM: Artificial Sequence
<220> FEATURE:
<223> OTHER INFORMATION: Synthetic Sequence

<400> SEQUENCE: 71

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
```

```
            20                  25                  30
Met Ser Leu Phe Ser Phe Ile Gly Ser Pro Arg Ile Asn Ala Thr Gly
            35                  40                  45

Gln Gly Val Thr Ile Phe Tyr Val Asp Arg Leu Gly Tyr Tyr Pro Tyr
            50                  55                  60

Ile Asp Ser Ile Thr Gly Val Thr Val Asn Gly Ile Pro Gln Lys
65                  70                  75                  80

Ile Ser Leu Gln Asp His Leu Asp Lys Ala Lys Lys Asp Ile Thr Phe
                    85                  90                  95

Tyr Met Pro Val Asp Asn Leu Gly Met Ala Val Ile Asp Trp Glu Glu
                    100                 105                 110

Trp Arg Pro Thr Trp Ala Arg Asn Trp Lys Pro Lys Asp Val Tyr Lys
                    115                 120                 125

Asn Arg Ser Ile Glu Leu Val Gln Gln Asn Val Gln Leu Ser Leu
        130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                    165                 170                 175

His Leu Trp Gly Tyr Tyr Leu Phe Pro Asp Cys Tyr Asn His His Tyr
                    180                 185                 190

Lys Lys Pro Gly Tyr Asn Gly Ser Cys Phe Asn Val Glu Ile Lys Arg
                    195                 200                 205

Asn Asp Asp Leu Ser Trp Leu Trp Asn Glu Ser Thr Ala Leu Tyr Pro
        210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                    245                 250                 255

Ala Lys Ser Pro Leu Pro Val Phe Ala Tyr Thr Arg Ile Val Phe Thr
                    260                 265                 270

Asp Gln Val Leu Lys Phe Leu Ser Gln Asp Glu Leu Val Tyr Thr Phe
                    275                 280                 285

Gly Glu Thr Val Ala Leu Gly Ala Ser Gly Ile Val Ile Trp Gly Thr
                    290                 295                 300

Leu Ser Ile Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                    325                 330                 335

Lys Met Cys Ser Gln Val Leu Cys Gln Glu Gln Gly Val Cys Ile Arg
                    340                 345                 350

Lys Asn Trp Asn Ser Ser Asp Tyr Leu His Leu Asn Pro Asp Asn Phe
                    355                 360                 365

Ala Ile Gln Leu Glu Lys Gly Gly Lys Phe Thr Val Arg Gly Lys Pro
                    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                    405                 410                 415

Ala Val Asp Val Cys Ile Ala Asp Gly Val Cys Ile Asp Ala Phe Leu
                    420                 425                 430

Lys Pro Pro Met Glu Thr Glu Pro Gln Ile Phe Tyr Asn Ala Ser
                    435                 440                 445
```

Pro Ser Thr Leu Ser
    450

<210> SEQ ID NO 72
<211> LENGTH: 430
<212> TYPE: PRT
<213> ORGANISM: Artificial Sequence
<220> FEATURE:
<223> OTHER INFORMATION: Synthetic Sequence

<400> SEQUENCE: 72

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

```
Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile
                420                 425                 430

<210> SEQ ID NO 73
<211> LENGTH: 433
<212> TYPE: PRT
<213> ORGANISM: Artificial Sequence
<220> FEATURE:
<223> OTHER INFORMATION: Synthetic Sequence

<400> SEQUENCE: 73

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
            130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285
```

```
Thr Phe Gly Glu Thr Val Ala Leu Gly Ala Ser Gly Ile Val Ile Trp
    290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe

<210> SEQ ID NO 74
<211> LENGTH: 436
<212> TYPE: PRT
<213> ORGANISM: Artificial Sequence
<220> FEATURE:
<223> OTHER INFORMATION: Synthetic Sequence

<400> SEQUENCE: 74

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
            85                  90                  95

Thr Phe Tyr Met Pro Val Asp Asn Leu Gly Met Ala Val Ile Asp Trp
        100                 105                 110

Glu Glu Trp Arg Pro Thr Trp Ala Arg Asn Trp Lys Pro Lys Asp Val
    115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205
```

```
Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
                260                 265                 270

Phe Thr Asp Gln Val Leu Lys Phe Leu Ser Gln Asp Glu Leu Val Tyr
            275                 280                 285

Thr Phe Gly Glu Thr Val Ala Leu Gly Ala Ser Gly Ile Val Ile Trp
        290                 295                 300

Gly Thr Leu Ser Ile Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
                340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
        370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
                420                 425                 430

Phe Leu Lys Pro
        435

<210> SEQ ID NO 75
<211> LENGTH: 452
<212> TYPE: PRT
<213> ORGANISM: Artificial Sequence
<220> FEATURE:
<223> OTHER INFORMATION: Synthetic Sequence

<400> SEQUENCE: 75

Phe Arg Gly Pro Leu Leu Pro Asn Arg Pro Phe Leu Trp Ala Trp Asn
1               5                   10                  15

Ala Pro Ser Glu Phe Cys Leu Gly Lys Phe Asp Glu Pro Leu Asp Met
            20                  25                  30

Ser Leu Phe Ser Phe Ile Gly Ser Pro Arg Ile Asn Ala Thr Gly Gln
        35                  40                  45

Gly Val Thr Ile Phe Tyr Val Asp Arg Leu Gly Tyr Tyr Pro Tyr Ile
    50                  55                  60

Asp Ser Ile Thr Gly Val Thr Val Asn Gly Gly Ile Pro Gln Lys Ile
65                  70                  75                  80

Ser Leu Gln Asp His Leu Asp Lys Ala Lys Lys Asp Ile Thr Phe Tyr
                85                  90                  95

Met Pro Val Asp Asn Leu Gly Met Ala Val Ile Asp Trp Glu Glu Trp
                100                 105                 110

Arg Pro Thr Trp Ala Arg Asn Trp Lys Pro Lys Asp Val Tyr Lys Asn
            115                 120                 125
```

```
Arg Ser Ile Glu Leu Val Gln Gln Asn Val Gln Leu Ser Leu Thr
    130                 135                 140
Glu Ala Thr Glu Lys Ala Lys Gln Glu Phe Glu Lys Ala Gly Lys Asp
145                 150                 155                 160
Phe Leu Val Glu Thr Ile Lys Leu Gly Lys Leu Leu Arg Pro Asn His
                165                 170                 175
Leu Trp Gly Tyr Tyr Leu Phe Pro Asp Cys Tyr Asn His His Tyr Lys
            180                 185                 190
Lys Pro Gly Tyr Asn Gly Ser Cys Phe Asn Val Glu Ile Lys Arg Asn
        195                 200                 205
Asp Asp Leu Ser Trp Leu Trp Asn Glu Ser Thr Ala Leu Tyr Pro Ser
    210                 215                 220
Ile Tyr Leu Asn Thr Gln Gln Ser Pro Val Ala Ala Thr Leu Tyr Val
225                 230                 235                 240
Arg Asn Arg Val Arg Glu Ala Ile Arg Val Ser Lys Ile Pro Asp Ala
                245                 250                 255
Lys Ser Pro Leu Pro Val Phe Ala Tyr Thr Arg Ile Val Phe Thr Asp
            260                 265                 270
Gln Val Leu Lys Phe Leu Ser Gln Asp Glu Leu Val Tyr Thr Phe Gly
        275                 280                 285
Glu Thr Val Ala Leu Gly Ala Ser Gly Ile Val Ile Trp Gly Thr Leu
    290                 295                 300
Ser Ile Thr Arg Thr Lys Glu Ser Cys Gln Ala Ile Lys Glu Tyr Met
305                 310                 315                 320
Asp Thr Thr Leu Asn Pro Tyr Ile Ile Asn Val Thr Leu Ala Ala Lys
                325                 330                 335
Met Cys Ser Gln Val Leu Cys Gln Glu Gln Gly Val Cys Ile Arg Lys
            340                 345                 350
Asn Trp Asn Ser Ser Asp Tyr Leu His Leu Asn Pro Asp Asn Phe Ala
        355                 360                 365
Ile Gln Leu Glu Lys Gly Gly Lys Phe Thr Val Arg Gly Lys Pro Thr
    370                 375                 380
Leu Glu Asp Leu Glu Gln Phe Ser Glu Lys Phe Tyr Cys Ser Cys Tyr
385                 390                 395                 400
Ser Thr Leu Ser Cys Lys Glu Lys Ala Asp Val Lys Asp Thr Asp Ala
                405                 410                 415
Val Asp Val Cys Ile Ala Asp Gly Val Cys Ile Asp Ala Phe Leu Lys
            420                 425                 430
Pro Pro Met Glu Thr Glu Glu Pro Gln Ile Phe Tyr Asn Ala Ser Pro
        435                 440                 445
Ser Thr Leu Ser
    450

<210> SEQ ID NO 76
<211> LENGTH: 452
<212> TYPE: PRT
<213> ORGANISM: Artificial Sequence
<220> FEATURE:
<223> OTHER INFORMATION: Synthetic Sequence

<400> SEQUENCE: 76

Phe Arg Gly Pro Leu Leu Pro Asn Arg Pro Phe Thr Thr Val Trp Asn
1               5                   10                  15
Ala Pro Ser Glu Phe Cys Leu Gly Lys Phe Asp Glu Pro Leu Asp Met
            20                  25                  30
```

```
Ser Leu Phe Ser Phe Ile Gly Ser Pro Arg Ile Asn Ala Thr Gly Gln
             35                  40                  45

Gly Val Thr Ile Phe Tyr Val Asp Arg Leu Gly Tyr Tyr Pro Tyr Ile
 50                  55                  60

Asp Ser Ile Thr Gly Val Thr Val Asn Gly Gly Ile Pro Gln Lys Ile
 65                  70                  75                  80

Ser Leu Gln Asp His Leu Asp Lys Ala Lys Lys Asp Ile Thr Phe Tyr
                 85                  90                  95

Met Pro Val Asp Asn Leu Gly Met Ala Val Ile Asp Trp Glu Trp
                100                 105                 110

Arg Pro Thr Trp Ala Arg Asn Trp Lys Pro Lys Asp Val Tyr Lys Asn
            115                 120                 125

Arg Ser Ile Glu Leu Val Gln Gln Asn Val Gln Leu Ser Leu Thr
130                 135                 140

Glu Ala Thr Glu Lys Ala Lys Gln Glu Phe Glu Lys Ala Gly Lys Asp
145                 150                 155                 160

Phe Leu Val Glu Thr Ile Lys Leu Gly Lys Leu Leu Arg Pro Asn His
                165                 170                 175

Leu Trp Gly Tyr Tyr Leu Phe Pro Asp Cys Tyr Asn His His Tyr Lys
            180                 185                 190

Lys Pro Gly Tyr Asn Gly Ser Cys Phe Asn Val Glu Ile Lys Arg Asn
            195                 200                 205

Asp Asp Leu Ser Trp Leu Trp Asn Glu Ser Thr Ala Leu Tyr Pro Ser
210                 215                 220

Ile Tyr Leu Asn Thr Gln Gln Ser Pro Val Ala Ala Thr Leu Tyr Val
225                 230                 235                 240

Arg Asn Arg Val Arg Glu Ala Ile Arg Val Ser Lys Ile Pro Asp Ala
            245                 250                 255

Lys Ser Pro Leu Pro Val Phe Ala Tyr Thr Arg Ile Val Phe Thr Asp
                260                 265                 270

Gln Val Leu Lys Phe Leu Ser Gln Asp Glu Leu Val Tyr Thr Phe Gly
            275                 280                 285

Glu Thr Val Ala Leu Gly Ala Ser Gly Ile Val Ile Trp Gly Thr Leu
290                 295                 300

Ser Ile Thr Arg Thr Lys Glu Ser Cys Gln Ala Ile Lys Glu Tyr Met
305                 310                 315                 320

Asp Thr Thr Leu Asn Pro Tyr Ile Ile Asn Val Thr Leu Ala Ala Lys
                325                 330                 335

Met Cys Ser Gln Val Leu Cys Gln Gly Val Cys Ile Arg Lys
            340                 345                 350

Asn Trp Asn Ser Ser Asp Tyr Leu His Leu Asn Pro Asp Asn Phe Ala
            355                 360                 365

Ile Gln Leu Glu Lys Gly Gly Lys Phe Thr Val Arg Gly Lys Pro Thr
370                 375                 380

Leu Glu Asp Leu Glu Gln Phe Ser Glu Lys Phe Tyr Cys Ser Cys Tyr
385                 390                 395                 400

Ser Thr Leu Ser Cys Lys Glu Lys Ala Asp Val Lys Asp Thr Asp Ala
                405                 410                 415

Val Asp Val Cys Ile Ala Asp Gly Val Cys Ile Asp Ala Phe Leu Lys
                420                 425                 430

Pro Pro Met Glu Thr Glu Glu Pro Gln Ile Phe Tyr Asn Ala Ser Pro
                435                 440                 445

Ser Thr Leu Ser
```

<210> SEQ ID NO 77
<211> LENGTH: 433
<212> TYPE: PRT
<213> ORGANISM: Artificial Sequence
<220> FEATURE:
<223> OTHER INFORMATION: Synthetic Sequence

<400> SEQUENCE: 77

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe

```
                355                 360                 365
Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
                420                 425                 430

Lys

<210> SEQ ID NO 78
<211> LENGTH: 431
<212> TYPE: PRT
<213> ORGANISM: Artificial Sequence
<220> FEATURE:
<223> OTHER INFORMATION: Synthetic Sequence

<400> SEQUENCE: 78

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
                20                  25                  30

Met Ser Leu Phe Ser Phe Ile Gly Ser Pro Arg Ile Asn Ala Thr Gly
            35                  40                  45

Gln Gly Val Thr Ile Phe Tyr Val Asp Arg Leu Gly Tyr Tyr Pro Tyr
        50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285
```

-continued

```
Gly Glu Thr Val Ala Leu Gly Ala Ser Gly Ile Val Ile Trp Gly Thr
        290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
            325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
            405                 410                 415

Ala Val Asp Val Cys Ile Ala Asp Gly Val Cys Ile Asp Ala Phe
            420                 425                 430

<210> SEQ ID NO 79
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 79

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220
```

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
            245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
            275                 280                 285

Thr Phe Gly Glu Thr Val Ala Leu Gly Ala Ser Gly Ile Val Ile Trp
            290                 295                 300

Gly Ser Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
            435                 440                 445

Ala Ser Pro Ser Thr Leu Ser
    450                 455

<210> SEQ ID NO 80
<211> LENGTH: 451
<212> TYPE: PRT
<213> ORGANISM: Artificial Sequence
<220> FEATURE:
<223> OTHER INFORMATION: Synthetic Sequence

<400> SEQUENCE: 80

Ala Pro Pro Val Ile Pro Asn Val Pro Phe Leu Trp Ala Trp Asn Ala
1               5                   10                  15

Pro Ser Glu Phe Cys Leu Gly Lys Phe Asp Glu Pro Leu Asp Met Ser
            20                  25                  30

Leu Phe Ser Phe Ile Gly Ser Pro Arg Ile Asn Ala Thr Gly Gln Gly
        35                  40                  45

Val Thr Ile Phe Tyr Val Asp Arg Leu Gly Tyr Tyr Pro Tyr Ile Asp
    50                  55                  60

Ser Ile Thr Gly Val Thr Val Asn Gly Gly Ile Pro Gln Lys Ile Ser
65                  70                  75                  80

Leu Gln Asp His Leu Asp Lys Ala Lys Lys Asp Ile Thr Phe Tyr Met
                85                  90                  95

Pro Val Asp Asn Leu Gly Met Ala Val Ile Asp Trp Glu Glu Trp Arg
            100                 105                 110

Pro Thr Trp Ala Arg Asn Trp Lys Pro Lys Asp Val Tyr Lys Asn Arg
        115                 120                 125

Ser Ile Glu Leu Val Gln Gln Asn Val Gln Leu Ser Leu Thr Glu
            130                 135                 140

Ala Thr Glu Lys Ala Lys Gln Glu Phe Glu Lys Ala Gly Lys Asp Phe
145                 150                 155                 160

Leu Val Glu Thr Ile Lys Leu Gly Lys Leu Leu Arg Pro Asn His Leu
                165                 170                 175

Trp Gly Tyr Tyr Leu Phe Pro Asp Cys Tyr Asn His His Tyr Lys Lys
            180                 185                 190

Pro Gly Tyr Asn Gly Ser Cys Phe Asn Val Glu Ile Lys Arg Asn Asp
            195                 200                 205

Asp Leu Ser Trp Leu Trp Asn Glu Ser Thr Ala Leu Tyr Pro Ser Ile
210                 215                 220

Tyr Leu Asn Thr Gln Gln Ser Pro Val Ala Ala Thr Leu Tyr Val Arg
225                 230                 235                 240

Asn Arg Val Arg Glu Ala Ile Arg Val Ser Lys Ile Pro Asp Ala Lys
                245                 250                 255

Ser Pro Leu Pro Val Phe Ala Tyr Thr Arg Ile Val Phe Thr Asp Gln
            260                 265                 270

Val Leu Lys Phe Leu Ser Gln Asp Glu Leu Val Tyr Thr Phe Gly Glu
            275                 280                 285

Thr Val Ala Leu Gly Ala Ser Gly Ile Val Ile Trp Gly Thr Leu Ser
290                 295                 300

Ile Thr Arg Thr Lys Glu Ser Cys Gln Ala Ile Lys Glu Tyr Met Asp
305                 310                 315                 320

Thr Thr Leu Asn Pro Tyr Ile Ile Asn Val Thr Leu Ala Ala Lys Met
                325                 330                 335

Cys Ser Gln Val Leu Cys Gln Glu Gln Gly Val Cys Ile Arg Lys Asn
            340                 345                 350

Trp Asn Ser Ser Asp Tyr Leu His Leu Asn Pro Asp Asn Phe Ala Ile
            355                 360                 365

Gln Leu Glu Lys Gly Gly Lys Phe Thr Val Arg Gly Lys Pro Thr Leu
370                 375                 380

Glu Asp Leu Glu Gln Phe Ser Glu Lys Phe Tyr Cys Ser Cys Tyr Ser
385                 390                 395                 400

Thr Leu Ser Cys Lys Glu Lys Ala Asp Val Lys Asp Thr Asp Ala Val
                405                 410                 415

Asp Val Cys Ile Ala Asp Gly Val Cys Ile Asp Ala Phe Leu Lys Pro
            420                 425                 430

Pro Met Glu Thr Glu Glu Pro Gln Ile Phe Tyr Asn Ala Ser Pro Ser
            435                 440                 445

Thr Leu Ser
    450

<210> SEQ ID NO 81
<211> LENGTH: 449
<212> TYPE: PRT
<213> ORGANISM: Artificial Sequence
<220> FEATURE:
<223> OTHER INFORMATION: Synthetic Sequence

<400> SEQUENCE: 81

Pro Val Ile Pro Asn Val Pro Phe Leu Trp Ala Trp Asn Ala Pro Ser
1               5                   10                  15

Glu Phe Cys Leu Gly Lys Phe Asp Glu Pro Leu Asp Met Ser Leu Phe
            20                  25                  30

```
Ser Phe Ile Gly Ser Pro Arg Ile Asn Ala Thr Gly Gln Gly Val Thr
         35                  40                  45

Ile Phe Tyr Val Asp Arg Leu Gly Tyr Tyr Pro Tyr Ile Asp Ser Ile
 50                  55                  60

Thr Gly Val Thr Val Asn Gly Gly Ile Pro Gln Lys Ile Ser Leu Gln
 65                  70                  75                  80

Asp His Leu Asp Lys Ala Lys Lys Asp Ile Thr Phe Tyr Met Pro Val
                 85                  90                  95

Asp Asn Leu Gly Met Ala Val Ile Asp Trp Glu Trp Arg Pro Thr
                100                 105                 110

Trp Ala Arg Asn Trp Lys Pro Lys Asp Val Tyr Lys Asn Arg Ser Ile
             115                 120                 125

Glu Leu Val Gln Gln Gln Asn Val Gln Leu Ser Leu Thr Glu Ala Thr
         130                 135                 140

Glu Lys Ala Lys Gln Glu Phe Glu Lys Ala Gly Lys Asp Phe Leu Val
145                 150                 155                 160

Glu Thr Ile Lys Leu Gly Lys Leu Leu Arg Pro Asn His Leu Trp Gly
                 165                 170                 175

Tyr Tyr Leu Phe Pro Asp Cys Tyr Asn His His Tyr Lys Lys Pro Gly
             180                 185                 190

Tyr Asn Gly Ser Cys Phe Asn Val Glu Ile Lys Arg Asn Asp Asp Leu
         195                 200                 205

Ser Trp Leu Trp Asn Glu Ser Thr Ala Leu Tyr Pro Ser Ile Tyr Leu
     210                 215                 220

Asn Thr Gln Gln Ser Pro Val Ala Ala Thr Leu Tyr Val Arg Asn Arg
225                 230                 235                 240

Val Arg Glu Ala Ile Arg Val Ser Lys Ile Pro Asp Ala Lys Ser Pro
                 245                 250                 255

Leu Pro Val Phe Ala Tyr Thr Arg Ile Val Phe Thr Asp Gln Val Leu
             260                 265                 270

Lys Phe Leu Ser Gln Asp Glu Leu Val Tyr Thr Phe Gly Glu Thr Val
         275                 280                 285

Ala Leu Gly Ala Ser Gly Ile Val Ile Trp Gly Thr Leu Ser Ile Thr
     290                 295                 300

Arg Thr Lys Glu Ser Cys Gln Ala Ile Lys Glu Tyr Met Asp Thr Thr
305                 310                 315                 320

Leu Asn Pro Tyr Ile Ile Asn Val Thr Leu Ala Ala Lys Met Cys Ser
                 325                 330                 335

Gln Val Leu Cys Gln Glu Gln Gly Val Cys Ile Arg Lys Asn Trp Asn
             340                 345                 350

Ser Ser Asp Tyr Leu His Leu Asn Pro Asp Asn Phe Ala Ile Gln Leu
         355                 360                 365

Glu Lys Gly Gly Lys Phe Thr Val Arg Gly Lys Pro Thr Leu Glu Asp
     370                 375                 380

Leu Glu Gln Phe Ser Glu Lys Phe Tyr Cys Ser Cys Tyr Ser Thr Leu
385                 390                 395                 400

Ser Cys Lys Glu Lys Ala Asp Val Lys Asp Thr Asp Ala Val Asp Val
                 405                 410                 415

Cys Ile Ala Asp Gly Val Cys Ile Asp Ala Phe Leu Lys Pro Pro Met
             420                 425                 430

Glu Thr Glu Glu Pro Gln Ile Phe Tyr Asn Ala Ser Pro Ser Thr Leu
         435                 440                 445
```

Ser

<210> SEQ ID NO 82
<211> LENGTH: 432
<212> TYPE: PRT
<213> ORGANISM: Artificial Sequence
<220> FEATURE:
<223> OTHER INFORMATION: Synthetic Sequence

<400> SEQUENCE: 82

```
Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
```

```
              355                 360                 365
Asn Phe Ala Ile Gln Leu Glu Lys Gly Gly Lys Phe Thr Val Arg Gly
            370                 375                 380
Lys Pro Thr Leu Glu Asp Leu Glu Gln Phe Ser Glu Lys Phe Tyr Cys
385                 390                 395                 400
Ser Cys Tyr Ser Thr Leu Ser Cys Lys Glu Lys Ala Asp Val Lys Asp
                405                 410                 415
Thr Asp Ala Val Asp Val Cys Ile Ala Asp Gly Val Cys Ile Asp Ala
            420                 425                 430

<210> SEQ ID NO 83
<211> LENGTH: 429
<212> TYPE: PRT
<213> ORGANISM: Artificial Sequence
<220> FEATURE:
<223> OTHER INFORMATION: Synthetic Sequence

<400> SEQUENCE: 83

Leu Asn Phe Arg Ala Pro Pro Val Ile Pro Asn Val Pro Phe Leu Trp
1               5                   10                  15
Ala Trp Asn Ala Pro Ser Glu Phe Cys Leu Gly Lys Phe Asp Glu Pro
            20                  25                  30
Leu Asp Met Ser Leu Phe Ser Phe Ile Gly Ser Pro Arg Ile Asn Ala
        35                  40                  45
Thr Gly Gln Gly Val Thr Ile Phe Tyr Val Asp Arg Leu Gly Tyr Tyr
    50                  55                  60
Pro Tyr Ile Asp Ser Ile Thr Gly Val Thr Val Asn Gly Gly Ile Pro
65                  70                  75                  80
Gln Lys Ile Ser Leu Gln Asp His Leu Asp Lys Ala Lys Lys Asp Ile
                85                  90                  95
Thr Phe Tyr Met Pro Val Asp Asn Leu Gly Met Ala Val Ile Asp Trp
            100                 105                 110
Glu Glu Trp Arg Pro Thr Trp Ala Arg Asn Trp Lys Pro Lys Asp Val
        115                 120                 125
Tyr Lys Asn Arg Ser Ile Glu Leu Val Gln Gln Asn Val Gln Leu
    130                 135                 140
Ser Leu Thr Glu Ala Thr Glu Lys Ala Lys Gln Glu Phe Glu Lys Ala
145                 150                 155                 160
Gly Lys Asp Phe Leu Val Glu Thr Ile Lys Leu Gly Lys Leu Leu Arg
                165                 170                 175
Pro Asn His Leu Trp Gly Tyr Tyr Leu Phe Pro Asp Cys Tyr Asn His
            180                 185                 190
His Tyr Lys Lys Pro Gly Tyr Asn Gly Ser Cys Phe Asn Val Glu Ile
        195                 200                 205
Lys Arg Asn Asp Asp Leu Ser Trp Leu Trp Asn Glu Ser Thr Ala Leu
    210                 215                 220
Tyr Pro Ser Ile Tyr Leu Asn Thr Gln Gln Ser Pro Val Ala Ala Thr
225                 230                 235                 240
Leu Tyr Val Arg Asn Arg Val Arg Glu Ala Ile Arg Val Ser Lys Ile
                245                 250                 255
Pro Asp Ala Lys Ser Pro Leu Pro Val Phe Ala Tyr Thr Arg Ile Val
            260                 265                 270
Phe Thr Asp Gln Val Leu Lys Phe Leu Ser Gln Asp Glu Leu Val Tyr
        275                 280                 285
Thr Phe Gly Glu Thr Val Ala Leu Gly Ala Ser Gly Ile Val Ile Trp
```

```
                    290                 295                 300
Gly Thr Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                    325                 330                 335

Ala Ala Lys Met Cys Ser Gln Val Leu Cys Gln Glu Gln Gly Val Cys
                340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
        370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys
            420                 425

<210> SEQ ID NO 84
<211> LENGTH: 426
<212> TYPE: PRT
<213> ORGANISM: Artificial Sequence
<220> FEATURE:
<223> OTHER INFORMATION: Synthetic Sequence

<400> SEQUENCE: 84

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
            115                 120                 125

Tyr Lys Asn Arg Ser Ile Glu Leu Val Gln Gln Asn Val Gln Leu
        130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
```

```
225                 230                 235                 240
Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
                260                 265                 270

Phe Thr Asp Gln Val Leu Lys Phe Leu Ser Gln Asp Glu Leu Val Tyr
                275                 280                 285

Thr Phe Gly Glu Thr Val Ala Leu Gly Ala Ser Gly Ile Val Ile Trp
            290                 295                 300

Gly Thr Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
                340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
            370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp
                420                 425

<210> SEQ ID NO 85
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 85

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
            115                 120                 125

Tyr Lys Asn Arg Ser Ile Glu Leu Val Gln Gln Asn Val Gln Leu
            130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
```

```
                165                 170                 175
Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
            195                 200                 205

Lys Arg Asn Asp Asp Leu Ser Trp Leu Trp Asn Glu Ser Thr Ala Leu
210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
            275                 280                 285

Thr Phe Gly Glu Thr Val Ala Leu Gly Ala Ser Gly Ile Val Ile Trp
            290                 295                 300

Gly Thr Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
            370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys
            420

<210> SEQ ID NO 86
<211> LENGTH: 420
<212> TYPE: PRT
<213> ORGANISM: Artificial Sequence
<220> FEATURE:
<223> OTHER INFORMATION: Synthetic Sequence

<400> SEQUENCE: 86

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
```

```
                100             105             110
Glu Glu Trp Arg Pro Thr Trp Ala Arg Asn Trp Lys Pro Lys Asp Val
            115                 120             125

Tyr Lys Asn Arg Ser Ile Glu Leu Val Gln Gln Gln Asn Val Gln Leu
            130                 135             140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170             175

Pro Asn His Leu Trp Gly Tyr Tyr Leu Phe Pro Asp Cys Tyr Asn His
            180                 185             190

His Tyr Lys Lys Pro Gly Tyr Asn Gly Ser Cys Phe Asn Val Glu Ile
            195                 200             205

Lys Arg Asn Asp Asp Leu Ser Trp Leu Trp Asn Glu Ser Thr Ala Leu
            210                 215             220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250             255

Pro Asp Ala Lys Ser Pro Leu Pro Val Phe Ala Tyr Thr Arg Ile Val
            260                 265             270

Phe Thr Asp Gln Val Leu Lys Phe Leu Ser Gln Asp Glu Leu Val Tyr
            275                 280             285

Thr Phe Gly Glu Thr Val Ala Leu Gly Ala Ser Gly Ile Val Ile Trp
            290                 295             300

Gly Thr Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330             335

Ala Ala Lys Met Cys Ser Gln Val Leu Cys Gln Glu Gln Gly Val Cys
            340                 345             350

Ile Arg Lys Asn Trp Asn Ser Ser Asp Tyr Leu His Leu Asn Pro Asp
            355                 360             365

Asn Phe Ala Ile Gln Leu Glu Lys Gly Gly Lys Phe Thr Val Arg Gly
            370                 375             380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410             415

Thr Asp Ala Val
            420

<210> SEQ ID NO 87
<211> LENGTH: 433
<212> TYPE: PRT
<213> ORGANISM: Artificial Sequence
<220> FEATURE:
<223> OTHER INFORMATION: Synthetic Sequence

<400> SEQUENCE: 87

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
```

35                  40                  45
Gln Gly Val Thr Ile Phe Tyr Val Asp Arg Leu Gly Tyr Tyr Pro Tyr
 50                  55                  60

Ile Asp Ser Ile Thr Gly Val Thr Val Asn Gly Ile Pro Gln Lys
 65                  70                  75                  80

Ile Ser Leu Gln Asp His Leu Asp Lys Ala Lys Lys Asp Ile Thr Phe
                 85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
            115                 120                 125

Asn Arg Ser Ile Glu Leu Val Gln Gln Asn Val Gln Leu Ser Leu
            130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
            195                 200                 205

Asn Asp Asp Leu Ser Trp Leu Trp Asn Glu Ser Thr Ala Leu Tyr Pro
210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
            275                 280                 285

Gly Glu Thr Val Ala Leu Gly Ala Ser Gly Ile Val Ile Trp Gly Ser
290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
            355                 360                 365

Ala Ile Gln Leu Glu Lys Gly Gly Lys Phe Thr Val Arg Gly Lys Pro
            370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys

<210> SEQ ID NO 88
<211> LENGTH: 435

<212> TYPE: PRT
<213> ORGANISM: Artificial Sequence
<220> FEATURE:
<223> OTHER INFORMATION: Synthetic Sequence

<400> SEQUENCE: 88

```
Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380
```

-continued

```
Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
            405                 410                 415

Ala Val Asp Val Cys Ile Ala Asp Gly Val Cys Ile Asp Ala Phe Leu
        420                 425                 430

Lys Pro Pro
        435

<210> SEQ ID NO 89
<211> LENGTH: 436
<212> TYPE: PRT
<213> ORGANISM: Artificial Sequence
<220> FEATURE:
<223> OTHER INFORMATION: Synthetic Sequence

<400> SEQUENCE: 89

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300
```

```
Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
            325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
            355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met
            435

<210> SEQ ID NO 90
<211> LENGTH: 437
<212> TYPE: PRT
<213> ORGANISM: Artificial Sequence
<220> FEATURE:
<223> OTHER INFORMATION: Synthetic Sequence

<400> SEQUENCE: 90

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220
```

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
            245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
            275                 280                 285

Gly Glu Thr Val Ala Leu Gly Ala Ser Gly Ile Val Ile Trp Gly Thr
            290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
            325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
            355                 360                 365

Ala Ile Gln Leu Glu Lys Gly Gly Lys Phe Thr Val Arg Gly Lys Pro
            370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
            405                 410                 415

Ala Val Asp Val Cys Ile Ala Asp Gly Val Cys Ile Asp Ala Phe Leu
            420                 425                 430

Lys Pro Pro Met Glu
        435

<210> SEQ ID NO 91
<211> LENGTH: 438
<212> TYPE: PRT
<213> ORGANISM: Artificial Sequence
<220> FEATURE:
<223> OTHER INFORMATION: Synthetic Sequence

<400> SEQUENCE: 91

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
            85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr
        435

<210> SEQ ID NO 92
<211> LENGTH: 439
<212> TYPE: PRT
<213> ORGANISM: Artificial Sequence
<220> FEATURE:
<223> OTHER INFORMATION: Synthetic Sequence

<400> SEQUENCE: 92

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
                20                  25                  30

Met Ser Leu Phe Ser Phe Ile Gly Ser Pro Arg Ile Asn Ala Thr Gly
            35                  40                  45

Gln Gly Val Thr Ile Phe Tyr Val Asp Arg Leu Gly Tyr Tyr Pro Tyr
        50                  55                  60

```
Ile Asp Ser Ile Thr Gly Val Thr Val Asn Gly Ile Pro Gln Lys
 65                  70                  75                  80

Ile Ser Leu Gln Asp His Leu Asp Lys Ala Lys Lys Asp Ile Thr Phe
                 85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr Glu
        435

<210> SEQ ID NO 93
<211> LENGTH: 454
<212> TYPE: PRT
<213> ORGANISM: Artificial Sequence
<220> FEATURE:
<223> OTHER INFORMATION: Synthetic Sequence
```

<400> SEQUENCE: 93

| | | | | | | | | | | | | | | |
|---|---|---|---|---|---|---|---|---|---|---|---|---|---|---|
|Asn|Phe|Arg|Ala|Pro|Pro|Val|Ile|Pro|Asn|Val|Pro|Phe|Leu|Trp|Ala|
|1| | | |5| | | | |10| | | | |15| |

Trp Asn Ala Pro Ser Glu Phe Cys Leu Gly Lys Phe Asp Glu Pro Leu
            20                  25                  30

Asp Met Ser Leu Phe Ser Phe Ile Gly Ser Pro Arg Ile Asn Ala Thr
        35                  40                  45

Gly Gln Gly Val Thr Ile Phe Tyr Val Asp Arg Leu Gly Tyr Tyr Pro
    50                  55                  60

Tyr Ile Asp Ser Ile Thr Gly Val Thr Val Asn Gly Gly Ile Pro Gln
65                  70                  75                  80

Lys Ile Ser Leu Gln Asp His Leu Asp Lys Ala Lys Lys Asp Ile Thr
                85                  90                  95

Phe Tyr Met Pro Val Asp Asn Leu Gly Met Ala Val Ile Asp Trp Glu
            100                 105                 110

Glu Trp Arg Pro Thr Trp Ala Arg Asn Trp Lys Pro Lys Asp Val Tyr
        115                 120                 125

Lys Asn Arg Ser Ile Glu Leu Val Gln Gln Asn Val Gln Leu Ser
130                 135                 140

Leu Thr Glu Ala Thr Glu Lys Ala Lys Gln Glu Phe Glu Lys Ala Gly
145                 150                 155                 160

Lys Asp Phe Leu Val Glu Thr Ile Lys Leu Gly Lys Leu Leu Arg Pro
                165                 170                 175

Asn His Leu Trp Gly Tyr Tyr Leu Phe Pro Asp Cys Tyr Asn His His
            180                 185                 190

Tyr Lys Lys Pro Gly Tyr Asn Gly Ser Cys Phe Asn Val Glu Ile Lys
        195                 200                 205

Arg Asn Asp Asp Leu Ser Trp Leu Trp Asn Glu Ser Thr Ala Leu Tyr
210                 215                 220

Pro Ser Ile Tyr Leu Asn Thr Gln Gln Ser Pro Val Ala Ala Thr Leu
225                 230                 235                 240

Tyr Val Arg Asn Arg Val Arg Glu Ala Ile Arg Val Ser Lys Ile Pro
                245                 250                 255

Asp Ala Lys Ser Pro Leu Pro Val Phe Ala Tyr Thr Arg Ile Val Phe
            260                 265                 270

Thr Asp Gln Val Leu Lys Phe Leu Ser Gln Asp Glu Leu Val Tyr Thr
        275                 280                 285

Phe Gly Glu Thr Val Ala Leu Gly Ala Ser Gly Ile Val Ile Trp Gly
    290                 295                 300

Thr Leu Ser Ile Thr Arg Thr Lys Glu Ser Cys Gln Ala Ile Lys Glu
305                 310                 315                 320

Tyr Met Asp Thr Thr Leu Asn Pro Tyr Ile Ile Asn Val Thr Leu Ala
                325                 330                 335

Ala Lys Met Cys Ser Gln Val Leu Cys Gln Gln Gly Val Cys Ile
            340                 345                 350

Arg Lys Asn Trp Asn Ser Ser Asp Tyr Leu His Leu Asn Pro Asp Asn
        355                 360                 365

Phe Ala Ile Gln Leu Glu Lys Gly Gly Lys Phe Thr Val Arg Gly Lys
    370                 375                 380

Pro Thr Leu Glu Asp Leu Glu Gln Phe Ser Glu Lys Phe Tyr Cys Ser
385                 390                 395                 400

Cys Tyr Ser Thr Leu Ser Cys Lys Glu Lys Ala Asp Val Lys Asp Thr

```
                        405                 410                 415
Asp Ala Val Asp Val Cys Ile Ala Asp Gly Val Cys Ile Asp Ala Phe
            420                 425                 430

Leu Lys Pro Pro Met Glu Thr Glu Glu Pro Gln Ile Phe Tyr Asn Ala
            435                 440                 445

Ser Pro Ser Thr Leu Ser
            450

<210> SEQ ID NO 94
<211> LENGTH: 452
<212> TYPE: PRT
<213> ORGANISM: Artificial Sequence
<220> FEATURE:
<223> OTHER INFORMATION: Synthetic Sequence

<400> SEQUENCE: 94

Arg Ala Pro Pro Val Ile Pro Asn Val Pro Phe Leu Trp Ala Trp Asn
1               5                   10                  15

Ala Pro Ser Glu Phe Cys Leu Gly Lys Phe Asp Glu Pro Leu Asp Met
            20                  25                  30

Ser Leu Phe Ser Phe Ile Gly Ser Pro Arg Ile Asn Ala Thr Gly Gln
        35                  40                  45

Gly Val Thr Ile Phe Tyr Val Asp Arg Leu Gly Tyr Tyr Pro Tyr Ile
    50                  55                  60

Asp Ser Ile Thr Gly Val Thr Val Asn Gly Gly Ile Pro Gln Lys Ile
65                  70                  75                  80

Ser Leu Gln Asp His Leu Asp Lys Ala Lys Lys Asp Ile Thr Phe Tyr
                85                  90                  95

Met Pro Val Asp Asn Leu Gly Met Ala Val Ile Asp Trp Glu Glu Trp
            100                 105                 110

Arg Pro Thr Trp Ala Arg Asn Trp Lys Pro Lys Asp Val Tyr Lys Asn
        115                 120                 125

Arg Ser Ile Glu Leu Val Gln Gln Asn Val Gln Leu Ser Leu Thr
    130                 135                 140

Glu Ala Thr Glu Lys Ala Lys Gln Glu Phe Glu Lys Ala Gly Lys Asp
145                 150                 155                 160

Phe Leu Val Glu Thr Ile Lys Leu Gly Lys Leu Leu Arg Pro Asn His
                165                 170                 175

Leu Trp Gly Tyr Tyr Leu Phe Pro Asp Cys Tyr Asn His His Tyr Lys
            180                 185                 190

Lys Pro Gly Tyr Asn Gly Ser Cys Phe Asn Val Glu Ile Lys Arg Asn
        195                 200                 205

Asp Asp Leu Ser Trp Leu Trp Asn Glu Ser Thr Ala Leu Tyr Pro Ser
    210                 215                 220

Ile Tyr Leu Asn Thr Gln Gln Ser Pro Val Ala Ala Thr Leu Tyr Val
225                 230                 235                 240

Arg Asn Arg Val Arg Glu Ala Ile Arg Val Ser Lys Ile Pro Asp Ala
                245                 250                 255

Lys Ser Pro Leu Pro Val Phe Ala Tyr Thr Arg Ile Val Phe Thr Asp
            260                 265                 270

Gln Val Leu Lys Phe Leu Ser Gln Asp Glu Leu Val Tyr Thr Phe Gly
        275                 280                 285

Glu Thr Val Ala Leu Gly Ala Ser Gly Ile Val Ile Trp Gly Thr Leu
    290                 295                 300

Ser Ile Thr Arg Thr Lys Glu Ser Cys Gln Ala Ile Lys Glu Tyr Met
```

```
                305                 310                 315                 320
Asp Thr Thr Leu Asn Pro Tyr Ile Ile Asn Val Thr Leu Ala Ala Lys
                325                 330                 335

Met Cys Ser Gln Val Leu Cys Gln Glu Gln Gly Val Cys Ile Arg Lys
                340                 345                 350

Asn Trp Asn Ser Ser Asp Tyr Leu His Leu Asn Pro Asp Asn Phe Ala
                355                 360                 365

Ile Gln Leu Glu Lys Gly Gly Lys Phe Thr Val Arg Gly Lys Pro Thr
        370                 375                 380

Leu Glu Asp Leu Glu Gln Phe Ser Glu Lys Phe Tyr Cys Ser Cys Tyr
385                 390                 395                 400

Ser Thr Leu Ser Cys Lys Glu Lys Ala Asp Val Lys Asp Thr Asp Ala
                405                 410                 415

Val Asp Val Cys Ile Ala Asp Gly Val Cys Ile Asp Ala Phe Leu Lys
                420                 425                 430

Pro Pro Met Glu Thr Glu Glu Pro Gln Ile Phe Tyr Asn Ala Ser Pro
                435                 440                 445

Ser Thr Leu Ser
        450

<210> SEQ ID NO 95
<211> LENGTH: 450
<212> TYPE: PRT
<213> ORGANISM: Artificial Sequence
<220> FEATURE:
<223> OTHER INFORMATION: Synthetic Sequence

<400> SEQUENCE: 95

Pro Pro Val Ile Pro Asn Val Pro Phe Leu Trp Ala Trp Asn Ala Pro
1               5                   10                  15

Ser Glu Phe Cys Leu Gly Lys Phe Asp Glu Pro Leu Asp Met Ser Leu
                20                  25                  30

Phe Ser Phe Ile Gly Ser Pro Arg Ile Asn Ala Thr Gly Gln Gly Val
            35                  40                  45

Thr Ile Phe Tyr Val Asp Arg Leu Gly Tyr Tyr Pro Tyr Ile Asp Ser
        50                  55                  60

Ile Thr Gly Val Thr Val Asn Gly Gly Ile Pro Gln Lys Ile Ser Leu
65                  70                  75                  80

Gln Asp His Leu Asp Lys Ala Lys Lys Asp Ile Thr Phe Tyr Met Pro
                85                  90                  95

Val Asp Asn Leu Gly Met Ala Val Ile Asp Trp Glu Glu Trp Arg Pro
                100                 105                 110

Thr Trp Ala Arg Asn Trp Lys Pro Lys Asp Val Tyr Lys Asn Arg Ser
            115                 120                 125

Ile Glu Leu Val Gln Gln Asn Val Gln Leu Ser Leu Thr Glu Ala
130                 135                 140

Thr Glu Lys Ala Lys Gln Glu Phe Glu Lys Ala Gly Lys Asp Phe Leu
145                 150                 155                 160

Val Glu Thr Ile Lys Leu Gly Lys Leu Leu Arg Pro Asn His Leu Trp
                165                 170                 175

Gly Tyr Tyr Leu Phe Pro Asp Cys Tyr Asn His His Tyr Lys Lys Pro
            180                 185                 190

Gly Tyr Asn Gly Ser Cys Phe Asn Val Glu Ile Lys Arg Asn Asp Asp
        195                 200                 205

Leu Ser Trp Leu Trp Asn Glu Ser Thr Ala Leu Tyr Pro Ser Ile Tyr
```

```
            210                 215                 220
Leu Asn Thr Gln Gln Ser Pro Val Ala Ala Thr Leu Tyr Val Arg Asn
225                 230                 235                 240

Arg Val Arg Glu Ala Ile Arg Val Ser Lys Ile Pro Asp Ala Lys Ser
                245                 250                 255

Pro Leu Pro Val Phe Ala Tyr Thr Arg Ile Val Phe Thr Asp Gln Val
            260                 265                 270

Leu Lys Phe Leu Ser Gln Asp Glu Leu Val Tyr Thr Phe Gly Glu Thr
        275                 280                 285

Val Ala Leu Gly Ala Ser Gly Ile Val Ile Trp Gly Thr Leu Ser Ile
    290                 295                 300

Thr Arg Thr Lys Glu Ser Cys Gln Ala Ile Lys Glu Tyr Met Asp Thr
305                 310                 315                 320

Thr Leu Asn Pro Tyr Ile Ile Asn Val Thr Leu Ala Ala Lys Met Cys
                325                 330                 335

Ser Gln Val Leu Cys Gln Glu Gln Gly Val Cys Ile Arg Lys Asn Trp
            340                 345                 350

Asn Ser Ser Asp Tyr Leu His Leu Asn Pro Asp Asn Phe Ala Ile Gln
        355                 360                 365

Leu Glu Lys Gly Gly Lys Phe Thr Val Arg Gly Lys Pro Thr Leu Glu
    370                 375                 380

Asp Leu Glu Gln Phe Ser Glu Lys Phe Tyr Cys Ser Cys Tyr Ser Thr
385                 390                 395                 400

Leu Ser Cys Lys Glu Lys Ala Asp Val Lys Asp Thr Asp Ala Val Asp
                405                 410                 415

Val Cys Ile Ala Asp Gly Val Cys Ile Asp Ala Phe Leu Lys Pro Pro
            420                 425                 430

Met Glu Thr Glu Glu Pro Gln Ile Phe Tyr Asn Ala Ser Pro Ser Thr
        435                 440                 445

Leu Ser
    450

<210> SEQ ID NO 96
<211> LENGTH: 428
<212> TYPE: PRT
<213> ORGANISM: Artificial Sequence
<220> FEATURE:
<223> OTHER INFORMATION: Synthetic Sequence

<400> SEQUENCE: 96

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
                20                  25                  30

Met Ser Leu Phe Ser Phe Ile Gly Ser Pro Arg Ile Asn Ala Thr Gly
            35                  40                  45

Gln Gly Val Thr Ile Phe Tyr Val Asp Arg Leu Gly Tyr Tyr Pro Tyr
        50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Asp Ile Thr Phe
                85                  90                  95

Tyr Met Pro Val Asp Asn Leu Gly Met Ala Val Ile Asp Trp Glu Glu
                100                 105                 110

Trp Arg Pro Thr Trp Ala Arg Asn Trp Lys Pro Lys Asp Val Tyr Lys
```

```
                 115                 120                 125
Asn Arg Ser Ile Glu Leu Val Gln Gln Asn Val Gln Leu Ser Leu
            130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
            195                 200                 205

Asn Asp Asp Leu Ser Trp Leu Trp Asn Glu Ser Thr Ala Leu Tyr Pro
            210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
            275                 280                 285

Gly Glu Thr Val Ala Leu Gly Ala Ser Gly Ile Val Ile Trp Gly Ser
            290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gly Val Cys Ile Arg
            340                 345                 350

Lys Asn Trp Asn Ser Ser Asp Tyr Leu His Leu Asn Pro Asp Asn Phe
            355                 360                 365

Ala Ile Gln Leu Glu Lys Gly Gly Lys Phe Thr Val Arg Gly Lys Pro
            370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile
            420                 425

<210> SEQ ID NO 97
<211> LENGTH: 429
<212> TYPE: PRT
<213> ORGANISM: Artificial Sequence
<220> FEATURE:
<223> OTHER INFORMATION: Synthetic Sequence

<400> SEQUENCE: 97

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
                20                  25                  30

Met Ser Leu Phe Ser Phe Ile Gly Ser Pro Arg Ile Asn Ala Thr Gly
            35                  40                  45

Gln Gly Val Thr Ile Phe Tyr Val Asp Arg Leu Gly Tyr Tyr Pro Tyr
```

```
            50                  55                  60
Ile Asp Ser Ile Thr Gly Val Thr Val Asn Gly Gly Ile Pro Gln Lys
 65                  70                  75                  80

Ile Ser Leu Gln Asp His Leu Asp Lys Ala Lys Lys Asp Ile Thr Phe
                 85                  90                  95

Tyr Met Pro Val Asp Asn Leu Gly Met Ala Val Ile Asp Trp Glu Glu
                100                 105                 110

Trp Arg Pro Thr Trp Ala Arg Asn Trp Lys Pro Lys Asp Val Tyr Lys
                115                 120                 125

Asn Arg Ser Ile Glu Leu Val Gln Gln Gln Asn Val Gln Leu Ser Leu
            130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
                180                 185                 190

Lys Lys Pro Gly Tyr Asn Gly Ser Cys Phe Asn Val Glu Ile Lys Arg
                195                 200                 205

Asn Asp Asp Leu Ser Trp Leu Trp Asn Glu Ser Thr Ala Leu Tyr Pro
210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
                260                 265                 270

Asp Gln Val Leu Lys Phe Leu Ser Gln Asp Glu Leu Val Tyr Thr Phe
                275                 280                 285

Gly Glu Thr Val Ala Leu Gly Ala Ser Gly Ile Val Ile Trp Gly Ser
                290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gly Val Cys Ile Arg
                340                 345                 350

Lys Asn Trp Asn Ser Ser Asp Tyr Leu His Leu Asn Pro Asp Asn Phe
                355                 360                 365

Ala Ile Gln Leu Glu Lys Gly Gly Lys Phe Thr Val Arg Gly Lys Pro
370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp
                420                 425
```

<210> SEQ ID NO 98  
<211> LENGTH: 430  
<212> TYPE: PRT  
<213> ORGANISM: Artificial Sequence  
<220> FEATURE:  
<223> OTHER INFORMATION: Synthetic Sequence

```
<400> SEQUENCE: 98

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Ser
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415
```

```
Ala Val Asp Val Cys Ile Ala Asp Gly Val Cys Ile Asp Ala
            420                 425                 430

<210> SEQ ID NO 99
<211> LENGTH: 431
<212> TYPE: PRT
<213> ORGANISM: Artificial Sequence
<220> FEATURE:
<223> OTHER INFORMATION: Synthetic Sequence

<400> SEQUENCE: 99

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Ser
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350
```

Lys Asn Trp Asn Ser Ser Asp Tyr Leu His Leu Asn Pro Asp Asn Phe
            355                 360                 365

Ala Ile Gln Leu Glu Lys Gly Gly Lys Phe Thr Val Arg Gly Lys Pro
        370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe
                420                 425                 430

<210> SEQ ID NO 100
<211> LENGTH: 441
<212> TYPE: PRT
<213> ORGANISM: Artificial Sequence
<220> FEATURE:
<223> OTHER INFORMATION: Synthetic Sequence

<400> SEQUENCE: 100

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Asn Val Gln Leu Ser Leu
130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

```
Gly Glu Thr Val Ala Leu Gly Ala Ser Gly Ile Val Ile Trp Gly Thr
        290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr Glu Glu Pro
        435                 440

<210> SEQ ID NO 101
<211> LENGTH: 443
<212> TYPE: PRT
<213> ORGANISM: Artificial Sequence
<220> FEATURE:
<223> OTHER INFORMATION: Synthetic Sequence

<400> SEQUENCE: 101

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205
```

```
Asn Asp Asp Leu Ser Trp Leu Trp Asn Glu Ser Thr Ala Leu Tyr Pro
            210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
            245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
            275                 280                 285

Gly Glu Thr Val Ala Leu Gly Ala Ser Gly Ile Val Ile Trp Gly Thr
            290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
            325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
            355                 360                 365

Ala Ile Gln Leu Glu Lys Gly Gly Lys Phe Thr Val Arg Gly Lys Pro
            370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
            405                 410                 415

Ala Val Asp Val Cys Ile Ala Asp Gly Val Cys Ile Asp Ala Phe Leu
            420                 425                 430

Lys Pro Pro Met Glu Thr Glu Glu Pro Gln Ile
            435                 440

<210> SEQ ID NO 102
<211> LENGTH: 445
<212> TYPE: PRT
<213> ORGANISM: Artificial Sequence
<220> FEATURE:
<223> OTHER INFORMATION: Synthetic Sequence

<400> SEQUENCE: 102

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
            35                  40                  45

Gln Gly Val Thr Ile Phe Tyr Val Asp Arg Leu Gly Tyr Tyr Pro Tyr
            50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
            85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
            115                 120                 125
```

```
Asn Arg Ser Ile Glu Leu Val Gln Gln Asn Val Gln Leu Ser Leu
            130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
            195                 200                 205

Asn Asp Asp Leu Ser Trp Leu Trp Asn Glu Ser Thr Ala Leu Tyr Pro
210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
            275                 280                 285

Gly Glu Thr Val Ala Leu Gly Ala Ser Gly Ile Val Ile Trp Gly Thr
290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
            355                 360                 365

Ala Ile Gln Leu Glu Lys Gly Gly Lys Phe Thr Val Arg Gly Lys Pro
370                 375                 380

Thr Leu Glu Asp Leu Glu Gln Phe Ser Gly Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
            420                 425                 430

Lys Pro Pro Met Glu Thr Glu Pro Gln Ile Phe Tyr
            435                 440                 445

<210> SEQ ID NO 103
<211> LENGTH: 447
<212> TYPE: PRT
<213> ORGANISM: Artificial Sequence
<220> FEATURE:
<223> OTHER INFORMATION: Synthetic Sequence

<400> SEQUENCE: 103

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
                20                  25                  30

Met Ser Leu Phe Ser Phe Ile Gly Ser Pro Arg Ile Asn Ala Thr Gly
            35                  40                  45
```

```
Gln Gly Val Thr Ile Phe Tyr Val Asp Arg Leu Gly Tyr Tyr Pro Tyr
     50                  55                  60

Ile Asp Ser Ile Thr Gly Val Thr Val Asn Gly Ile Pro Gln Lys
 65              70                  75                  80

Ile Ser Leu Gln Asp His Leu Asp Lys Ala Lys Lys Asp Ile Thr Phe
                 85                  90                  95

Tyr Met Pro Val Asp Asn Leu Gly Met Ala Val Ile Asp Trp Glu Glu
                100                 105                 110

Trp Arg Pro Thr Trp Ala Arg Asn Trp Lys Pro Lys Asp Val Tyr Lys
                115                 120                 125

Asn Arg Ser Ile Glu Leu Val Gln Gln Gln Asn Val Gln Leu Ser Leu
        130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
            195                 200                 205

Asn Asp Asp Leu Ser Trp Leu Trp Asn Glu Ser Thr Ala Leu Tyr Pro
210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
                260                 265                 270

Asp Gln Val Leu Lys Phe Leu Ser Gln Asp Glu Leu Val Tyr Thr Phe
                275                 280                 285

Gly Glu Thr Val Ala Leu Gly Ala Ser Gly Ile Val Ile Trp Gly Thr
                290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
                340                 345                 350

Lys Asn Trp Asn Ser Ser Asp Tyr Leu His Leu Asn Pro Asp Asn Phe
                355                 360                 365

Ala Ile Gln Leu Glu Lys Gly Gly Lys Phe Thr Val Arg Gly Lys Pro
                370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                    405                 410                 415

Ala Val Asp Val Cys Ile Ala Asp Gly Val Cys Ile Asp Ala Phe Leu
                    420                 425                 430

Lys Pro Pro Met Glu Thr Glu Glu Pro Gln Ile Phe Tyr Asn Ala
                    435                 440                 445

<210> SEQ ID NO 104
<211> LENGTH: 449
```

```
<212> TYPE: PRT
<213> ORGANISM: Artificial Sequence
<220> FEATURE:
<223> OTHER INFORMATION: Synthetic Sequence

<400> SEQUENCE: 104

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380
```

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
            405                 410                 415

Ala Val Asp Val Cys Ile Ala Asp Gly Val Cys Ile Asp Ala Phe Leu
        420                 425                 430

Lys Pro Pro Met Glu Thr Glu Pro Gln Ile Phe Tyr Asn Ala Ser
        435                 440                 445

Pro

<210> SEQ ID NO 105
<211> LENGTH: 451
<212> TYPE: PRT
<213> ORGANISM: Artificial Sequence
<220> FEATURE:
<223> OTHER INFORMATION: Synthetic Sequence

<400> SEQUENCE: 105

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Thr

-continued

```
            290                 295                 300
Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
                340                 345                 350

Lys Asn Trp Asn Ser Ser Asp Tyr Leu His Leu Asn Pro Asp Asn Phe
                355                 360                 365

Ala Ile Gln Leu Glu Lys Gly Gly Lys Phe Thr Val Arg Gly Lys Pro
370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe Leu
                420                 425                 430

Lys Pro Pro Met Glu Thr Glu Glu Pro Gln Ile Phe Tyr Asn Ala Ser
                435                 440                 445

Pro Ser Thr
    450

<210> SEQ ID NO 106
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 106

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
                35                  40                  45

Thr Gly Gln Gly Val Thr Ile Phe Tyr Val Asp Arg Leu Gly Tyr Tyr
            50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
            115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
                180                 185                 190

His Tyr Lys Lys Pro Gly Tyr Asn Gly Ser Cys Phe Asn Val Glu Ile
```

```
                195                 200                 205
Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Gly Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455

<210> SEQ ID NO 107
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 107

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
```

```
            100                 105                 110
Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Ala Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455

<210> SEQ ID NO 108
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 108

Leu Asn Phe Arg Ala Pro Pro Val Ile Pro Asn Val Pro Phe Leu Trp
```

-continued

```
1               5                   10                  15
Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
            50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
                115                 120                 125

Tyr Lys Asn Arg Ser Ile Glu Leu Val Gln Gln Asn Val Gln Leu
            130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
                180                 185                 190

His Tyr Lys Lys Pro Gly Tyr Asn Gly Ser Cys Phe Asn Val Glu Ile
                195                 200                 205

Lys Arg Asn Asp Asp Leu Ser Trp Leu Trp Asn Glu Ser Thr Ala Leu
                210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
                260                 265                 270

Phe Thr Asp Gln Val Leu Lys Phe Leu Ser Gln Asp Glu Leu Val Tyr
                275                 280                 285

Thr Phe Gly Glu Thr Val Ala Leu Gly Ala Ser Gly Ile Val Ile Trp
                290                 295                 300

Gly Cys Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

Ala Ala Lys Met Cys Ser Gln Val Leu Cys Gln Glu Gly Val Cys
                340                 345                 350

Ile Arg Lys Asn Trp Asn Ser Ser Asp Tyr Leu His Leu Asn Pro Asp
                355                 360                 365

Asn Phe Ala Ile Gln Leu Glu Lys Gly Gly Lys Phe Thr Val Arg Gly
                370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
                420                 425                 430
```

Phe Leu Lys Pro Pro Met Glu Thr Glu Pro Gln Ile Phe Tyr Asn
            435                 440                 445

Ala Ser Pro Ser Thr Leu Ser
    450                 455

<210> SEQ ID NO 109
<211> LENGTH: 455
<212> TYPE: PRT
<213> ORGANISM: Artificial Sequence
<220> FEATURE:
<223> OTHER INFORMATION: Synthetic Sequence

<400> SEQUENCE: 109

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Asp Trp Glu Asn Thr Arg Thr Lys Glu Ser Cys Gln Ala Ile Lys
305                 310                 315                 320

Glu Tyr Met Asp Thr Thr Leu Asn Pro Tyr Ile Ile Asn Val Thr Leu
                325                 330                 335

```
Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
            435                 440                 445

Ala Ser Pro Ser Thr Leu Ser
            450                 455

<210> SEQ ID NO 110
<211> LENGTH: 431
<212> TYPE: PRT
<213> ORGANISM: Artificial Sequence
<220> FEATURE:
<223> OTHER INFORMATION: Synthetic Sequence

<400> SEQUENCE: 110

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240
```

Val Arg Asn Arg Val Arg Glu Ala Ile Arg Val Ser Lys Ile Pro Asp
            245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
            275                 280                 285

Gly Glu Thr Val Ala Leu Gly Ala Ser Gly Ile Val Ile Trp Gly Thr
            290                 295                 300

Leu Ser Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
            325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
            355                 360                 365

Ala Ile Gln Leu Glu Lys Gly Gly Lys Phe Thr Val Arg Gly Lys Pro
            370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
            405                 410                 415

Ala Val Asp Val Cys Ile Ala Asp Gly Val Cys Ile Asp Ala Phe
            420                 425                 430

<210> SEQ ID NO 111
<211> LENGTH: 431
<212> TYPE: PRT
<213> ORGANISM: Artificial Sequence
<220> FEATURE:
<223> OTHER INFORMATION: Synthetic Sequence

<400> SEQUENCE: 111

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
            35                  40                  45

Gln Gly Val Thr Ile Phe Tyr Val Asp Arg Leu Gly Tyr Tyr Pro Tyr
            50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
            85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
            115                 120                 125

Asn Arg Ser Ile Glu Leu Val Gln Gln Gln Asn Val Gln Leu Ser Leu
            130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
            165                 170                 175

His Leu Trp Gly Tyr Leu Phe Pro Asp Cys Tyr Asn His His Tyr
                180                 185                 190

Lys Lys Pro Gly Tyr Asn Gly Ser Cys Phe Asn Val Glu Ile Lys Arg
                195                 200                 205

Asn Asp Asp Leu Ser Trp Leu Trp Asn Glu Ser Thr Ala Leu Tyr Pro
210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
                260                 265                 270

Asp Gln Val Leu Lys Phe Leu Ser Gln Asp Glu Leu Val Tyr Thr Phe
                275                 280                 285

Gly Glu Thr Val Ala Leu Gly Ala Ser Gly Ile Val Ile Trp Gly Thr
                290                 295                 300

Leu Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
                340                 345                 350

Lys Asn Trp Asn Ser Ser Asp Tyr Leu His Leu Asn Pro Asp Asn Phe
                355                 360                 365

Ala Ile Gln Leu Glu Lys Gly Gly Lys Phe Thr Val Arg Gly Lys Pro
                370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe
                420                 425                 430

<210> SEQ ID NO 112
<211> LENGTH: 431
<212> TYPE: PRT
<213> ORGANISM: Artificial Sequence
<220> FEATURE:
<223> OTHER INFORMATION: Synthetic Sequence

<400> SEQUENCE: 112

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
                20                  25                  30

Met Ser Leu Phe Ser Phe Ile Gly Ser Pro Arg Ile Asn Ala Thr Gly
                35                  40                  45

Gln Gly Val Thr Ile Phe Tyr Val Asp Arg Leu Gly Tyr Tyr Pro Tyr
                50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
                100                 105                 110

Trp Arg Pro Thr Trp Ala Arg Asn Trp Lys Pro Lys Asp Val Tyr Lys
            115                 120                 125

Asn Arg Ser Ile Glu Leu Val Gln Gln Gln Asn Val Gln Leu Ser Leu
        130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
            195                 200                 205

Asn Asp Asp Leu Ser Trp Leu Trp Asn Glu Ser Thr Ala Leu Tyr Pro
        210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Ala
290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
            370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe
            420                 425                 430

<210> SEQ ID NO 113
<211> LENGTH: 431
<212> TYPE: PRT
<213> ORGANISM: Artificial Sequence
<220> FEATURE:
<223> OTHER INFORMATION: Synthetic Sequence

<400> SEQUENCE: 113

Phe Arg Ala Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
 50                  55                  60

Ile Asp Ser Ile Thr Gly Val Thr Val Asn Gly Ile Pro Gln Lys
 65                  70                  75                  80

Ile Ser Leu Gln Asp His Leu Asp Lys Ala Lys Lys Asp Ile Thr Phe
                 85                  90                  95

Tyr Met Pro Val Asp Asn Leu Gly Met Ala Val Ile Asp Trp Glu Glu
                100                 105                 110

Trp Arg Pro Thr Trp Ala Arg Asn Trp Lys Pro Lys Asp Val Tyr Lys
                115                 120                 125

Asn Arg Ser Ile Glu Leu Val Gln Gln Asn Val Gln Leu Ser Leu
130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
                180                 185                 190

Lys Lys Pro Gly Tyr Asn Gly Ser Cys Phe Asn Val Glu Ile Lys Arg
                195                 200                 205

Asn Asp Asp Leu Ser Trp Leu Trp Asn Glu Ser Thr Ala Leu Tyr Pro
210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
                260                 265                 270

Asp Gln Val Leu Lys Phe Leu Ser Gln Asp Glu Leu Val Tyr Thr Phe
                275                 280                 285

Gly Glu Thr Val Ala Leu Gly Ala Ser Gly Ile Val Ile Trp Gly Gly
                290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
                340                 345                 350

Lys Asn Trp Asn Ser Ser Asp Tyr Leu His Leu Asn Pro Asp Asn Phe
                355                 360                 365

Ala Ile Gln Leu Glu Lys Gly Gly Lys Phe Thr Val Arg Gly Lys Pro
                370                 375                 380

Thr Leu Glu Asp Leu Glu Gln Phe Ser Glu Lys Phe Tyr Cys Ser Cys
385                 390                 395                 400

Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe
                420                 425                 430

<210> SEQ ID NO 114
<211> LENGTH: 431
<212> TYPE: PRT
<213> ORGANISM: Artificial Sequence
<220> FEATURE:

<223> OTHER INFORMATION: Synthetic Sequence

<400> SEQUENCE: 114

Phe Arg Gly Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
            20                  25                  30

Met Ser Leu Phe Ser Phe Ile Gly Ser Pro Arg Ile Asn Ala Thr Gly
        35                  40                  45

Gln Gly Val Thr Ile Phe Tyr Val Asp Arg Leu Gly Tyr Tyr Pro Tyr
    50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Ser
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335

Lys Met Cys Ser Gln Val Leu Cys Gln Glu Gln Gly Val Cys Ile Arg
            340                 345                 350

Lys Asn Trp Asn Ser Ser Asp Tyr Leu His Leu Asn Pro Asp Asn Phe
        355                 360                 365

Ala Ile Gln Leu Glu Lys Gly Gly Lys Phe Thr Val Arg Gly Lys Pro
    370                 375                 380

Thr Leu Glu Asp Leu Glu Gln Phe Ser Glu Lys Phe Tyr Cys Ser Cys
385                 390                 395                 400

```
Tyr Ser Thr Leu Ser Cys Lys Glu Lys Ala Asp Val Lys Asp Thr Asp
                405                 410                 415

Ala Val Asp Val Cys Ile Ala Asp Gly Val Cys Ile Asp Ala Phe
            420                 425                 430

<210> SEQ ID NO 115
<211> LENGTH: 431
<212> TYPE: PRT
<213> ORGANISM: Artificial Sequence
<220> FEATURE:
<223> OTHER INFORMATION: Synthetic Sequence

<400> SEQUENCE: 115

Phe Arg Gly Pro Pro Val Ile Pro Asn Val Pro Phe Leu Trp Ala Trp
1               5                   10                  15

Asn Ala Pro Ser Glu Phe Cys Leu Gly Lys Phe Asp Glu Pro Leu Asp
                20                  25                  30

Met Ser Leu Phe Ser Phe Ile Gly Ser Pro Arg Ile Asn Ala Thr Gly
            35                  40                  45

Gln Gly Val Thr Ile Phe Tyr Val Asp Arg Leu Gly Tyr Tyr Pro Tyr
        50                  55                  60

Ile Asp Ser Ile Thr Gly Val Thr Val Asn Gly Gly Ile Pro Gln Lys
65                  70                  75                  80

Ile Ser Leu Gln Asp His Leu Asp Lys Ala Lys Lys Asp Ile Thr Phe
                85                  90                  95

Tyr Met Pro Val Asp Asn Leu Gly Met Ala Val Ile Asp Trp Glu Glu
            100                 105                 110

Trp Arg Pro Thr Trp Ala Arg Asn Trp Lys Pro Lys Asp Val Tyr Lys
        115                 120                 125

Asn Arg Ser Ile Glu Leu Val Gln Gln Gln Asn Val Gln Leu Ser Leu
    130                 135                 140

Thr Glu Ala Thr Glu Lys Ala Lys Gln Glu Phe Glu Lys Ala Gly Lys
145                 150                 155                 160

Asp Phe Leu Val Glu Thr Ile Lys Leu Gly Lys Leu Leu Arg Pro Asn
                165                 170                 175

His Leu Trp Gly Tyr Tyr Leu Phe Pro Asp Cys Tyr Asn His His Tyr
            180                 185                 190

Lys Lys Pro Gly Tyr Asn Gly Ser Cys Phe Asn Val Glu Ile Lys Arg
        195                 200                 205

Asn Asp Asp Leu Ser Trp Leu Trp Asn Glu Ser Thr Ala Leu Tyr Pro
    210                 215                 220

Ser Ile Tyr Leu Asn Thr Gln Gln Ser Pro Val Ala Ala Thr Leu Tyr
225                 230                 235                 240

Val Arg Asn Arg Val Arg Glu Ala Ile Arg Val Ser Lys Ile Pro Asp
                245                 250                 255

Ala Lys Ser Pro Leu Pro Val Phe Ala Tyr Thr Arg Ile Val Phe Thr
            260                 265                 270

Asp Gln Val Leu Lys Phe Leu Ser Gln Asp Glu Leu Val Tyr Thr Phe
        275                 280                 285

Gly Glu Thr Val Ala Leu Gly Ala Ser Gly Ile Val Ile Trp Gly Ser
    290                 295                 300

Trp Glu Asn Thr Arg Thr Lys Glu Ser Cys Gln Ala Ile Lys Glu Tyr
305                 310                 315                 320

Met Asp Thr Thr Leu Asn Pro Tyr Ile Ile Asn Val Thr Leu Ala Ala
                325                 330                 335
```

```
Lys Met Cys Ser Gln Val Leu Cys Gln Glu Gln Gly Val Cys Ile Arg
            340             345             350
Lys Asn Trp Asn Ser Ser Asp Tyr Leu His Leu Asn Pro Asp Asn Phe
            355             360             365
Ala Ile Gln Leu Glu Lys Gly Gly Lys Phe Thr Val Arg Gly Lys Pro
        370             375             380
Thr Leu Glu Asp Leu Glu Gln Phe Ser Glu Lys Phe Tyr Cys Ser Cys
385             390             395             400
Tyr Ser Thr Leu Ser Cys Lys Glu Lys Ala Asp Val Lys Asp Thr Asp
            405             410             415
Ala Val Asp Val Cys Ile Ala Asp Gly Val Cys Ile Asp Ala Phe
            420             425             430
```